United States Patent
Drum et al.

(10) Patent No.: US 11,510,881 B2
(45) Date of Patent: Nov. 29, 2022

(54) COMPOSITIONS AND METHODS FOR PROTEIN EXPRESSION AND DELIVERY

(71) Applicant: National University of Singapore, Singapore (SG)

(72) Inventors: Chester Lee Drum, Singapore (SG); Nihar Masurkar, Singapore (SG); Siddharth Deshpande, Singapore (SG); Goutam Chakraborty, Singapore (SG); Girish Vallerinteavide Mavelli, Singapore (SG)

(73) Assignee: National University of Singapore, Singapore (SG)

( * ) Notice: Subject to any disclaimer, the term of this patent is extended or adjusted under 35 U.S.C. 154(b) by 479 days.

(21) Appl. No.: 16/340,089

(22) PCT Filed: Oct. 6, 2017

(86) PCT No.: PCT/SG2017/050505
§ 371 (c)(1),
(2) Date: Apr. 5, 2019

(87) PCT Pub. No.: WO2018/067075
PCT Pub. Date: Apr. 12, 2018

(65) Prior Publication Data
US 2021/0113484 A1 Apr. 22, 2021

Related U.S. Application Data

(60) Provisional application No. 62/405,613, filed on Oct. 7, 2016.

(51) Int. Cl.
*A61K 38/00* (2006.01)
*A61K 39/00* (2006.01)
*C07K 14/00* (2006.01)
*A61K 9/51* (2006.01)

(52) U.S. Cl.
CPC ............ *A61K 9/5169* (2013.01); *A61K 38/00* (2013.01); *A61K 39/00* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 2003/0124741 A1 | 7/2003 | Yamashita | |
| 2019/0030134 A1* | 1/2019 | Lim | A61K 47/10 |

FOREIGN PATENT DOCUMENTS

WO    WO 2016/122414 A1    8/2016

OTHER PUBLICATIONS

Levi et al. Mechanism of Ferritin Iron Uptake: Activity of the H-chain and Deletion Mapping of the Ferro-oxidase Site. I. Biol. Chem., 1988, 263: 18086-18092.*
Fan et al. A Helix Swapping Study of Two Protein Cages. Biochemistry 2009, 48, 5623-5630.*
Ohtomo et al. A Physicochemical and Mutational Analysis of Intersubunit Interactions of *Escherichia coli* Ferritin A. Biochemistry 2015, 54, 6243-6251.*
Swift et al. Efficient Self-Assembly of Archaeoglobus fulgidus Ferritin around Metallic Cores. Langmuir 2009, 25(9), 5219-5225.*
WP_010878337.1. ferritin [Archaeoglobus fulgidus]. Dated May 15, 2013.*
Kanekiyo et al. Self-assembling influenza nanoparticle vaccines elicit broadly neutralizing H1N1 antibodies. Nature. Jul. 4, 2013; 499 (7456): 102-106.*
Cheung-Lau, J.C., et al., Engineering a Well-Ordered, Functional Protein-Gold Nanoparticle Assembly, J. Inorg. Biochem 130:59-68, Oct. 11, 2013.
Johnson, E., et al., Crystal Structures of a Tetrahedal Open Pore Ferritin from the Hyperthermophilic Archaeon *Archaeoglobus fulgidus*, Structure 13(4):637-648, Apr. 2005.
Tatur, J., et al., Crystal Structure of the Ferritin from the Hyperthermophilic Archaeal Anaerobe *Pyrococcus furiosus*, J. Biol. Inorg. Chem. 12(5):615-60, Feb. 16, 2007.
Zhang, Y., and B.P. Orner, Self-Assembly in the Ferritin Nano-Cage Protein Superfamily, Int. J. Mol. Sci. 12(8):5406-5421, Aug. 22, 2011.
Ingrassia, R., et al., Mutations of Ferritin H Chain C-Terminus Produced by Nucleotide Insertions Have Altered Stability and Functional Properties, J. Biochem., 139(5):881-885, May 2006.
Baraibar, M.A., et al., Iron-Mediated Aggregation and a Localized Structural Change Characterize Ferritin from a Mutant Light Chain Polypeptide That Causes Neurodegeneration, J. Biol. Chem. 283(46):31679-31689.
Levi., S., et al., Mechanism of Ferritin Iron Uptake: Activity of the H-Chain and Deletion Mapping of the Ferro-Oxidase Site, a Study of Iron Uptake and Ferro-Oxidase Activity of Human Liver, Recombinant H-Chain Ferritins, and of two H-Chain Deletion Mutants, J. Biol. Chem., 263(34):18086-18092.
Ohtomo, H., et al., A Physicochemical and Mutational Analysis of Intersubunit Interactions of *Escherichia coli* Ferritin A., Biochemistry 54(40):6243-6251, Sep. 24, 2015.
Kilic, M.A., et al., Stability of a 24-Meric Homopolymer: Comparative Studies of Assembly-Defective Mutants of *Rhodobacter capsulatus* Bacterioferritin and the Native Protein, Protein Sci., 12(8):1663-1674, Aug. 2003.
Hartl, F.U., and M. Hayer-Hartl, Molecular Chaperone Functions in Proein Folding and Proteostasis, Nat. Struct. Mol. Biol. 16:574-581, 2009.

(Continued)

*Primary Examiner* — Nianxiang Zou
(74) *Attorney, Agent, or Firm* — Knobbe, Martens, Olson & Bear, LLP

(57) ABSTRACT

Methods and compositions that provide an environment that promotes enhanced protein expression and/or folding are provided. More particularly, engineered thermostable ferritin assemblies capable of encapsulating polypeptides, nucleic acids or small molecules, which includes a modified ferritin subunit which lacks an unstructured carboxy-terminal sequence are provided. Methods and compositions for delivery of protein therapeutics are also provided.

25 Claims, 44 Drawing Sheets

Specification includes a Sequence Listing.

(56) References Cited

OTHER PUBLICATIONS

Daggett, V., and A. Fersht, The Present View of the Mechanism of Protein Folding, A. Nat. Rev. Mol. Cell. Biol. 4:497-502, 2003.
Kim, Y.E., et al., Molecular Chaperone Functions in Protein Folding and Proteostasis, Annu. Rev. Biochem. 82:323-355, 2013.
Patterson, D.P., et al., Rescuing Recombinant Proteins by Sequestration into the P22 VLP, Chem. Commun. (Camb). 49:10412-10414, 2013.
Comellas-Aragones, M., et al., A Virus-Based Single-Enzyme Nanoreactor, Nat. Nanotechnol. 2:635-639, 2007.
International Search Report issued in PCT/SG2017/050505 dated Nov. 27, 2017.
Hartl, F.U. et al., Nature. 475, 324-332 (2011).
Deshpande et al., "Thermostable exoshells fold and stabilize recombinant proteins", Nat. Commun. 8: 1442 (2017).
Fan et al., "A Helix Swapping Study of Two Protein Cages", Biochemistry, 48(24):5623-30 (2009).
Hempstead et al., "Comparison of the Three-dimensional Structures of Recombinant Human H and Horse L Ferritins at High Resolution", J. Mol. Biol., 268(2):424-48 (1997).
Levi et al., Mutational analysis of the channel and loop sequences of human ferritin H-Chain. Biochem. J. 1989, 264, 381-388.
Sana et al., "The role of Nonconserved Residues of *Archaeoglobus fulgidus* Ferritin on its Unique Structure and Biophysical Properties", The Journal of Biological Chemistry, 2013, 288(45):32663-32672.
Szilágyi and Závodszky. "Structural differences between mesophilic, moderately thermophilic and extremely thermophilic protein subunits: results of a comprehensive survey", Structure, May 15, 2000;8(5):493-504.
Taylor et al., "Discrimination of thermophilic and mesophilic proteins", BMC Structural Biology, 2010, 10, S5, pp. 1-10.

* cited by examiner

|  | 30mM | 600mM |
|---|---|---|
| WT | 4.28 ± 1.3 | 11.12 ± 2.6 |
| ΔC(+) | 11.65 ± 2.8 | 11.51 ± 2.8 |
| ΔC(−) | 11.54 ± 2.8 | 11.56 ± 3.1 |
| ΔC(+/−) | 11.97 ± 2.9 | 11.11 ± 3.0 |

|  | pH 5.8 | pH 8.0 |
|---|---|---|
| ΔC(−) | 11.42 ± 2.7 | 11.56 ± 3.1 |
| F116H(+) | 7.14 ± 2.0 | 11.29 ± 2.9 |
| F116H(−) | 7.16 ± 1.7 | 11.74 ± 3.1 |
| F116H(+/−) | 7.11 ± 0.9 | 11.35 ± 1.8 |

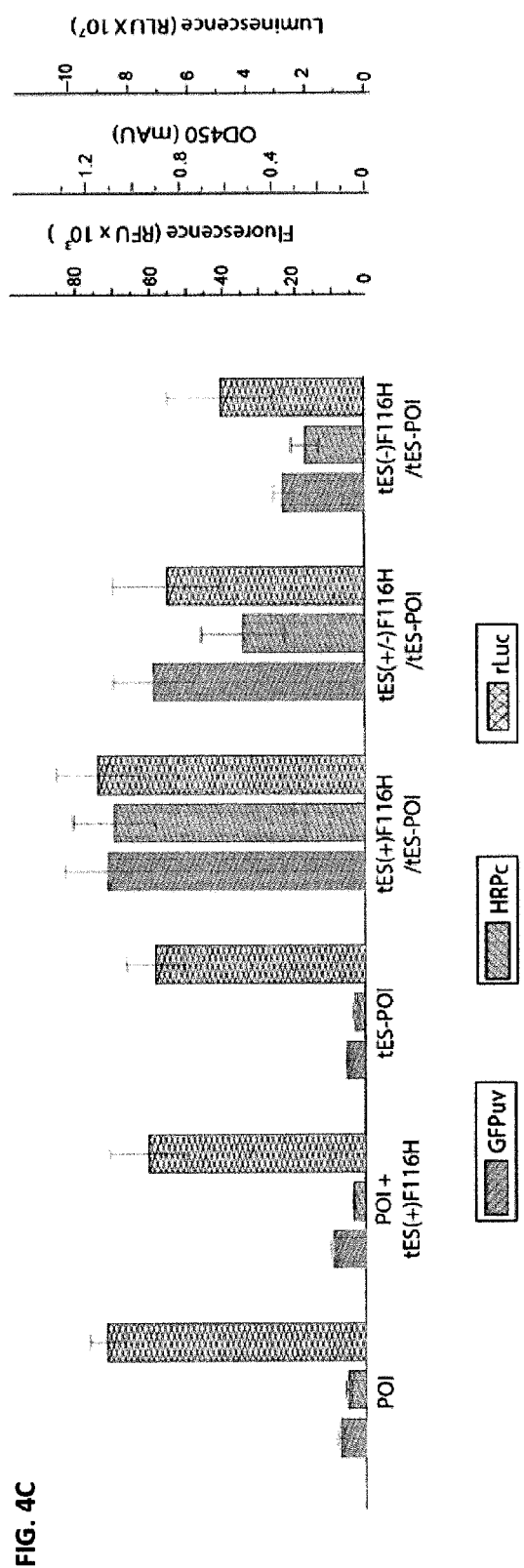
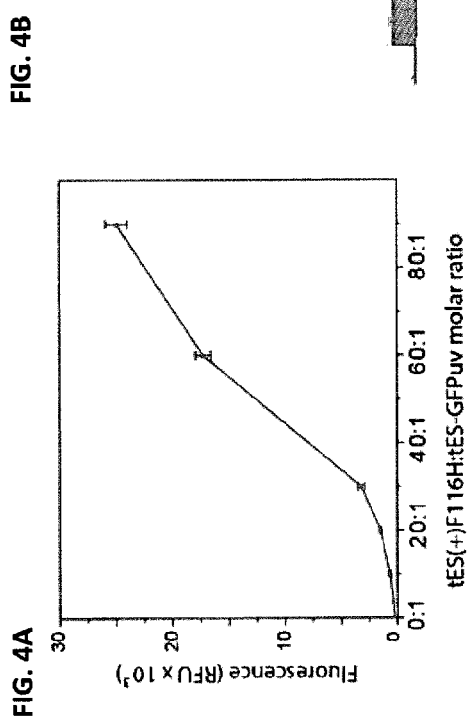
FIG. 4A
FIG. 4B
FIG. 4C

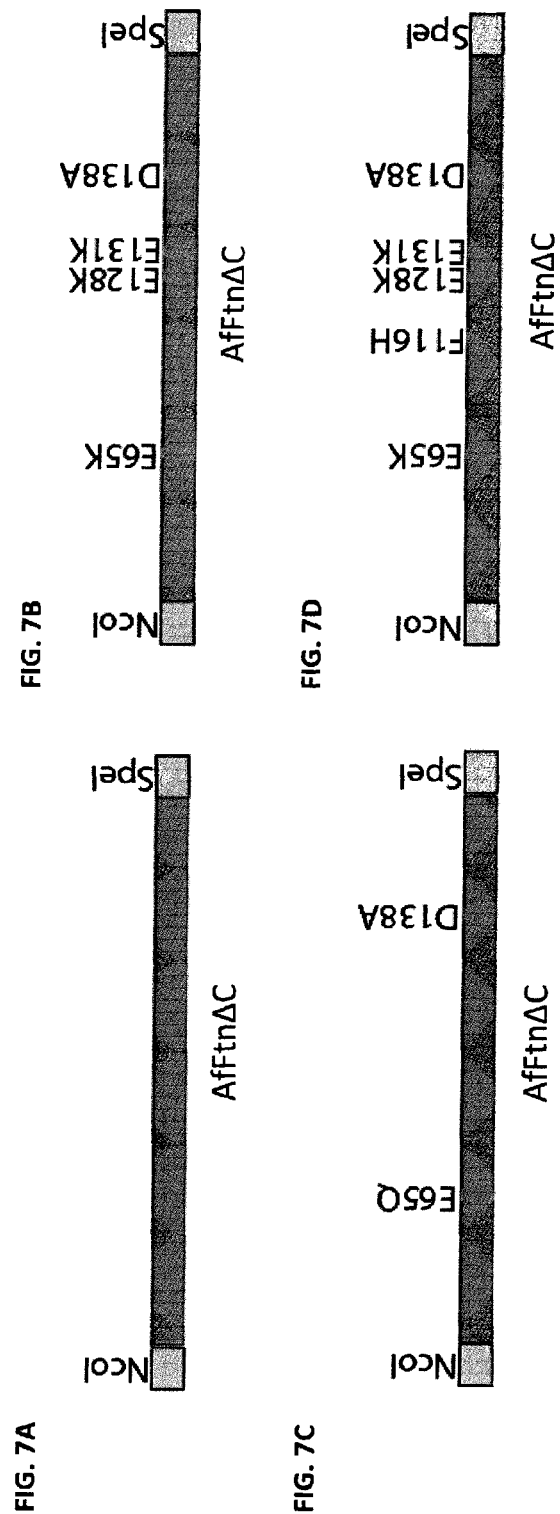

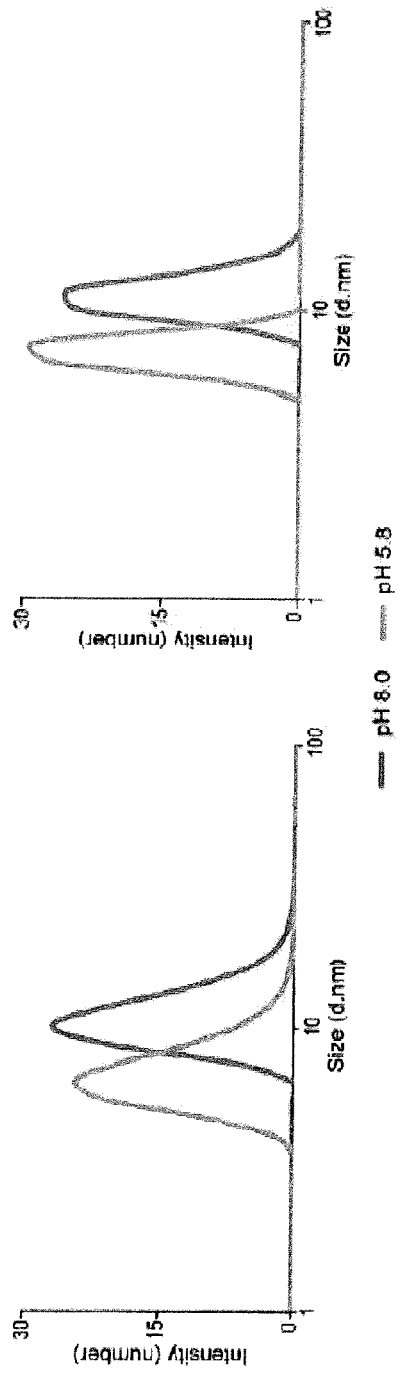
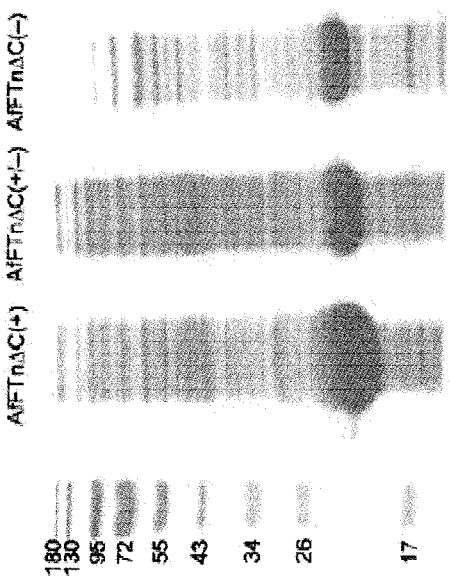
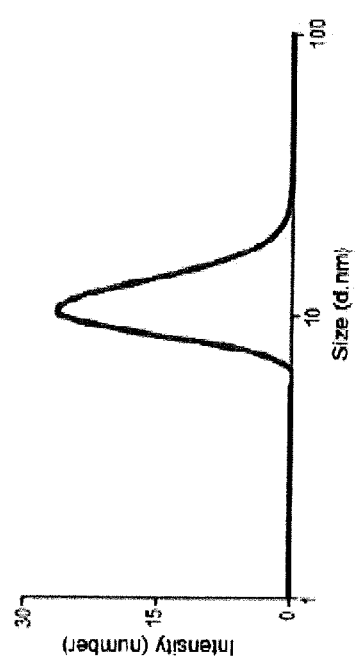
FIG. 9C
FIG. 9D
FIG. 9E
FIG. 9F

|  | Iron concentration (μM) |
|---|---|
| WT | 97.97 ± 3.51 |
| tES(-) | 58.61 ± 2.21 |
| tES(+) | 24.65 ± 0.90 |
| tES(+/-) | 18.45 ± 0.85 |
| tES(+)F116H | 20.66 ± 0.88 |
| tES(+)F116H/tES-GFPuv | 1.73 ± 0.09 |
| tES(+)F116H/tES-HRPc | 1.61 ± 0.02 |
| tES(+)F116H/tES-rLuc | 1.20 ± 0.03 |

Absorbance (280 nm)

SEQUENCE LISTING

<160> NUMBER OF SEQ ID NOS: 8

<210> SEQ ID NO 1
<211> LENGTH: 173
<212> TYPE: PRT
<213> ORGANISM: Archaeoglobus fulgidus

<400> SEQUENCE: 1

Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
    50                  55                  60

Glu Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

Val Asn Val Thr Lys Arg Ile His Glu Leu Val Glu Met Ala Met Gln
            100                 105                 110

Glu Lys Asp Phe Ala Thr Tyr Asn Phe Leu Gln Trp Tyr Val Ala Glu
        115                 120                 125

Gln Val Glu Glu Ala Ser Ala Leu Asp Ile Val Glu Lys Leu Arg
    130                 135                 140

Leu Ile Gly Glu Asp Lys Arg Ala Leu Leu Phe Leu Asp Lys Glu Leu
145                 150                 155                 160

Ser Leu Arg Gln Phe Thr Pro Pro Ala Glu Glu Glu Lys
                165                 170

<210> SEQ ID NO 2
<211> LENGTH: 166
<212> TYPE: PRT
<213> ORGANISM: Artificial Sequence
<220> FEATURE:
<223> OTHER INFORMATION: AfFtn subunit with truncation of unstructured
      C-terminus

<400> SEQUENCE: 2

Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
    50                  55                  60

Glu Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

Val Asn Val Thr Lys Arg Ile His Glu Leu Val Glu Met Ala Met Gln

```
            100                 105                 110

Glu Lys Asp Phe Ala Thr Tyr Asn Phe Leu Gln Trp Tyr Val Ala Glu
            115                 120                 125

Gln Val Glu Glu Ala Ser Ala Leu Asp Ile Val Glu Lys Leu Arg
        130                 135                 140

Leu Ile Gly Glu Asp Lys Arg Ala Leu Leu Phe Leu Asp Lys Glu Leu
145                 150                 155                 160

Ser Leu Arg Gln Thr Ser
                165

<210> SEQ ID NO 3
<211> LENGTH: 166
<212> TYPE: PRT
<213> ORGANISM: Artificial Sequence
<220> FEATURE:
<223> OTHER INFORMATION: AfFtn net positive variant subunit with
      truncation of unstructured C-terminus

<400> SEQUENCE: 3

Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
    50                  55                  60

Lys Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

Val Asn Val Thr Lys Arg Ile His Glu Leu Val Glu Met Ala Met Gln
            100                 105                 110

Glu Lys Asp Phe Ala Thr Tyr Asn Phe Leu Gln Trp Tyr Val Ala Lys
            115                 120                 125

Gln Val Lys Glu Glu Ala Ser Ala Leu Ala Ile Val Glu Lys Leu Arg
        130                 135                 140

Leu Ile Gly Glu Asp Lys Arg Ala Leu Leu Phe Leu Asp Lys Glu Leu
145                 150                 155                 160

Ser Leu Arg Gln Thr Ser
                165

<210> SEQ ID NO 4
<211> LENGTH: 166
<212> TYPE: PRT
<213> ORGANISM: Artificial Sequence
<220> FEATURE:
<223> OTHER INFORMATION: AfFtn net neutral variant subunit with
      truncation of unstructured C-terminus

<400> SEQUENCE: 4

Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
```

```
            50                  55                  60
Gln Arg Gly Gly Arg Val Lys Leu Tyr Ala Val Glu Pro Pro Ser
 65                  70                  75                  80

Glu Trp Asp Ser Pro Leu Ala Ala Phe Glu His Val Tyr Glu His Glu
                 85                  90                  95

Val Asn Val Thr Lys Arg Ile His Glu Leu Val Glu Met Ala Met Gln
                100                 105                 110

Glu Lys Asp Phe Ala Thr Tyr Asn Phe Leu Gln Trp Tyr Val Ala Glu
            115                 120                 125

Gln Val Glu Glu Ala Ser Ala Leu Ala Ile Val Glu Lys Leu Arg
            130                 135                 140

Leu Ile Gly Glu Asp Lys Arg Ala Leu Leu Phe Leu Asp Lys Glu Leu
145                 150                 155                 160

Ser Leu Arg Gln Thr Ser
                165
```

<210> SEQ ID NO 5
<211> LENGTH: 166
<212> TYPE: PRT
<213> ORGANISM: Artificial Sequence
<220> FEATURE:
<223> OTHER INFORMATION: AfFtn subunit with truncation of unstructured
      C-terminus and F116H mutation

<400> SEQUENCE: 5

```
Met Ala Ser Ile Ser Glu Lys Met Val Glu Ala Leu Asn Arg Gln Ile
  1               5                  10                  15

Asn Ala Glu Ile Tyr Ser Ala Tyr Leu Tyr Leu Ser Met Ala Ser Tyr
                 20                  25                  30

Phe Asp Ser Ile Gly Leu Lys Gly Phe Ser Asn Trp Met Arg Val Gln
            35                  40                  45

Trp Gln Glu Glu Leu Met His Ala Met Lys Met Phe Asp Phe Val Ser
 50                  55                  60

Glu Arg Gly Gly Arg Val Lys Leu Tyr Ala Val Glu Glu Pro Pro Ser
 65                  70                  75                  80

Glu Trp Asp Ser Pro Leu Ala Ala Phe Glu His Val Tyr Glu His Glu
                 85                  90                  95

Val Asn Val Thr Lys Arg Ile His Glu Leu Val Glu Met Ala Met Gln
                100                 105                 110

Glu Lys Asp His Ala Thr Tyr Asn Phe Leu Gln Trp Tyr Val Ala Glu
            115                 120                 125

Gln Val Glu Glu Ala Ser Ala Leu Asp Ile Val Glu Lys Leu Arg
            130                 135                 140

Leu Ile Gly Glu Asp Lys Arg Ala Leu Leu Phe Leu Asp Lys Glu Leu
145                 150                 155                 160

Ser Leu Arg Gln Thr Ser
                165
```

<210> SEQ ID NO 6
<211> LENGTH: 12
<212> TYPE: PRT
<213> ORGANISM: Artificial Sequence
<220> FEATURE:
<223> OTHER INFORMATION: Artificial peptide #1

<400> SEQUENCE: 6

```
Tyr His Trp Tyr Gly Tyr Thr Pro Gln Asn Val Ile
  1               5                  10
```

```
<210> SEQ ID NO 7
<211> LENGTH: 6
<212> TYPE: PRT
<213> ORGANISM: Artificial Sequence
<220> FEATURE:
<223> OTHER INFORMATION: Artificial peptide #2

<400> SEQUENCE: 7

Leu Ala Arg Leu Leu Thr
1               5

<210> SEQ ID NO 8
<211> LENGTH: 166
<212> TYPE: PRT
<213> ORGANISM: Artificial Sequence
<220> FEATURE:
<223> OTHER INFORMATION: AfFtn net positive variant subunit with
      truncation of unstructured C-terminus and F116H mutation

<400> SEQUENCE: 8

Met Ala Ser Ile Ser Glu Lys Met Val Glu Ala Leu Asn Arg Gln Ile
1               5                   10                  15

Asn Ala Glu Ile Tyr Ser Ala Tyr Leu Tyr Leu Ser Met Ala Ser Tyr
            20                  25                  30

Phe Asp Ser Ile Gly Leu Lys Gly Phe Ser Asn Trp Met Arg Val Gln
        35                  40                  45

Trp Gln Glu Glu Leu Met His Ala Met Lys Met Phe Asp Phe Val Ser
    50                  55                  60

Lys Arg Gly Gly Arg Val Lys Leu Tyr Ala Val Glu Glu Pro Pro Ser
65                  70                  75                  80

Glu Trp Asp Ser Pro Leu Ala Ala Phe Glu His Val Tyr Glu His Glu
                85                  90                  95

Val Asn Val Thr Lys Arg Ile His Glu Leu Val Glu Met Ala Met Gln
            100                 105                 110

Glu Lys Asp His Ala Thr Tyr Asn Phe Leu Gln Trp Tyr Val Ala Lys
        115                 120                 125

Gln Val Lys Glu Glu Ala Ser Ala Leu Ala Ile Val Glu Lys Leu Arg
    130                 135                 140

Leu Ile Gly Glu Asp Lys Arg Ala Leu Leu Phe Leu Asp Lys Glu Leu
145                 150                 155                 160

Ser Leu Arg Gln Thr Ser
                165
```

COMPOSITIONS AND METHODS FOR PROTEIN EXPRESSION AND DELIVERY

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Substitiute_Sequence_Listing_MARKS50-003APC, the date of creation of the ASCII text file is Feb. 3, 2020, and the size of the ASCII text file is 10.1 KB.

FIELD OF THE INVENTION

The present invention relates to methods and compositions that provide an environment that promotes enhanced protein expression and/or folding. More particularly, the present invention provides engineered thermostable ferritin assemblies capable of encapsulating polypeptides and nucleic acids. The present invention also provides methods and compositions for delivery of protein therapeutics.

BACKGROUND OF THE INVENTION

The pathway from nascent polypeptide to functional protein structure is determined by a balance of factors, some working in favour of, and many against, the successful folding of the end product (Hartl, F. U. and Hayer-Hartl, M., Nat. Struct. Mol. Biol. 16, 574-581 (2009); Daggett, V. and A. Fersht, A. Nat. Rev. Mol. Cell. Biol. 4, 497-502 (2003)). Natural chaperones prevent the aggregation of unfolded or partially-folded intermediates, undergo specific interactions that bias folding along productive energetic pathways, and exert kinetic effects that accommodate folding processes of widely varying time scales (Hartl, F. U. et al., Nature. 475, 324-332 (2011); Kim, Y. E. et al., Annu. Rev. Biochem. 82, 323-355 (2013)). Recombinant protein expression is fundamental to both basic and applied biology. However, methods for providing a permissive folding environment while preventing aggregation of unfolded intermediates remain a central challenge.

Studies using the P22 VLP bacteriophage, assembled from 420 copies of coat protein in addition to 130-300 copies of an additional scaffold protein, have shown sequestration of recombinant protein within the interior surface (Patterson, D. P. et al. Chem. Commun. (Camb). 49, 10412-10414 (2013)). However, the recovery of proteins from the capsids is more challenging and detrimental to the protein due to the harsh conditions adopted (Comellas-Aragones, M. et al., Nat Nanotechnol. 2, 635-639 (2007)).

Accordingly, there is a significant unmet need for methods that provide a permissive folding environment to enhance protein expression.

SUMMARY OF THE INVENTION

The present invention is based, in part, on the development of a method for functional polypeptide expression by surrounding a nascent polypeptide with an engineered nanoencapsulator (NE) shell, which is an engineered ferritin assembly made up of 24 subunits. The engineered ferritin assembly described herein protects the encapsulated polypeptide from intracellular aggregation while simultaneously providing a conducive nanoenvironment for the creation of a functional polypeptide. Without being bound by theory, it appears that tight steric and electrostatic complementarity to an internalized substrate prevents aggregation during the folding process while stabilizing correctly folded tertiary structures. Moreover, the NE is protective against a wide range of denaturants and provides enhanced thermostability. Using an expression host (e.g., E. coli), the soluble protein-of-interest (POI)-NE complex can be purified and manipulated in an aqueous buffer to perform functions such as disulfide oxidation, protection from proteolytic degradation, and prevention of inclusion body formation, that would ordinarily be unattainable in, e.g., E. coli cytosol. As also demonstrated herein, the engineered ferritin assembly can be designed for controlled release of the encapsulated polypeptide. Further, the engineered ferritin assembly can be used to deliver the encapsulated polypeptide into a target cell. The engineered ferritin assembly can be also be used to encapsulate and deliver nucleic acids or small molecules.

As a platform with which to dictate the nanoenvironment of a nascent polypeptide, nanoencapsulation is applicable in both basic studies of protein folding and applied uses within protein production. The ability to encapsulate a single polypeptide within a thermostable shell can have implications for nanotechnology, therapeutic protein delivery, and the general manipulation of enzymes and other functional proteins.

A variation of the invention involves surrounding a nucleic acid with an engineered nanoencapsulator (NE) shell.

BRIEF DESCRIPTION OF THE DRAWINGS

FIG. 1A. Surface representations of the 24-subunit AfFtn assembly showing the external shell, one of four ~4.5 nm pores, and an alternative visualization with six subunits digitally removed and a rendered surface of horseradish peroxidase isoenzyme C (HRPC) inside the aqueous volume of the shell. FIG. 1B. Dynamic light scattering of the stabilizing effect of a C-terminus truncation. FIG. 1C. Using the stabilized truncation, an additional F to H mutation produced pH-titratable assembly and disassembly. Table shows summary data for seven recombinantly expressed shells and engineered mutants. WT=wildtype, ΔC=C-terminus truncation mutant, (+)=a mutant with net positive interior, (−)=a mutant with net negative interior, "(+/−)"=a mutant with net neutral interior, F116H=pH sensitive mutant. All pH-titratable shells are derived from the corresponding ΔC mutants.

FIG. 2A. Schematic of terminologies. FIG. 2B. SDS gel of GFPuv expressed as a His-tagged protein, Histagged GFPuv (without being fused to an NE subunit [linker]) coexpressed with an NE shell, a fusion protein to an NE subunit but no shell, His-tagged GFPuv as a fusion protein to an NE subunit—coexpressed—with positive, neutral, and negative interior shells (induced at O.D.$_{600}$=0.8). The corresponding Western blot demonstrates soluble expression only in the presence of linker and shell using an antibody directed to an engineered cMyc-epitope on the Cterminus of the POI: GFPuv, HRPC, and luciferase. FIG. 2C. Size-exclusion profile of purified complexes where the POI is GFPuv, HRPC, and luciferase. In all cases, the His-tagged subunit co-purifies with NE shells indicating assembly. FIG. 2D. SDS gel of the purified GFPuv, HRPC, and luciferase showing bands of h6NE-POI and NE subunit.

FIG. 3A. Functional analysis of GFPuv expression by fluorescence spectroscopy (excitation: 395 nm and emission: 415-600 nm). FIG. 3B. Comparison of luciferase activity among the three cages (500 nM) using D-luciferin, ATP, and $Mg^{2+}$. Recombinant luciferase (600 pM) and AfFtnΔC(−) (500 nM) were used as positive and negative control, respectively. Kinetics of luciferase activity for recombinant luciferase (FIG. 3C) and h6NE-luciferase (+/−) (FIG. 3D). The kinetic parameters Km and Vmax were determined. FIG. 3E. Functional analysis of HRPC expression by measuring HRPC activity at 450 nm using 3,3',5,5'-Tetramethylbenzidine (TMB). FIG. 3F. Effect of cofactors/additives on HRPC activity inside the NE. HRPC activity was assessed from cell lysates processed under identical conditions in presence of cofactors calcium and hemin and additives (oxidizing and reducing agents) (n=3, error bar represents±S.D.).

FIGS. 4A-4C show effects of tES variants on the functional yield of internalized peptides. FIG. 4A shows effect of different molar ratios of tES(+) subunits to tES-GFPuv on GFPuv activity using in vitro folding. FIG. 4B shows functional analysis of the in vitro folded GFPuv, HRPC, and rLuc in presence and absence of tES by measurement of fluorescence, absorbance, and luminescence, respectively. FIG. 4C shows analysis of GFPuv, HRPC, and rLuc under a combination of co-expression conditions measured by fluorescence, absorbance, and luminescence, respectively (details in FIG. 1b).

FIG. 5A. Size-exclusion chromatography of F116HNE-GFPuv(+) and F116HNE-HRPC (+) at pH 8.0 and 5.8. Each fraction was analyzed for GFPuv and HRPC activity and data overlaid on to the chromatogram. Peak 2 represents the released h6NE-GFPuv and h6NE-HRPC. FIG. 5B. ELISA-based epitope protection assay to study internalization of GFP and HRP. The ELISA readout with peak 2 fraction was higher compared to peak 1 fraction, indicating the POI being expressed within the shell. FIG. 5C. Protease protection assay with TEV protease, wherein h6NE-GFPuvTEV(+) and h6NEGFPuvTEV were treated with TEVprotease. Western blotting showed that the protease cleaved h6NE-GFPuvTEV and not h6NE-GFPuvTEV(+) explaining the internalization of GFPuv. FIG. 5D. Co-immunoprecipitation using anti-c-Myc antibody. SDS gel with h6NE-luciferase(+/−), AfFtnΔC-(+) (negative control) and h6NE-luciferase (positive control). 'FT' and 'E' represents flow through and elute, respectively. The corresponding Western blot (bottom) shows luciferase band for h6NE-luciferase(+/−) and h6NE-luciferase in the flow through and elute, respectively. FIG. 5E. Recovery of active proteins from the NE. F116HNE-GFPuv(+), F116HNE-HRPC(+) and F116HNE-rLuc(+) were subjected to cage break at pH 5.8. The released POI was proteolysed by FXa to separate GFPuv, HRPC and rLuc. Western blotting confirmed the separation of the POI from NE(+). (n=3, error bar represents±S.D.).

FIGS. 7A-7F show a schematic representation of various constructs with restriction sites. FIG. 7A. AfFtn with truncated C-terminus contributing to a net negative interior when assembled [AfFtnΔC(−)]. FIG. 7B. AfFtn with truncated C-terminus and four point mutations (E65K, E128K, E131K, and D138A) contributing to a net positive interior when assembled [AfFtnΔC(+)]. FIG. 7C. AfFtn with truncated C-terminus and two point mutations (E65Q and D138A) contributing to a net neutral interior when assembled [AfFtnΔC(+/−)]. FIG. 7D. AfFtn with truncated C-terminus, a positive interior, and an F116H mutation for studying the effect of pH on cage disassembly [F116H(+)]. Constructs in FIGS. 7A-7D were cloned in a pRSF1b vector. FIG. 7E. Fusion of AfFtn with truncated C-terminus and POI (GFP/HRP/luciferase). N-terminus His-tag and C-terminus c-Myc epitope are highlighted [h6NE-POI]. FIG. 7F. Fusion of AfFtn with truncated C-terminus and POI having a protease site (TEV or FXa) in between. Both N-terminus His-tag and C-terminus c-Myc epitope are highlighted [h6NE-POI-protease]. Both the constructs FIGS. 7E and 7F were cloned in pBAD/HisB vector.

FIG. 8A. Wild type with negative interior surface. FIG. 8B. AfFtnΔC(+) with positive interior surface. A total of 48 mutations (four per subunit: E65K, E128K, E131K, and D138A) are highlighted. FIG. 8C. AfFtnΔC(+/−) with neutral interior surface. A total of 24 mutations (two per subunit: E65Q and D138A) are highlighted. For the sake of visual clarity, 12 subunits are removed to show the interior of the shell.

FIGS. 9A-9F show characteristics of engineered AfFtn cages. FIGS. 9A, 9B, 9C, 9D, and 9E show dynamic light scattering studies with AfFtnΔC(+), AfFtnΔC(+/−), F116HAfFtnΔC(+), F116HAfFtnΔC(+/−) and h6NE-GFP (+). FIG. 9F. SDS gel showing expression level of three engineered AfFtn cages (induced at $O.D._{600}$=0.8).

FIG. 10A shows the iron concentration of the three engineered AfFtn cages (1.6 mg/ml concentration) assayed with horse spleen ferritin as a positive control. The iron content in engineered cages was negligible when compared to the positive control. FIG. 10B shows iron uptake study of ferritin shells using ferrous ammonium sulfate. In comparison to the wild type Afu ferritin, the engineered tES shells showed lower iron uptake. All the experiments were performed at n=3, error bar represents±S.D.).

FIG. 11B. AfFtnΔC(−); FIG. 11C. AfFtnΔC(+/−)) showing intense minima at 208 nm and 224 nm and maximum at 195 nm typical of a-helical structure. The protein sample (0.1 mg/ml) was dissolved in 10 mM phosphate buffer and the measurement recorded using a Chirascan Circular Dichroism Spectrometer using a 0.1 cm path length stoppered cuvette. The heat-induced denaturation of proteins was conducted with heating protein solutions at the rate of 1° C./min, and the spectra was collected every 1° C. change.

FIG. 12A. The overall structure of AfFtn (PDB accession code 1SQ3). The helices are represented as green cylinders. The trimeric interface showing the three phenylalanine at the 116th position (magenta) has been highlighted. FIGS. 12B and 12C show chromatograms of AfFtnΔC(+) at pH 8.0 and pH 5.8, respectively. FIGS. 12D and 12E show chromatograms of F116HAfFtnΔC(+) at pH 8.0 and pH 5.8, respectively. At pH 5.8, the NE shell disassembles into its smaller subunits as denoted by peak 2. FIGS. 12F and 12G show chromatograms of h6NE-GFPuv(+) at pH 8.0 and pH 5.8, respectively. FIGS. 12H and 12I show chromatograms of F116HNE-GFPuv(+) at pH8.0 and pH 5.8, respectively. At pH 5.8, the NE shell disassembles into its smaller subunits as denoted by peak 2 and 3. Peak 2 denotes the elution of h6NE-GFPuv and peak 3 denotes the elution of NE subunits.

FIG. 13A shows 0.01% L-arabinose. FIG. 13B shows 0.1% L-arabinose. FIG. 13C shows 1% L-arabinose. A 10-mg bacterial pellet was dissolved in 1 ml lysis buffer (50 mM Tris-HCl pH 7.4, 300 mM NaCl, 0.1% Tween-20), sonicated, and centrifuged at 10,000 rpm for 20 min. The supernatant (200 µl) was taken in a 96-well black polystyrene plate and emission scan was performed from 415 to 600 nm. The excitation wavelength was fixed at 395 nm. FIG. 13D Comparison of fluorescence maxima at 509 nm among the GFPuv variants expressed at three different L-arabinose concentrations. All the experiments were performed at n=4, error bar represents±S.D.).

FIG. 16A shows effect of increasing molar concentration of tES(+)F116H subunits and FIG. 16B the charge of tESF116H subunits on native HRPC encapsulation and folding measured using HRPC activity ($OD_{450}$).+ve controls are tES(+)F116H:tES-HRPC (1 µM) and tES(−)F116H:tES-HRPC (1µM).

FIG. 17A shows size-exclusion profile of tES(+)F116H:HRPC with different molar ratios of tES(+)F116H subunits and HRPC. In all cases, the histidine-tagged subunit co-purifies with tES, indicating its encapsulation inside the tES assembly. Each fraction of the size exclusion chromatography was analyzed for its HRPC activity for all molar ratios tested FIG. 17B shows size-exclusion profile of tES(+)F116H:HRPC and tES(−)F116H:HRPC with 60:10 and 60:8 molar ratios of tES subunits and HRPC. Each fraction of the size exclusion chromatography was analyzed for its HRPC activity for all molar ratios tested which showed that tES(−)F116H was not successful in encapsulating HRPC due to net charge similarity. FIG. 17C shows thermal shift assay of tES(+)F116H:HRPC with different molar ratios of tES(+)F116H subunits and HRPC. With increasing amount of HRPC, denaturation temperature of tES(+)F116H increases. FIG. 17D shows thermal shift assay of tES(+)F116H:HRPC (60:10 molar ratio) and tES(−)F116H:HRPC (60:10 molar ratio). Negligible change in the denaturation temperature for 60:10 tES(−)F116H:HRPC indicates unsuccessful encapsulation of HRPC within tES(−)F116H as compared to tES(+)F116H.

FIG. 18A shows effect of increasing molar concentration of tES(+)F116H subunits (from 60:1 to 60:10) and FIG. 18B charge of tESF116H subunits (at 60:8 and 60:10) on native GFPuv encapsulation and folding measured using GFPuv fluorescence (508 nm). FIG. 18C shows thermal shift assay of tES(+)F116H:GFPuv with different molar ratios of tES subunits and GFPuv. With increasing amount of GFPuv, denaturation temperature of tES(+)F116H increases. FIG. 18D shows thermal shift assay of tES(+)F116H:GFPuv (60:10 molar ratio) and tES(−)F116H:GFPuv (60:10 molar ratio). Negligible change in the denaturation temperature for 60:10 tES(−)F116H:GFPuv indicates unsuccessful encapsulation of GFPuv within tES(−)F116H as compared to tES(+)F116H. In 18A+ve control is tES:tES-GFPuv (0.5 µM); −ve control is GFPuv. In 18B+ve controls are tES(+)F116H:tES-GFPuv and tES(−)F116H:tES-GFPuv.

FIG. 21A shows effect of increasing molar concentration of tES(+)F116H subunits (from 10:1 to 60:1) on encapsulation and protection of ssDNA from DNAse I digestion. Lanes marked 'B' are without DNAse I; Lanes marked 'A' are with DNAse I digestion. Lane 1 includes size markers and Lanes 2-3 are naked ssDNA controls. FIG. 21B shows Coomassie-stained gel of tES(+)F116H capsule proteins.

FIG. 22A shows tES(+)F116H forming a circular pattern (see boxed image) after addition of pRSF plasmid, strongly indicating attachment of tES(+)F116H to pRSF plasmid. tES(+)F116H and pRSF plasmid were mixed in molar ratio of 1000:1 after in vitro encapsulation of pRSF plasmid DNA by tES(+)F116H subunits, with a molar ratio in the encapsulation mixture of 1:1000. Panel on the right is an enlarged view of the left panel. FIG. 22B shows tES(+)F116H without plasmid addition. No circular patterns were observed.

DETAILED DESCRIPTION OF THE PREFERRED EMBODIMENT

A description of example embodiments of the invention follows.

Figure 1A:
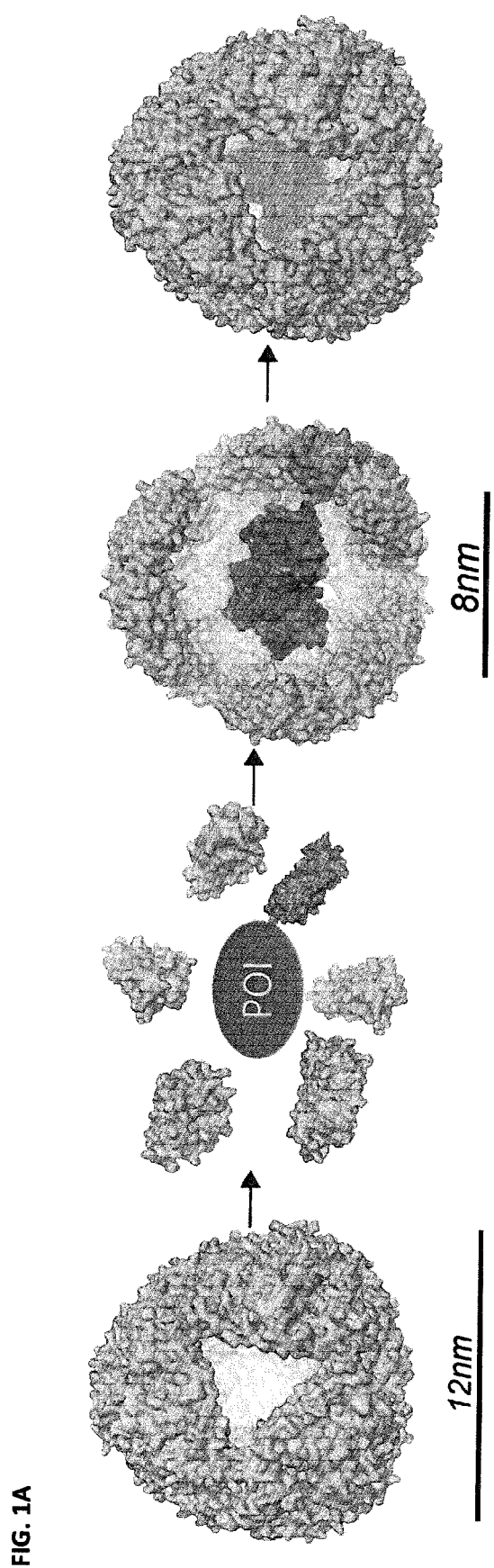
FIGS. 1A-1C show engineering of nanoencapsulator (NE) shells.

The present invention is based, in part, on the development of a method for encapsulating cargo molecules, such as nascent protein strands, nucleic acids or small molecules into engineered, aqueous cavities using nanoencapsulator shells. As described herein, the thermostable ferritin assembly from the hyperthermophilic bacterium *Archaeoglobus fulgidus* (AfFtn) was selected (FIG. 1A) to demonstrate its ability to allow diffusional accessibility to the surrounding solute and its structural stability to withstand the denaturing effect of closely associated unfolded proteins.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

Figure 1B:
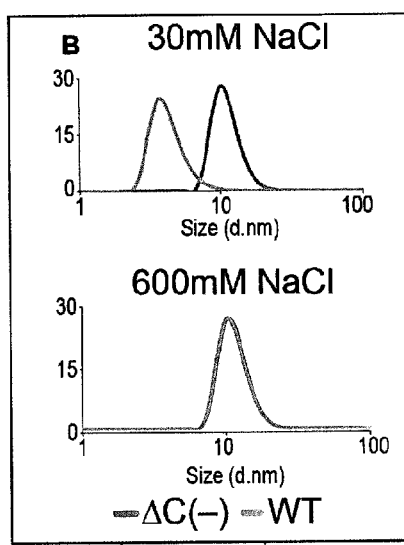

The native AfFtn assembly comprises 24 subunits, each ~20 kDa and containing a four-helix bundle structural motif. The assembly has a 12 nm external diameter and an 8 nm internal cage (Johnson, E. *Structure*. 13, 637-648 (2005)). AfFtn differs from other ferritins in that the typical octahedral (4-3-2) symmetry is exchanged for a tetrahedral (2-3) symmetry resulting in four, approximately 4.5 nm, triangular windows/pores communicating the interior with the exterior of the assembly (Sana, B. *J. Biol. Chem.* 288, 32663-32672 (2013)). The assembly is highly stable, withstanding heat up to 90° C. and urea concentrations as high as 8 M (Liu, X. *Proc. Natl. Acad. Sci. U.S.A* 100, 3653-3658 (2003)). However, the native AfFtn disassociates at low salt concentrations (Johnson, E. *Structure*. 13, 637-648 (2005)) (FIG. 1B).

Nanoencapsulators (NEs) described herein are highly stable even in low salt concentrations and engineered with net positive, neutral, or negative charged internal environments. As demonstrated herein, using NEs, the functional expression of four proteins-of-interest—green fluorescent protein, firefly luciferase, Ramilla Luciferase, and horseradish peroxidase isoenzyme C—was increased in *E. coli*. NEs described herein are also engineered to disassemble and assemble in a pH-dependent manner, which facilitated the controlled release of encapsulated proteins.

Ferritin Assembly Composition

In one aspect, provided herein is an engineered thermostable ferritin assembly comprising at least one modified ferritin subunit, wherein the at least one modified ferritin subunit lacks an unstructured carboxy-terminal sequence that a wildtype ferritin subunit possesses and wherein the assembly is stable at lower salt concentrations than the wild type ferritin assembly.

As used herein, "ferritin assembly" is used synonymously with ferritin, a known structure in the art, that comprises 24 subunits (ferritin subunits), each subunit having a defined size (e.g., ~20 kDa for AfFtn) and structural motif (e.g., a four-helix bundle structural motif for AfFtn). The native ferritin assembly has a defined external diameter (e.g., 12 nm for AfFtn) and a defined internal cage (e.g., 8 nm for AfFtn). Ferritin has been well-characterized in the art (e.g., Johnson, E. *Structure*. 13, 637-648 (2005)).

As used herein, a ferritin subunit refers, as noted above, to one of 24 subunits that form the ferritin assembly. Subunits of the ferritin assembly have a defined structure, comprising a four-helix bundle motif. In AfFtn, each subunit is ~20 kDa and contains a four-helix bundle structural motif.

As used herein, a "modified ferritin subunit" refers to a ferritin subunit that lacks an unstructured carboxy-terminal sequence that a wildtype ferritin subunit possesses. That is, the modified ferritin subunit comprises a deletion of an unstructured carboxy-terminal sequence that a wildtype ferritin subunit possesses. The modified ferritin subunit is sometimes referred to generically as "Ftn-subunitΔC" (for ferritin subunit C-deletion).

As used herein, an "engineered ferritin assembly" refers to a ferritin assembly formed with at least one modified ferritin subunit, as described herein. The engineered ferritin assembly is sometimes referred to as a "nanoshell" or "nanocage" or "nanoencapsulator" or "NE" or "thermostable exoshell" or "tES." AfFtnΔC refers specifically to the engineered *Archaeoglobus fulgidus* ferritin assembly formed with C-deletion *Archaeoglobus fulgidus* ferritin subunits.

In certain embodiments, the wildtype ferritin subunit is part of a thermostable ferritin assembly. In certain embodiments, the wildtype ferritin subunit is part of a thermostable ferritin assembly derived from hyperthermophiles such as, e.g., *Archaeoglobus fulgidus* and *Pyrococcus furiosus*. In certain embodiments, the thermostable ferritin assembly has windows/pores communicating the interior with the exterior of the assembly. In certain embodiments, the pores are about 2 nm wide to about 4.5 nm wide. In more preferred embodiments the pores are about 4.5 nm wide. In certain embodiments, the wildtype ferritin subunit comprises the sequence set forth in SEQ ID NO: 1 of AfFtn.

As used herein, an "unstructured carboxy-terminal sequence" refers to the C-terminal end stretch of residues in wildtype ferritin subunit known to have a disordered structure (e.g., does not have a helical structure). Such stretches of residues in wildtype ferritin subunits are known in the art, and those of skill in the art can identify where the unstructured region begins and ends. For example, "unstructured" sequences are generally unable to be visualized using methods such as x-ray crystallography. As another example, a residue or set of residues that obtain a b-factor of greater than 2 using molecular dynamics modeling can be identified as being "unstructured" or "disordered." In AfFtn subunits, the unstructured carboxy-terminal sequence comprises residues 165-173 (FTPPAEEEK) of SEQ ID NO: 1. In certain embodiments, the at least one modified ferritin subunit comprises residues 1-164, or 1-165, or 1-166, or 1-167, or 1-168, or 1-169, or 1-170, or 1-171, or 1-172 of SEQ ID NO: 1. An example of a modified ferritin subunit comprising residues 1-164 is set forth in SEQ ID NO: 2. As those of skill in the art would recognize, residues can be present beyond the last residue in the modified ferritin subunit that results from, e.g., cloning sites, that do not impact the engineered ferritin assembly function. For example, as shown in Table 1, AfFtn subunit with truncation of unstructured C-terminus comprise the residues "TS" that resulted from a cloning site (restriction site) in the cloning plasmid. Table 1 summarizes the sequences described herein. Removal of the unstructured carboxy-terminal sequence not only frees up space inside the engineered ferritin assembly but also imparts stability to the assembly in low salt concentrations (e.g. as low as 30 mM NaCl).

The engineered ferritin assembly could alternatively be stabilised in low salt concentrations by chemical crosslinking of subunits.

TABLE 1

Amino acid sequence of AfFtn subunits

| | |
|---|---|
| SEQ ID NO: 1 | MASISEKMVE ALNRQINAEI YSAYLYLSMA |
| AfFtn wildtype subunit | SYFDSIGLKG FSNWMRVQWQ EELMHAMKMF |
| (unstructured C-terminal | DFVSERGGRV KLYAVEEPPS EWDSPLAAFE |
| sequence underlined) | HVYEHEVNVT KRIHELVEMA MQEKDFATYN |
| | FLQWYVAEQV EEEASALDIV EKLRLIGEDK |
| | RALLFLDKEL SLRQ<u>FTPPAE EEK</u> |

TABLE 1-continued

Amino acid sequence of AfFtn subunits

SEQ ID NO: 2
AfFtn subunit with truncation
of unstructured C-terminus

MASISEKMVE ALNRQINAEI YSAYLYLSMA
SYFDSIGLKG FSNWMRVQWQ EELMHAMKMF
DFVSERGGRV KLYAVEEPPS EWDSPLAAFE
HVYEHEVNVT KRIHELVEMA MQEKDFATYN
FLQWYVAEQV EEEASALDIV EKLRLIGEDK
RALLFLDKEL SLRQTS

SEQ ID NO: 3
AfFtn net positive variant
subunit with truncation of
unstructured C-terminus MASISEKMVE ALNRQINAEI YSAYLYLSMA
SYFDSIGLKG FSNWMRVQWQ EELMHAMKMF
DFVSKRGGRV KLYAVEEPPS EWDSPLAAFE
HVYEHEVNVT KRIHELVEMA MQEKDFATYN
FLQWYVAKQV KEEASALAIV EKLRLIGEDK
RALLFLDKEL SLRQTS SEQ ID NO: 4
AfFtn net neutral variant subunit
with truncation of unstructured
C-terminus MASISEKMVE ALNRQINAEI YSAYLYLSMA
SYFDSIGLKG FSNWMRVQWQ EELMHAMKMF
DFVSQRGGRV KLYAVEEPPS EWDSPLAAFE
HVYEHEVNVT KRIHELVEMA MQEKDFATYN
FLQWYVAEQV EEEASALAIV EKLRLIGEDK
RALLFLDKEL SLRQTS

S refers to the joining of a modified ferritin subunit to a polypeptide of interest in-frame such that the modified ferritin subunit and polypeptide are linked to form a fusion, wherein the fusion does not disrupt the formation or function of the modified ferritin (e.g., its ability to assemble into a ferritin assembly) or the polypeptide. In certain embodiments, the polypeptide is fused to the carboxy-terminus of the modified ferritin subunit. Methods of engineering a fusion molecule are well known in the art.

In certain embodiments, the polypeptide is fused to the modified ferritin subunit through a joining sequence. In certain embodiments, the joining sequence is selected from any one or more of a protease recognition sequence, a linker sequence, a known epitope (e.g., Myc epitope—myc-tag derived from the corresponding c-myc gene product), a cleavage sequence, a self-cleaving sequence, a sequence enabling specific chemical modification and/or crosslinking, a sequence that results from a cloning site (e.g., restriction enzyme recognition sequence), a chemical linker or a non-covalent linker such as biotin streptavidine, or any combination thereof. A variety of suitable protease recognition sequences known in the art can be used, including, e.g., TEVprotease/FXa and/or thrombin, as described herein. A variety of linker sequences known in the art can be used, including, e.g., glycine/serine-based linkers. Methods of designing joining regions to include such sequences are well known in the art.

As used herein, "protein" and "polypeptide" are used interchangeably to denote a polymer of at least two amino acids covalently linked by an amide bond, regardless of length or post-translational modification (e.g., glycosylation or phosphorylation). The term "protein" encompasses a naturally-occurring as well as artificial (e.g., engineered or variant) full-length protein as well as a functional fragment of the protein.

The term "functional fragment" refers to a portion of a protein that retains some or all of the activity or function (e.g., biological activity or function, such as enzymatic activity) of the full-length protein, such as, e.g., the ability to bind and/or interact with or modulate another protein or nucleic acid. The functional fragment can be any size, provided that the fragment retains, e.g., the ability to bind and interact with another protein or nucleic acid.

As described herein, the polypeptide is encapsulated in the engineered ferritin assembly. That is, the modified ferritin subunits, when forming the engineered ferritin assembly, form a cage that surrounds the polypeptide. In certain embodiments, a modified ferritin subunit that is fused to a polypeptide will assemble with other non-fused modified ferritin subunits to form an engineered ferritin assembly that encapsulates the polypeptide. In certain embodiments, one modified ferritin subunit that is fused to a polypeptide will assemble with 23 other non-fused modified ferritin subunits to form an engineered ferritin assembly that encapsulates one polypeptide.

As described herein, the engineered ferritin assembly can be designed for controlled release of the encapsulated polypeptide. In certain embodiments, the modified ferritin subunit comprises a substitution at position F116 of SEQ ID NO: 1 of AfFtn, or a substitution at an equivalent position in a non-AfFtn ferritin subunit. In certain embodiments, the at least one modified ferritin subunit comprises the substitution F116H; an example of which is set forth in SEQ ID NO: 5. An engineered ferritin assembly with F116H mutation is shown herein to reversibly dissociate at acidic pH (i.e. below pH 7.0), preferably from about pH 4.0, more preferably at about pH 5.8, and stably reassemble at basic pH (i.e. above pH 7.0), preferably at about pH 8.0.

In certain embodiments, the at least one modified ferritin subunit comprises the substitution F116H and a net positive internal charge; an example of which is set forth in SEQ ID NO: 8.

In certain embodiments, a substitution at F116 renders the engineered ferritin assembly susceptible to assembly and/or disassembly dependent on a covalently bound modifier.

Methods of Using the Engineered Ferritin Assembly

In one aspect, the engineered ferritin assembly described herein is used in a method of enhancing expression of a polypeptide. The method of encapsulating a polypeptide comprises introducing into a cell a nucleic acid comprising: a) first sequence that encodes a modified ferritin subunit lacking an unstructured carboxy-terminal sequence that a wildtype ferritin subunit possesses; and b) a second sequence that encodes a modified ferritin subunit lacking an unstructured carboxy-terminal sequence that a wildtype ferritin subunit possesses fused to a polypeptide. That is, the first sequence encodes a modified ferritin subunit that comprises a deletion of an unstructured carboxy-terminal sequence that a wildtype ferritin subunit possesses (referred to as Ftn-subunitΔC), whereas the second sequence encodes a fusion of a modified ferritin subunit that comprises a deletion of an unstructured carboxy-terminal sequence that a wildtype ferritin subunit possesses, and a polypeptide, as described herein. The method further comprises expressing the first and second sequences and forming a ferritin assembly that encapsulates the polypeptide, thereby enhancing the expression of the polypeptide.

In certain embodiments, the wildtype ferritin subunit comprises the sequence set forth in SEQ ID NO: 1. In certain embodiments, the modified ferritin subunit comprises the sequence set forth in any one of the group comprising SEQ ID NO: 2, SEQ ID NO: 3, SEQ ID NO: 4, SEQ ID NO: 5 and SEQ ID NO: 8.

The engineered ferritin assemblies described herein enable efficient folding of a polypeptide to increase overall production of a functional polypeptide. The engineered ferritin assembly provides an optimal environment that enhances folding of an encapsulated polypeptide to a functional structure. The engineered ferritin assembly prevents or minimizes misfolding and/or aggregation that would otherwise occur in the polypeptide if expressed without encapsulation by the engineered ferritin assembly. Thus, as used herein, "enhancing expression" refers to enhanced folding, reduced aggregation, increased expression, or other processes, or a combination thereof, that result in an increased production of a functional polypeptide (e.g., a polypeptide that performs its intended biological function).

As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In certain embodiments, nucleic acid molecules can be modified. In the case of a double-stranded polymer, "nucleic acid" can refer to either or both strands of the molecule.

As described herein, a nucleic acid can be encapsulated in the engineered ferritin assembly. That is, the modified ferritin subunits, when forming the engineered ferritin assembly, form a cage that surrounds the nucleic acid. In certain embodiments the at least one modified ferritin subunit is fused to a nucleic acid. In certain embodiments, the engineered ferritin assembly described herein can provide resistance of an encapsulated nucleic acid to degradation. It would be understood that methods of chemical cross-linking between nucleic acid and protein are well known.

As described herein, a small molecule may be encapsulated in the engineered ferritin assembly. That is, modified ferritin subunits in a sample, when forming the engineered ferritin assembly, form a cage that surrounds one or more small molecules present in the sample. In certain embodiments, the engineered ferritin assembly described herein can increase the resistance of an encapsulated small molecule to degradation and/or provide controlled release of same.

In certain embodiments, the encapsulated polypeptide or nucleic acid has increased resistance to denaturation compared to when said polypeptide or nucleic acid is unencapsulated.

The term "nucleotide sequence," in reference to a nucleic acid, refers to a contiguous series of nucleotides that are joined by covalent linkages, such as phosphorus linkages (e.g., phosphodiester, alkyl and aryl-phosphonate, phosphorothioate, phosphotriester bonds), and/or non-phosphorus linkages (e.g., peptide and/or sulfamate bonds). In certain embodiments, the nucleotide sequence encoding, e.g., a target-binding molecule linked to a localizing domain is a heterologous sequence (e.g., a gene that is of a different species or cell type origin).

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As will be appreciated by those of skill in the art, in certain embodiments, the nucleic acid further comprises a plasmid sequence. The plasmid sequence can include, for example, one or more sequences of a promoter sequence, a selection marker sequence, or a locus-targeting sequence. Methods of introducing nucleic acid compositions into cells are well known in the art.

In certain embodiments, the nucleic acid is introduced into a cell in vitro. In certain embodiments, the nucleic acid is introduced into a cell in vivo (e.g., in organs of genetically modified and/or virus-transformed animals; cells in the context of the whole insect).

In certain embodiments, the cell is a bacterial cell, a plant cell, a mammalian cell, or an insect cell.

In certain embodiments, the first and second sequences are introduced into the cell on separate plasmids. A variety of suitable plasmids are readily available and known in the art. In certain embodiments, the first and second sequences are introduced into the cell on a single plasmid, wherein the first and second sequences are expressed under separate promoters.

In certain embodiments, there is provided an isolated plasmid or vector nucleic acid comprising
a) a sequence that encodes a modified ferritin subunit lacking an unstructured carboxy-terminal sequence that a wildtype ferritin subunit possesses; and/or
b) a sequence that encodes a modified ferritin subunit, lacking an unstructured carboxy-terminal sequence that a wildtype ferritin subunit possesses, fused to a polypeptide.

In certain embodiments, the isolated plasmid or vector encodes at least one modified ferritin subunit according to any aspect of the invention. In certain embodiments, the isolated plasmid or vector encodes at least one modified ferritin subunit comprising the sequence set forth in any one of the group comprising SEQ ID NO: 2, SEQ ID NO: 3, SEQ ID NO: 4, SEQ ID NO: 5 and SEQ ID NO: 8.

In certain embodiments, the first sequence is expressed in excess of the second sequence. For example, the first and second sequences are expressed at a ratio of (first:second) about 23:1, about 11:1, about 7:1, about 5:1, about 19:5, about 3:1, about 17:7, about 2:1, about 5:3, about 7:5, about 13:11, or about 1:1. Thus, the non-fused modified ferritin subunit is usually expressed in excess of the modified ferritin subunit that is fused to a polypeptide. As would be appreciated by those of skill in the art, the ratio will vary depending on a number of factors, including, e.g., the characteristics of the fused polypeptide (e.g., polypeptide size). Thus, more than one polypeptide can be encapsulated in an engineered ferritin assembly. In certain embodiments, one polypeptide is encapsulated in an engineered ferritin assembly (e.g., resulting from the assembly of first:second ratio of about 23:1).

As described herein, the engineered ferritin assembly comprises at least one modified ferritin subunit that comprises a deletion of an unstructured carboxy-terminal sequence that a wildtype ferritin subunit possesses. Thus, those skilled in the art would appreciate that an engineered ferritin assembly can be formed by modified ferritin subunits of varying lengths (e.g., a modified ferritin subunit comprising residues 1-164, 1-165, 1-166, 1-167, 1-168, 1-169, 1-170, 1-171, or 1-172 of SEQ ID NO: 1). In certain embodiments, the engineered ferritin assembly is formed by modified ferritin subunits of uniform length, with the exception of the modified ferritin subunit that is fused to a polypeptide, which comprises extra residues associated with the polypeptide and any joining sequences. For example, an engineered ferritin assembly can be formed using 23 subunits that comprise residues 1-164 of SEQ ID NO: 1 without a fusion to a polypeptide, and 1 subunit that comprises residues 1-164 of SEQ ID NO: 1 fused to a polypeptide, as described herein. It has been shown herein that cellular production of encapsulated polypeptide (P01) requires linkage of the polypeptide to a modified ferritin subunit.

The ability of tES to aid in vitro folding of proteins was tested. The tES(+)F116H assembly was highly stable at pH 8.0, as evidenced by similar elution profiles on SEC after treatment with 8 M urea or 6 M guanidinium hydrochloride (GuHCl), compared with PBS controls. Likewise, tES(+)F116H can reversibly associate and dissociate with pH titration with no observable precipitates. We then hypothesized tES could functionally encapsulate substrate proteins under conditions that would denature the POI. tES fusion proteins express as inclusion bodies in the absence of co-expressed tES. Thus, using tES(+)F116H, we tested ratios of tES to tES-POI, using a pH shift from 5.8 to 8.0 to induce assembly of the shell. The addition of tES(+)F116H to tES-GFPuv resulted in a ~100-fold increase in functional yield, which was maximum at a 90:1 ratio of tES(+)F116H subunits to tES-GFPuv. In certain embodiments, in vitro encapsulation and folding is achieved with a molar ratio of tES(+)F116H: tES-POI of at least 20:1, at least 30:1, at least 40:1, at least 50:1, at least 60:1, at least 70:1, at least 80:1, at least 90:1.

It has also advantageously been shown herein that it is possible to encapsulate a polypeptide (P01) or nucleic acid within an engineered ferritin assembly in a cell-free system without the need of a linker to attach the POI or nucleic acid to a tES subunit. However, for efficient encapsulation more POI relative to tES is required than when the POI is linked to a tES subunit. In certain embodiments, the ferritin assembly comprises tESF116H subunits. In certain embodiments the ferritin assembly comprises tES(+)F116H subunits. In certain embodiments, the tESF116H subunits comprises the sequence set forth in SEQ ID NO: 5 or SEQ ID NO: 8. In certain embodiments, the tESF116H subunits are admixed and co-incubated with the POI at an acidic pH, (i.e. below pH 7.0), preferably from about pH 4.0, more preferably at about 5.8, and then the pH of the mixture is adjusted to basic pH (i.e. above pH 7.0), preferably to about pH 8 to drive ferritin assembly and encapsulation of the POI. In certain embodiments, the tESF116H subunits are admixed in excess of the POI. For example, the tESF116H subunits and POI molecules are admixed at a molar ratio of at least 60:1, at least 60:3, at least 60:5, at least 60:8, at least 60:10, at least 60:12, at least 60:15, at least 60:30, or any suitable ratio.

In certain embodiments, the method further comprises isolating the ferritin assembly that encapsulates the polypeptide, as described herein. In certain embodiments, the method further comprises isolating the polypeptide, as described herein (e.g., cleaving the fusion joining sequence to separate the polypeptide from the modified ferritin subunit).

In another aspect, the engineered ferritin assembly described herein is used in a method of delivering a polypeptide into a cell by delivering an engineered ferritin assembly that encapsulates a polypeptide to a cell. The method of delivering an engineered ferritin assembly into a cell comprises contacting the cell with an engineered ferritin assembly that comprises at least one modified ferritin subunit, wherein the modified ferritin subunit lacks an unstructured carboxy-terminal sequence that a wildtype ferritin subunit possesses, and wherein the at least one modified ferritin subunit is fused to a polypeptide. As described herein, the engineered ferritin assembly encapsulates the polypeptide.

In certain embodiments, the cell is a diseased cell. In certain embodiments, the diseased cell is, e.g., a diseased heart cell, a diseased liver cell, a diseased neuron, or a diseased immune cell. In certain embodiments, the diseased cell is a cancer cell.

In certain embodiments, the engineered ferritin assembly comprises a cell targeting moiety, e.g., on the surface of the engineered ferritin assembly. In certain embodiments, the cell targeting moiety binds to a molecule (e.g., a receptor or a ligand) on the diseased cell. Examples of molecules bound by a cell targeting moiety include, e.g., EGFR and cell adhesion molecules (e.g., integrins and organ level selectivity such as the enhanced permeability and retention (EPR) effect).

As those skilled in the art would appreciate, a variety of molecules (e.g., peptides, receptors, ligands, and fragments thereof) can be used as a targeting moiety to target and bind to a molecule on a diseased cell. In certain embodiments, the cell targeting moiety is a peptide comprising the amino acid sequence set forth in SEQ ID NO: 6 (YHWYGYTPQNVI) or SEQ ID NO: 7 (LARLLT).

In certain embodiments, the targeting moiety is cross-linked to the ferritin assembly surface. Methods of cross-linking molecules (e.g., peptides) with other molecules are known in the art. For example, as described herein, cross-linking agents, e.g., sulfo-SMCC, can be used to attach a targeting moiety onto the surface of an engineered ferritin assembly.

In certain embodiments, the engineered ferritin assembly that encapsulates a polypeptide can be delivered into a cell (e.g., in vivo delivery) in a composition or formulation comprising the engineered ferritin assembly and one or more pharmaceutically acceptable carriers or excipients. Suitable pharmaceutical carriers typically will contain inert ingredients that do not interact with the agent or nucleic acid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying agents, solubilizing agents, pH buffering agents, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

The engineered ferritin assembly that encapsulates a polypeptide can be introduced into a cell as a neutral compound or as a salt or ester. Pharmaceutically acceptable salts include those formed with free amino groups such as those derived from hydrochloric, phosphoric, acetic, oxalic or tartaric acids, and those formed with free carboxyl groups such as those derived from sodium, potassium, ammonium, calcium, ferric hydroxides, isopropylamine, triethylamine, 2ethylamino ethanol, histidine, procaine, etc. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a counteraction, such as sodium or potassium.

In certain embodiments, the engineered ferritin assembly that encapsulates a polypeptide can be introduced into a cell in combination with one or more additional therapeutic agents. When administered in a combination therapy, the engineered ferritin assembly that encapsulates a polypeptide can be administered before, after or concurrently with the other therapy. When co-administered simultaneously (e.g., concurrently), the engineered ferritin assembly that encapsulates a polypeptide and other therapy can be in separate formulations or the same formulation. Alternatively, the engineered ferritin assembly that encapsulates a polypeptide and other therapy can be administered sequentially, as separate compositions, within an appropriate time frame as determined by a skilled clinician (e.g., a time sufficient to allow an overlap of the pharmaceutical effects of the therapies),In certain embodiments, the engineered ferritin assembly described herein is comprised in a composition or combination for use in the treatment of disease in a subject. In certain embodiments the disease is cancer.

In certain embodiments, an efficacious amount of the composition or combination comprising the engineered ferritin assembly is used in a method of treatment or prophylaxis of a subject in need thereof. In certain embodiments the composition or combination comprises an enzyme for conversion of a prodrug for therapy.

In certain embodiments, the composition or combination comprising the engineered ferritin assembly is a vaccine.

In another aspect of the disclosure there is provided a kit, or use of a kit, for encapsulation of a polypeptide or nucleic acid within an engineered thermostable ferritin assembly, the kit comprising at least one modified ferritin subunit according to any aspect of the invention. In a preferred embodiment the at least one modified ferritin subunit comprises a substitution at position F116 of SEQ ID NO: 1 which renders the engineered assembly capable of assembly and/or disassembly dependent on pH or covalently bound modifier.

In another aspect, the engineered ferritin assembly described herein is used in the manufacture of a medicament for the treatment of a disease in a subject. In certain embodiments, the disease is cancer.

For in vivo delivery, the engineered ferritin assembly that encapsulates a polypeptide can be delivered to a subject in need thereof by a variety of routes of administration including, for example, oral, dietary, topical, transdermal, or parenteral (e.g., intra-arterial, intravenous, intramuscular, subcutaneous injection, intradermal injection) routes of administration. Administration can be local or systemic. The actual dose of a therapeutic polypeptide encapsulated by an engineered ferritin assembly and treatment regimen can be determined by a skilled physician, taking into account the nature of the condition being treated, and patient characteristics.

As used herein, "a" or "an" may mean one or more than one unless indicated to the contrary or otherwise evident from the context.

Unless otherwise indicated or otherwise evident from the context and understanding of one of ordinary skill in the art, values that are expressed as ranges can assume any specific value or subrange within the stated ranges in various embodiments, to the tenth of the unit of the lower limit of the range, unless the context clearly dictates otherwise. "About" in reference to a numerical value generally refers to a range of values that fall within ±10%, in some embodiments ±5%, in some embodiments ±1%, in some embodiments ±0.5% of the value unless otherwise stated or otherwise evident from the context. In any embodiment in which a numerical value is prefaced by "about", an embodiment in which the exact value is recited is provided. Where an embodiment in which a numerical value is not prefaced by "about" is provided, an embodiment in which the value is prefaced by "about" is also provided. Where a range is preceded by "about", embodiments are provided in which "about" applies to the lower limit and to the upper limit of the range or to either the lower or the upper limit, unless the context clearly dictates otherwise. Where a phrase such as "at least", "up to", "no more than", or similar phrases, precedes a series of numbers, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1: Materials and Methods

Plasmids and Competent Cells

The pRSF1b expression vector (Merck) and pBAD/HisB (Life Technologies) were used for cloning. Chemically competent XL1 Blue E. coli cells (Simply Science) and BL21(DE3) E. coli cells (Simply Science) were used for transformation.

Reagents and Antibodies

The following reagents were used: restrictions enzymes NcoI, EagI, and SpeI (New England BioLabs), Expresslink T4 DNA ligase (Life Technologies), Luria-Bertani (LB) agar (Axil Scientific), kanamycin (ThermoFisher), ampicillin (Axil Scientific), Omega bio-tek plasmid mini kit and gel extraction kit (Simply Science), Q5® Site-Directed Mutagenesis Kit (New England BioLabs), isopropyl β-D-1-thiogalactopyranoside, IPTG (Axil Scientific), L-arabinose (Sigma), Tris-HCl pH8.0 (Sigma), sodium chloride, NaCl (Sigma), Triton-X 100 (Sigma), calcium chloride, $CaCl_2$ (Sigma), hemin (Sigma), β-mercaptoethanol (Sigma), imidazole (Sigma), L-glutathione oxidized (Sigma), nitric acid (Merck), bathophenanthroline disulfonic acid (Sigma), dithionite (Sigma), phosphate buffered saline, PBS (Sigma), Tween-20 (ThermoFisher), chemiluminescent HRP substrate (Millipore), 3,3',5,5'-Tetramethylbenzidine, TMB substrate (ThermoFisher), sulfuric acid, $H_2SO_4$ (Sigma), D-luciferin potassium salt (ThermoFisher), magnesium chloride, $MgCl_2$ (Sigma), blotting-grade blocker (Bio-Rad), ethylenediaminetetraacetic acid, EDTA (Sigma), adenosine triphosphate, ATP (ThermoFisher), bovine serum albumin, BSA (ThermoFisher), recombinant luciferase (ThermoFisher), bovine FXa (Axil Scientific), TEVprotease (Sigma), Thermo Scientific™ Pierce™ c-Myc Tag IP/Co-IP Kit (cat. No. 23620). The following antibodies were used: c-Myc (9E10) HRP mouse monoclonal IgG1 (Axil Scientific), His-probe (H-3) HRP mouse monoclonal IgG1 (Axil Scientific), rabbit monoclonal GFP antibody (Life Technologies), HRP-conjugated anti-rabbit IgG antibody (Life Technologies), and firefly luciferase goat polyclonal antibody HRP conjugated (Abcam).

Cloning

The AfFtn gene was selected based on the sequence in GenBank AF_RS04235. The gene with mutations for C-terminus truncation as well as altered charges was synthesized from GenScript. The mutated gene was digested using NcoI and SpeI restriction enzymes and cloned into pRSF1b expression vector using Expresslink T4 DNA ligase. The ligation reaction was transformed into chemically competent XL1 Blue E. coli cells and cultured on LB agar plate with 50 mg/mi kanamycin. Plasmid DNA was isolated by Omega bio-tek plasmid mini kit and gel extraction kit and the sequence confirmed by nucleic acid sequencing. The engineered AfFtn gene was used to create F116H mutation using Q5® Site-Directed Mutagenesis Kit. The genes for POI's: GFPuv (based on the wild type GFP sequence P42212 with three mutations F99S, M153T, and V163A), HRPC (P00433), and luciferase (P08659) were synthesized from Genscript, digested using SpeI and EagI restriction enzymes, and the resulting fragments were ligated with pBAD/HisB using Expresslink T4 DNA ligase. The gene for engineered AfFtn was ligated into the pBAD/HisB containing the gene for POI. The ligation reaction was transformed into chemically competent XL1 Blue E. coli cells. The plasmid DNA was isolated and sequenced. For co-expression, the pRSF1b (with a T7 promoter plasmid and a complementary RSF origin of replication) and pBAD/HisB (with an L-arabinose promoter and a pBR322 origin of replication) constructs were co-transformed into BL21(DE3) *E. coli* cells and grown on LB agar plates with 50 mg/ml kanamycin and 100 mg/ml ampicillin. Shell components induced in isolation were well expressed accounting for up to 50% of all the protein in *E. coli* lysate. The protease site (TEVprotease/FXa) was incorporated between the 6×His-engineered AfFtn and POI gene using Q5® Site-Directed Mutagenesis Kit.

Protein Expression and Purification

A single positive colony was selected from a freshly transformed plate and grown in 15 ml LB broth overnight at 37° C. Ampicillin (100 mg/ml) and kanamycin (50 mg/ml) were used for expression of single plasmid constructs pBAD/HisB and pRSF1b, respectively. For double transformed constructs both the antibiotics were used. A 500 ml volume of LB broth was inoculated with 12.5 ml of the starter culture and allowed to grow until an absorbance (O.D.$_{600}$) of 0.4-0.5 was reached. Protein expression was induced with either 0.5 mM IPTG (for pRSF1b constructs) or 0.1% L-arabinose (for pBAD/HisB constructs) or both (for double transformed constructs). To test the role of tightly controlled relative expression of the encapsulated POI, using GFPuv we evaluated the effect of L-arabinose (0.001%, 0.01%, 0.1%, and 1%) on the functional expression of POI. After 4h incubation at 37° C., cells were pelleted by centrifugation at 10,000 rpm for 10 mins. The cell pellet was resuspended in a lysis buffer (for GFP and luciferase, 25 mM Tris-HCl pH 8.0, 300 mM NaCl, 0.1% Triton X-100; for HRP, 25 mM Tris-HCl pH 8.0, 300 mM NaCl, 5 mM CaCl2, 2.5 µM hemin, 10 mM β-mercaptoethanol), sonicated, and centrifuged to separate cell debris. The supernatant obtained was injected on to a Ni2+-nitriloacetic acid-agarose (Expedeon) column equilibrated with a buffer containing 25 mM phosphate pH 8.0, 300 mM NaCl. The bound protein was eluted with elution buffer containing 25 mM phosphate pH 8, 300 mM NaCl, 250 mM imidazole. The eluted protein was concentrated and further purified through size exclusion chromatography (SEC) using Superdex S-200 10/300 GL column (GE healthcare) and buffer containing 25 mM Tris-HCl pH 8.0, 5 mM CaCl$_2$, 0.3 mM L-glutathione oxidized for HRP and 25 mM Tris-HCl pH 8.0 for GFP and luciferase. The purity of the SEC fraction was analyzed using SDS-PAGE.

Protein Expression in *E. coli*

For the expression of each clone, a single positive colony was selected from a freshly transformed plate and grown in 100 mL LB broth, with kanamycin (50 pg/mL, for protein gene on pRSF1b vector), ampicillin (100 pg/mL, for protein gene on pBAD/HisB vector), or both (co-transformation) used as selection markers. Following overnight incubation at 37° C., 12.5 mL of the starter culture was used to inoculate 500 mL LB broth and allowed to grow until an absorbance (OD600) of 0.4-0.5 was reached. Protein expression was then induced with 0.4 mM IPTG (pRSF vector), 0.1% L-arabinose (pBAD vector), or both (co-transformation). We tested the role of tightly controlled relative expression of the encapsulated POI by evaluating the effect of L-arabinose (0.01%, 0.1%, and 1%) on the functional expression of GFPuv. After 4 h incubation at 37° C., cells were pelleted by centrifugation at 13,750×g for 10 min. The cell pellet was resuspended in lysis buffer (25 mM Tris-HCl, 150 mM NaCl, pH 7.5), sonicated, and centrifuged to separate cell debris. The supernatant obtained was purified using a two-step chromatography procedure. pRSF clones were subjected to hydrophobic interaction chromatography (HIC) using HiPrep™ Phenyl FF (low sub) 16/10 (GE healthcare), followed by SEC using a Superdex S-200 10/300 GL column (GE healthcare). pBAD clones were subjected to Ni-NTA (Expedeon) column chromatography, followed by SEC. Fusion proteins were purified using Ni-NTA and SEC. The purity of the SEC fraction was analyzed using sodium dodecyl sulfate polyacrylamide gel electrophoresis (SDS-PAGE). Buffers used were as follows: HIC: buffer A, 25 mM Tris-HCl, 150 mM NaCl, 1 M (NH$_4$)$_2$SO$_4$, pH 7.5; buffer B, 25 mM Tris-HCl, 150 mM NaCl, pH 7.5; Ni-NTA chromatography: buffer A, 25 mM Tris-HCl, 150 mM NaCl, pH 7.5; buffer B, 25 mM Tris-HCl, 150 mM NaCl, 500 mM imidazole, pH 7.5; SEC: 25 mM Tris-HCl, pH 8; All buffers used for the lysis, purification, and assays of HRPC clones were supplemented with 5 mM CaCl$_2$ and 2.5 µM hemin (a stock solution of 40 mM was prepared by dissolving 25 mg hemin in 1 mL 1.4 N ammonium hydroxide).

Inclusion Body POI Expression, Solubilization, and Purification

Following expression of each POI, cells were pelleted by centrifugation at 10,000 rpm for 10 min. The cell pellet was resuspended in a lysis buffer (1.5% Triton X-100, 25 mM Tris-HCl, 150 mM NaCl, pH 7.5-8), sonicated, and centrifuged to separate cell pellet. The cell pellet was resuspended in washing buffers (0.5% Triton X-100, 25 mM Tris-HCl, 200 mM NaCl, pH 8 and 25 mM Tris-HCl, 0.5 M NaCl, 2 M urea, pH 8) and centrifuged to separate cell pellet. The pellet was resuspended in solubilization buffer (25 mM Tris-HCl, 6 M GuHCl, 0.5 M NaCl, pH 8) to solubilize inclusion bodies, followed by centrifugation at 10,000 rpm for 20 min for the separation of cell debris. The supernatant obtained was purified using Ni2+-NTA column equilibrated with buffer A. The bound protein was eluted with buffer B. The purity of the eluted fraction was analyzed using SDS-PAGE.

For tES, the supernatant was purified using a two-step chromatography procedure. pRSF clones were subjected to hydrophobic interaction chromatography (HIC) using HiPrep™ Phenyl FF (low sub) 16/10 (GE Healthcare), followed by SEC using a Superdex S-200 10/300 GL column (GE Healthcare). pBAD clones were subjected to Ni-NTA (Expedeon) column chromatography, followed by SEC. Fusion proteins were purified using Ni-NTA and SEC. The purity of the SEC fraction was analyzed using sodium dodecyl sulfate polyacrylamide gel electrophoresis (SDS-PAGE). Buffers used were as follows:

HIC: buffer A, 25 mM Tris-HCl, 150 mM NaCl, 1 M (NH4)2SO4, pH 7.5; buffer B, 25 mM Tris-HCl, 150 mM NaCl, pH 7.5.

Ni-NTA chromatography: buffer A, 25 mM Tris-HCl, 150 mM NaCl, pH 7.5; buffer B, 25 mM Tris-HCl, 150 mM NaCl, 500 mM imidazole, pH 7.5.

SEC: 25 mM Tris-HCl, pH 8.

All buffers used for the lysis, purification, and assays of HRPC clones were supplemented with 5 mM CaCl$_2$) and 2.5 µM hemin (a stock solution of 40 mM was prepared by dissolving 25 mg hemin in 1 mL 1.4 N ammonium hydroxide).

Protein Concentration, Iron Assay, and Size Determination

Protein concentration was determined using Beer-Lambert's equation by measuring the absorbance at 280 nm using Nanodrop (DeNovix) and molar extinction coefficient. Total iron content in the engineered NEs was determined spectrophotometrically (Sana, B. et al., *J. Biol. Chem.* 288, 32663-32672 (2013)). Briefly, the protein samples were denatured by treating with 50 mM nitric acid and mixed with 10 mM bathophenanthroline disulfonic acid, 20 mM dithionite, and 250 mM Tris buffer, pH 8.0. The mixture was incubated overnight and iron concentration measured from the absorbance of the complex at 538 nm (€538=22.1 mM-1 cm-1). Particle size measurements of engineered NEs and WT AfFtn were conducted by dynamic light scattering (DLS) technique using a zetasizer (Nano-ZS90, Malvern) in disposable cuvettes, and average hydrodynamic diameter was determined by taking an arithmetic average of 10 runs. The measurements were done with 100 µM protein concentration at 25° C.

Western Blot Analysis

Samples (purified protein or cell lysate) were resolved on 12% SDS gel and transferred on to nitrocellulose membrane using i blot apparatus (Life Technologies). The membrane was washed with 1×PBS, dried, and blocked overnight with 5% blotting-grade blocker in PBST (PBS with 0.05% tween-20). The block was removed and the membrane incubated with antibodies (c-Myc (9E10) HRP, mouse monoclonal IgG1 or His-probe (H-3) HRP, mouse monoclonal IgG1, 1:500 dilution). After 30-minute incubation on a rocker, the membrane was washed thrice with PBST and the protein bands detected by developing the blot with chemiluminescent HRP substrate.

Thermal Unfolding Studies

Far-UV CD spectra (260-190 nm) were recorded using a Chirascan Circular Dichroism Spectrometer (Applied Photophysics). Protein samples (0.1 mg/ml) were dissolved in 10 mM phosphate buffer and the measurements were carried out at room temperature using a 0.1 cm path length stoppered cuvette. The heat-induced denaturation of proteins was conducted by heating protein solutions at the rate of 1° C./min, and the spectra was recorded for every 1° C. change. In other tests, 0.5 µM tES(+)F116H/tES-HRPC or tES(+) F116H/tES rLuc, 50 µM HRPC, and 80 µM rLuc protein samples were incubated in an assay buffer (25 mM Tris-HCl pH-8.0) at 21.5, 37, 55, 65, and 75° C. for 15 min. Following incubation, samples were cooled down and their activities evaluated. For heat shock test, 0.5 µM tES(+)F116H/tES-rLuc and 80 µM rLuc protein samples were incubated in 25 mM Tris-HCl (pH 8) at 80° C. for 5 min, followed by cooling the protein samples at 0° C. for 5 min. The process was repeated for 5 and 10 cycles, followed by evaluation of protein activity.

Trypsin Digestion 0.5 µM tES(+)F116H/tES-HRPC or tES (+)F116H/tES-rLuc, 50 µM HRPC, and 80 µM rLuc protein samples were treated with 0.4% trypsin-EDTA solution at 37° C. for 0, 30, 60, 90, 120, and 150 min, followed by analysis of their activities.

Urea, Guanidine Hydrochloride, Acetonitrile, and Methanol Stability Tests

The effect of urea, GuHCl, ACN, and MeOH on protein stability was evaluated by treating 0.5 µM tES(+)F116H/tES HRPC or tES(+)F116H/tES-rLuc, 50 µM HRPC, and 80 µM rLuc protein samples with assay buffer (pH 8) containing 8 M urea, 6 M GuHCl, 30% ACN, and 20% MeOH, respectively, at 21.5° C. (45° C. for MeOH) for 0, 10, 20, 30, 40, and 50 min. After incubation, the protein samples were buffer exchanged with the assay buffer and their activities assessed.

In Vitro Assay Development

GFP, and HRPC and rLuc activities were determined through fluorescence, colorimetric and luminescence assays, respectively, both from cell lysate and purified proteins. For GFP, fluorescence of tES(+)F116H/tES-GFPuv, tES-GFPuv, and GFPuv was read at 508 nm in a 96-well black polystyrene plate (Fisher Scientific) with excitation wavelength fixed at 395 nm was performed or fluorescence read at 508 nm in a 96-well black polystyrene plate (Fisher Scientific) using supernatant from 10-mg bacterial pellet (induced at 0.8 OD and cultured for 24h). The activity of tES(+)F116H/tES-HRPC, tES-HRPC, and HRPC was assayed using TMB substrate in a 96-well crystal-clear polystyrene plate (Greiner Bio-One). Briefly, fractions were incubated in assay buffer containing 25 mM Tris-HCl pH-8.0, 5 mM $CaCl_2$, 2.5 µM hemin for 5 mins. The TMB substrate was added for color development and the reaction stopped using 2M $H_2SO_4$ after 5 mins. Absorbance was recorded at 450 nm. All luciferase reactions took place at ambient temperature (24-27° C.) in a 96-well plate with white interior and were performed at least in triplicates. Following chromatographic purification, equimolar concentrations (500 nM) of purified h6NE-luciferase(+), h6NEluciferase(-), and h6NE-luciferase(+/-) were evaluated for luciferase activity using D-luciferin potassium salt as a substrate. The reaction was initiated by injecting 50µl buffer containing D-luciferin potassium salt (final concentration 200 µM), 50 mM Tris-Cl pH 7.5, 10 mM $MgCl_2$, 2 mM EDTA, 100 µM ATP, 0.1% BSA, to a 50µl protein sample. Purified tES(+)F116H/tES-rLuc, tES-rLuc, and rLuc were evaluated using *Renilla* luciferase kit (Promega) with some modifications in the manufacturer's instructions. The reaction was initiated by injecting 50 µL *Renilla* luciferase assay reagent (1:1,000 dilution of coelentrazine in the assay buffer). The signal was integrated for 1 min with a 2 s delay and luminescence was measured in Relative Light Units (RLU). Luciferin-containing buffer was protected from light at all time by covering the tubes with an aluminum foil. Recombinant luciferase (10 nM) and AfFtnΔC(-) were used as positive and negative controls, respectively. For enzyme kinetic studies, reactions were carried out in buffer containing 50 mM Tris-Cl pH 7.5, 10 mM $MgCl_2$, 2 mM EDTA, 100 µM ATP, 0.1% BSA. The steady-state initial velocities, VO, (RLU/sec) for h6NE-luciferase(+/-) and recombinant luciferase were determined by initiating the reaction with different concentration of D-luciferin potassium salt. The signal was integrated for 1 min with a 2 second delay and was reported in RLU. To calculate the Michaelis constant, Km, Graphpad software package (GraphPad Prism 5.01 for Windows) was used. All readings were recorded on a Perkin Elmer Plate reader. The experiments were repeated in triplicates and results were presented as mean±SEM (n=3). Appropriate controls were used in each case to minimize background.

Cage Break Study and Release of Functional Protein

Engineered pH-responsive NEF116H shells containing the POI—GFP, rLuc and HRP—were purified as described earlier. The purified protein was acidified for cage disassembly in 25 mM Tris-citrate buffer, pH 5.8 for 30 mins. The sample was subjected to SEC (Superdex S-200, 10/300 GL column) using 25 mM Tris-citrate buffer pH 5.8, followed by SDS-PAGE analysis. GFP, rLuc and HRP activity of each fraction was analyzed as described earlier. The release of the functional POI from the NE subunit was studied by cleavage with bovine FXa/TEV protease. Briefly, the cage break fraction corresponding to the elution of h6NE-POI on SEC was subjected to FXa cleavage at 37° C. for 4h (TEV cleavage at 34° C. for 5 h). The reaction mixture was run on an SDS gel and the separated POI bands were analyzed through western blot.

In Vitro Folding of Fused POI in tES(+)F116H Shells

The POI sample (1 µM) was heated at 60° C. for 30 min, followed by its pH adjustment to 5.8 using 6 M GuHCl. The POI was incubated in presence of tES(+) subunits (in 25 mM Tris-HCl), with the subunit to POI ratio of 90:1, 60:1, 30:1, 20:1, 10:1, and 0:1. The pH of the mixture was adjusted to 8 and sample incubated at room temperature for 30 min. The mixture was dialyzed in a refolding buffer (25 mM Tris-HCl, 150 mM NaCl, pH 8; HRPC: 25 mM Tris-HCl, 0.6 M GuHCl, 0.35 mM oxidized glutathione, 0.044 mM DTT, 7% glycerol, 5 mM $CaCl_2$), 20 µM heme, pH 8.5) using Slide-A-Lyzer® Dialysis Cassette G2 (Thermo Scientific). The refolded protein was purified using Ni-NTA chromatography, followed by SEC as described above. Fractions around the eluted peak were collected and their activity analyzed to identify fractions containing the POI.

Cell-Free Encapsulation of Un-Fused POI in tESF116H Shells

Inclusion body purification protocol is same as herein described. The P01 sample (HRPC, GFPuv or rLuc (*Renilla* Luciferase; a 36 kDa protein from sea pansy, *Renilla reniformis*) was heated at 60° C. for 30 min, followed by its pH adjustment to 5.8 using 6 M GuHCl. The P01 was incubated in presence of tES(+)F116H subunits (in 25 mM Tris-HCl), with the subunit to P01 ratio of 60:15, 60:12, 60:10, 60:8, 60:5, 60:3 and 60:1. The P01 was also incubated in presence of tES(−)F116H subunits (in 25 mM Tris-HCl), with the subunit to P01 ratio of 60:10 and 60:8. The pH of the mixture was adjusted to 8 and sample incubated at room temperature for 30 min. The mixture was dialyzed in a refolding buffer (25 mM Tris-HCl, 150 mM NaCl, pH 8; HRPC: 25 mM Tris-HCl, 0.6 M GuHCl, 0.35 mM oxidized glutathione, 0.044 mM DTT, 7% glycerol, 5 mM $CaCl_2$, 20 µM heme, pH 8.5) using Slide-A-Lyzer® Dialysis Cassette G2 (Thermo Scientific). The refolded protein was purified using size exclusion chromatography as described above. Fractions around the eluted peak were collected and their activity analyzed to identify fractions containing the POI.

Cell-Free Encapsulation of Un-Fused Nucleic Acid in tESF116H Shells

For ssDNA encapsulation, 110 nM of ssDNA (Primer sequence—5'/5Phos/TAT GCT GGC GGG CCC GCA GAT GCA TGG TAC TAG TTC CAT GGT GGT GAA AAT TTG CGG CAT TAA AAG CCT GGA AGA ACT GGA AAT TGT GGA AAA ACA TG-3') was incubated with tES(+)F116H subunits (in 25 mM Tris-HCl, pH 5.8), with a ssDNA to tES(+)F116H molar ratio of 1:10, 1:20, 1:30, 1:40, 1:50 and 1:60. The pH of the mixture was adjusted to 8 and the sample incubated at 4° C. for 30 min, after which it was stored on ice until use. Reassembled tES(+)F116H with ssDNA was treated with 2 units of DNase I (obtained from New England Biolabs) at 37° C. for 15 min, followed by the addition of 50 mM EDTA (to a final concentration of 5 mM) to stop the reaction. An identical amount of naked ssDNA was used as control. All samples were then incubated with DNA-loading buffer and loaded onto a 2% agarose gel. After imaging for ssDNA, the same gel was incubated with Coomassie blue solution to detect shell proteins.

For plasmid encapsulation, pRSF plasmid was incubated with tES(+)F116H subunits (in 25 mM Tris-HCl, pH 5.8), with a ssDNA to tES(+)F116H molar ratio of 1:1000. The pH of the mixture was adjusted to 8 and the sample incubated at 4° C. for 30 min, after which it was stored on ice until use. An identical amount of tES(+)F116H was used as control. Both the samples were viewed under Transmission Electron Microscope (TEM).

Internalization of POI

ELISA-based epitope protection assay, TEV protease assay, and Co-Immunoprecipitation using anti-c-Myc antibody were performed to study the internalization of POI within the NE shells.

Gluteraldehyde-Crosslinking of tES(+)F116H Shells

Glutaraldehyde (1%, 0.5%, 0.1% or 0.05%) was added to purified tES(+)F116H in PBS buffer, pH 7.4 (tES(+)F116H concentration: 5 mg/ml) and the sample was incubated for 6 h at room temperature. Excess glutaraldehyde was then removed using Illustra™ NAP™ 5 column (GE Healthcare Life Sciences). tES(+)F116H was then purified by size exclusion chromatography using a Superdex™ S-200 10/300 GL column (GE healthcare) (SEC buffer-PBS, pH 7.4). 1 ml fractions were collected from 6.8 to 16.8 ml SEC eluate and analysed using SDS-PAGE.

ELISA-Based Epitope Protection Assay

Briefly, 96-well plate was coated with mouse anti-cMyc antibody (1:500 dilution in a block solution [4% BSA in 0.05% PBST]) and incubated overnight at 4° C. The plate was washed twice with PBS using a plate washer and treated with the block solution. After 1 hour, the block solution was removed and protein fractions (pH 8.0 and pH 5.8 fractions) were added for exposed antigen binding. After 5-minute incubation on a micro plate shaker at 1000 rpm at room temperature, the wells were washed thrice with PBS and the HRP activity was quantified using TMB reagent. With GFP, the bound antigen was treated with rabbit monoclonal GFP antibody (1:2000 diluted in the block solution) followed by the secondary antibody HRP-conjugated anti-rabbit IgG antibody (1:5000 diluted in block solution).

TEVprotease-Based Epitope Protection Assay

Briefly, h6NE-GFPTEV(+) and h6NE-GFPTEV were subjected to TEVprotease cleavage at 34° C. for 2h. The ratio of protease to protein was 1:2. Post incubation, the reaction mixture was separated on SDS-PAGE and the protein bands analyzed using western blot as described earlier.

Co-Immunoprecipitation Using Anti-c-Myc Antibody

The confinement of luciferase within the ferritin cage was confirmed using Thermo Scientific™ Pierce™ c-Myc Tag IP/Co-IP Kit (cat. No. 23620). Briefly, 1 µM h6NE-luciferase(+/−) was incubated with 10µl anti-c-Myc agarose slurry at 4° C. for 3 hours. Post incubation, the slurry was washed thrice with 0.05% Tween 20 (TBS-T) and the flow through collected. The anti-c-Myc bound protein was eluted by adding 30 uL elution buffer. h6NE-luciferase and AfFtnΔC (+) were used as positive and negative controls, respectively. The flow through and elute fraction for h6NE-luciferase (+/−), −AfFtnΔC(+), and h6NE-luciferase were run on 15% SDS gel. For western blot analysis, firefly luciferase goat polyclonal antibody HRP conjugated was used under standard protocol.

Surface modification of NE shell for in vitro cell targeting

Briefly, the NE shells were incubated with 10 mg/ml (final concentration) sulfo-SMCC and 10 uM (final concentration) Atto647 dye at RT for 30 mins. Both sulfo-SMCC and Atto647 are linked to the NE shell through primary amines on its surface. The sulfo-SMCC- and Atto647-tagged NE shells were purified using size exclusion chromatography to remove excess of unbound sulfo-SMCC and Atto647. The purified protein was concentrated and further incubated with either GE11 or D4 peptide (the peptide would be coupled to the surface of NE shell by forming a thioether bond between the cysteine at its C-terminus and the crosslinker sulfo-SMCC). The peptide-coupled NP shells were separated by size exclusion chromatography. Both GE11 and D4 peptides are known to bind epidermal growth factor receptor (EGFR) without significant mytogenic activity (Zarschler, et al., *Nanoscale* 6:6046-6056 (2014)). EGFR is overexpressed on cancer cells and is considered as an efficient targeting moiety selective to tumor sites (Konho, et al., *Eur J Cancer.* 47:773-783 (2011)).

Cell Uptake Study

Triple negative breast cancer cell line MDA-MB-231 known to overexpress EGFR was used to study NE uptake. Briefly, cells were grown on a Chambered Nunc Borosilicate #1 coverglass in presence of complete media. After 24 hours, the media was dispensed, cells washed with PBS, and incubated with fresh media containing 1 uM of either GE11-NP or D4-NP for 3 hours. The cells observed under confocal microscope.

Results

Example 2: Engineering of Thermostable Exoshells (tES)

Figure 2A:
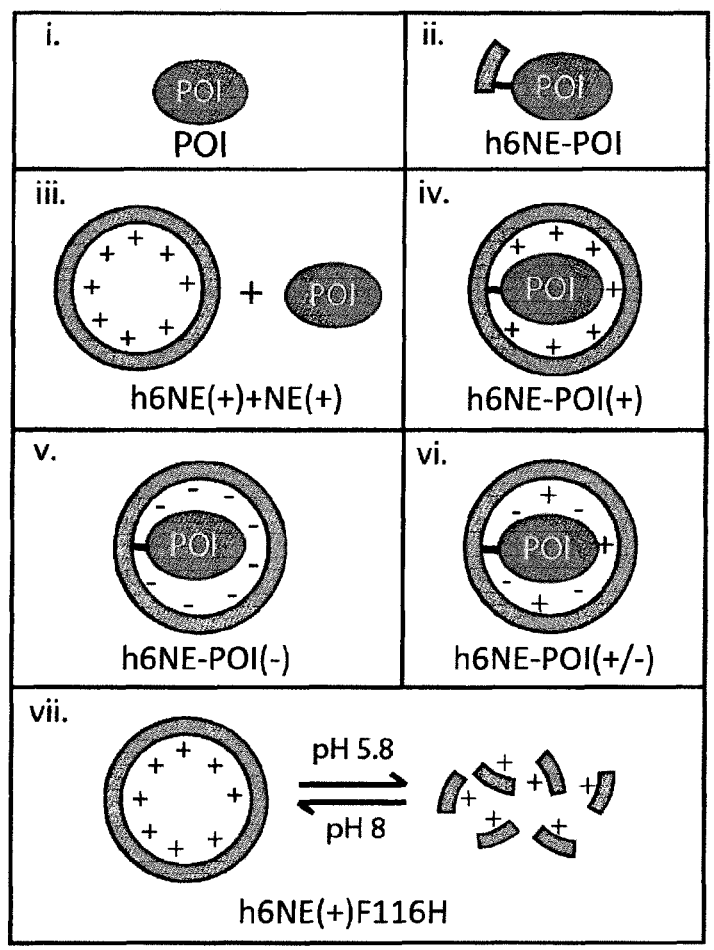
FIGS. 2A-2D show effect of NE shells on the soluble expression of POI.
Figure 2B:
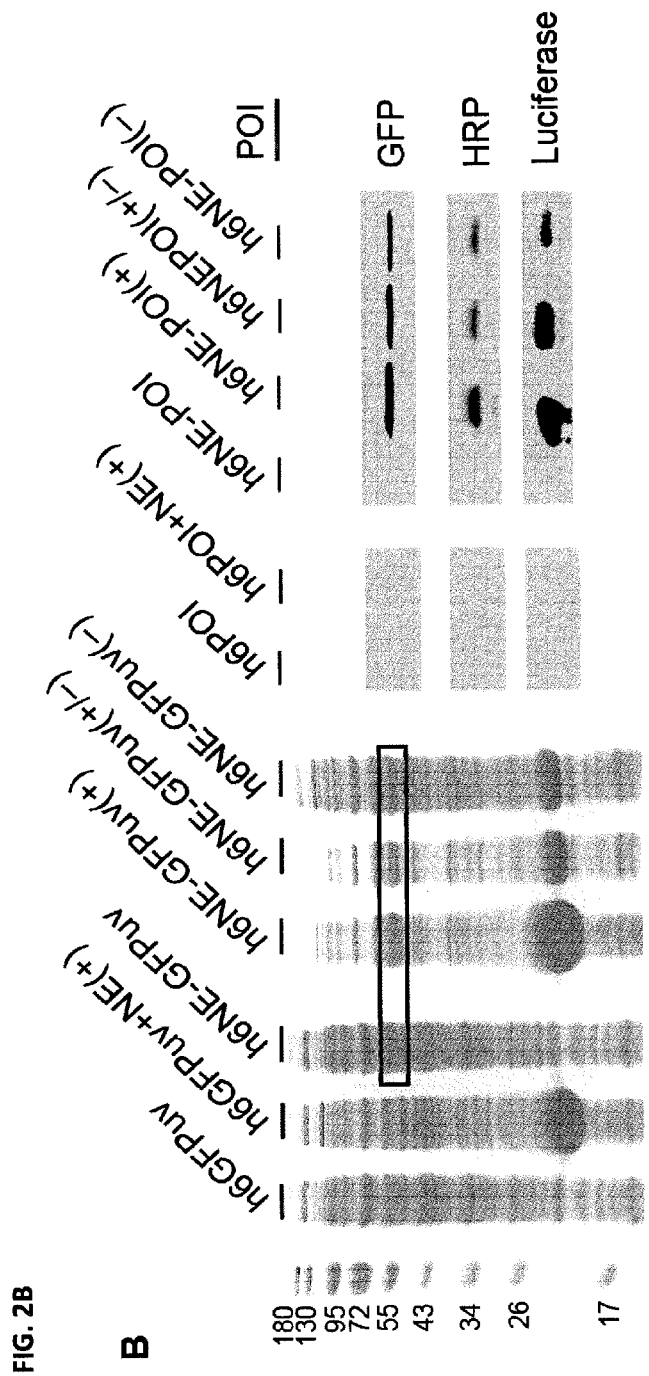
Figure 2D:
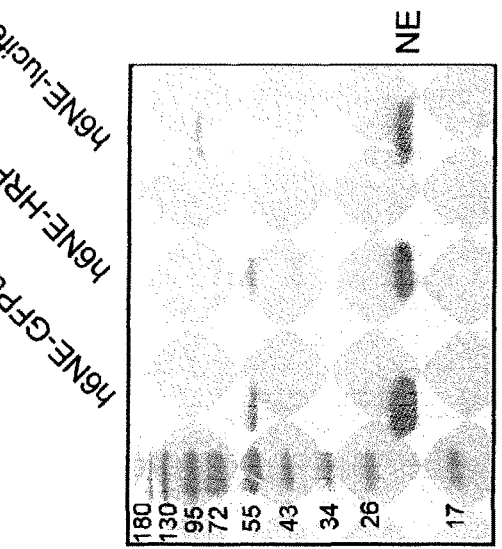
Figure 2C:
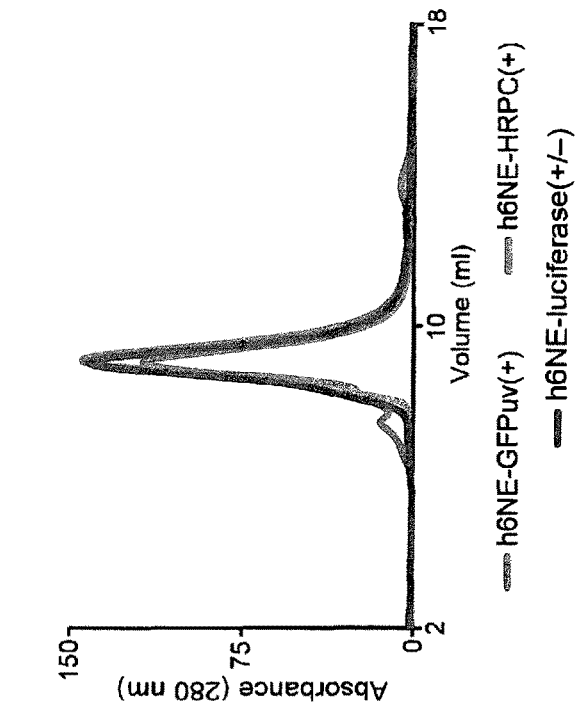

The interior of AfFtn assembly was engineered to maximize the cage volume and accommodate the folding requirements of the internalized proteins. Examination of the primary sequence and crystal structure of wild-type (WT) AfFtn revealed that the subunit interface residues are predominantly hydrophobic and the residues in the interior are negatively charged (Johnson, E. et al., *Structure.* 13, 637-648 (2005)). In total, ~25 kDa and 72 negative charges contribute to the interior volume of AfFtn assembly from the unstructured C-termini of WT subunits. The engineered NEs described herein are C-terminus truncation mutants at residue 164 (FIGS. 7A-7F). Comparison between size-exclusion profiles of truncated and WT AfFtn demonstrated that the C-terminus truncation did not affect the nanocage assembly. Surprisingly, analytical light scattering studies revealed that removal of the C-terminus stabilized the assembly even at low salt concentration (FIG. 1B).

The assembly was further engineered to examine the effect of charge in the nanoenvironment on protein expression and folding. Hydrophilicity matching has been proposed as a mechanism by which proteins define exterior versus interior charged residues (Seebeck, F. P. et al., K. J. *J. Am. Chem. Soc.* 128, 4516-4517 (2006)). To test a charge complementarity approach to macroglobular folding, interior facing residues were mutated to provide net positive, negative, and neutral charge on the internal cavity (FIGS. 7A-7F and FIGS. 8A-8C). Positive shells showed a higher expression than neutral and negative shells, with an estimated yield of 412, 402, and 237 mg/L (approximately 36%, 35.23%, and 20.76%, respectively, of total bacterial protein estimated by densitometry using ImageJ software) for tES (+), tES(+/−), and tES(−), respectively However, all NEs exhibited similar hydrodynamic diameters (FIGS. 9A-9F).

Example 3: Iron Uptake Qualities of tES

The native AfFtn shell is a physiologic iron-storage protein; we thus investigated whether tES variants also retain iron, either in our purified preparation or when exposed to an in vitro iron loading protocol (Macara I G, et al., *The Biochemical journal* 126, 151-162 (1972)). Equimolar amounts (1 μM) of tES(+), tES(−), tES(+/−), and commercially available horse spleen ferritin were compared and we observed no detectable iron core in purified tES variants (FIG. 10A) (Johnson, E. et al., *Structure.* 13, 637-648 (2005)). Iron uptake was then tested using equimolar amounts (1 μM) of wild-type AfFtn, tES(+), tES(−), tES(+/−), tES(+)F116H, tES(+)F116H/tES-GFPuv, tES(+)F116H/tES-HRPC, and tES(+)F116H/tES-rLuc. Wild-type AfFtn showed the highest in vitro iron uptake, while empty tES shells had appreciable but lower iron accumulation, likely due to amino acid substitutions near the ferroxidase center (E128 and E131) (Klenk H P, et al. *Nature* 390, 364-370 (1997)). Comparison of tES(+) and tES(+)F116H iron uptake was qualitatively similar, indicating that the F116H mutation had little effect on iron uptake. All three tES(+)F116H/tES-POI had greatly reduced (~1-2%) iron uptake when compared with wild-type AfFtn and empty tES variants (FIG. 10B).

Example 4: Effect of F116H Mutation on Shell Assembly

Given the high stability of the NE shell assembly (FIGS. 11A-11C), a responsive shell that could encapsulate and release the internalized cargo through mild pH titration was created. NEs are stable under mildly acidic condition (5-6) (FIGS. 12A-12I). Phenylalanine at the $116^{th}$ position (of SEQ ID NO: 1) was identified as a key inter-subunit contact and substituted with histidine (FIG. 12A). Owing to its position within the three-fold symmetry axis, an F116H mutation was predicted to create a mutually repulsive interaction at the interface when subjected to pH 5.8. The resulting shells, tES(+)F116H, tES(−)F116H, and tES(+/−) F116H, showed near complete disassembly at pH 5.8, with stable and reversible assembly at pH 8 (FIG. 10 and FIGS. 12A-12I). Using these six variants, it was determined whether surrounding a recombinant protein with a nanoscale thermostable shell could result in improved solubilization, functional folding, and controlled release of an internalized, functional protein.

Example 5: Encapsulation of Proteins Using Plasmid Expression System

As a proof of concept, four fusion proteins were created using multiple protein substrates (FIG. 2A). The stoichiometry of the encapsulated fusion protein to shell components is expected to be 1:23. Thus, a two-plasmid system was employed to achieve a finely titratable expression of the fusion protein, in addition to a gross overexpression of the surrounding shell components. For encapsulation, the following polypeptides were selected: (1) GFPuv (28 kDa)—a green fluorescent protein variant optimized for excitation by ultraviolet light—as it shows highly variable native expression in *E. coli*, is easily assayed in whole lysate, and does not require extrinsic factors to create a fluorophore (Penna, T. C. V. et al., *African J. Biotechnol.* 3, 105-111 (2004)); (2) firefly luciferase (61 kDa)—a light-emitting, adenylate-forming enzyme—to examine a relatively large enzyme that requires interdomain allosteric interactions for its activity (Branchini, B. R. et al., J. Am. Chem. Soc. 133, 11088-11091 (2011); (3) horseradish peroxidase isozyme C (HRPC, 36 kDa)—a widely used industrial enzyme—as a more challenging POI, as it has no reported soluble expression in *E. coli*, contains four disulfide bonds (correct pairing of which is essential for its activity), and requires heme as a prosthetic group (Krainer, F. W. and Glieder, A. *Appl. Microbiol. Biotechnol.* 99, 1611-1625 (2015); Ren, G. and Bardwell, J. C. *Antioxid. Redox. Signal.* 14, 2399-2412 (2011)); and (4) *Renilla* luciferase (rLuc, 36 kDa) due to an absence of previous reports of successful in vitro refolding, its relatively high thermolability, and ease of functional assay as a bioluminescent reporter enzyme. The calculated internal volume of an NE (8 $nm^3$) corresponds to an upper limit of ~120 kDa for encapsulation, assuming a spherical macroglobule (Erickson, H. *Biol Proced Online.* 15, 32-51 (2009)).

In *E. coli*, GFPuv exhibits easily detectable expression when induced in the early exponential growth phase (O.D.₆₀₀=0.4), but very low expression when induced in the late exponential phase (O.D.₆₀₀=0.8). When induced in late exponential phase, His-tagged (h6GFPuv), as well as GFPuv fused to a single NE subunit (h6NE-GFPuv), produced no detectable soluble protein as probed by Western blotting. However, when the fusion protein was co-expressed with NE (ferritin subunits) of positive, neutral, or negative interior charge, the soluble expression was significantly increased, evident as a distinct band on Western and Coomassie-stained SDS gels (FIG. 2B, right and left panels, respectively)). h6NE-GFPuv(+) showed the highest soluble expression. Similar results were seen with HRPC and luciferase (with the exception of rLuc, which is previously reported to result in soluble expression in $E.\ coli$), with no detectable soluble expression for tagged or fusion forms and clear bands seen in the presence of NE co-expression. To test specifically the importance of fusion protein encapsulation, the NE was co-expressed with a non-fused POI [h6P01+NE (+)], which also showed negligible expression (FIG. 2B; right panel, second lane). Assembly of the NE subunits with the fusion NE-POI is further supported by $Ni^{2+}$-affinity chromatography, wherein an N-terminal His-tag on the fusion subunit pulls down the non-His-tagged shell subunits such that the assembly co-elutes on size exclusion chromatography at a predicted molecular mass of 480 kDa and demonstrates purified bands on an SDS gel consistent with NE and NE-POI subunits (FIGS. 2C and 2D).

Example 6: POIs are Functionally Expressed

Figure 3B:
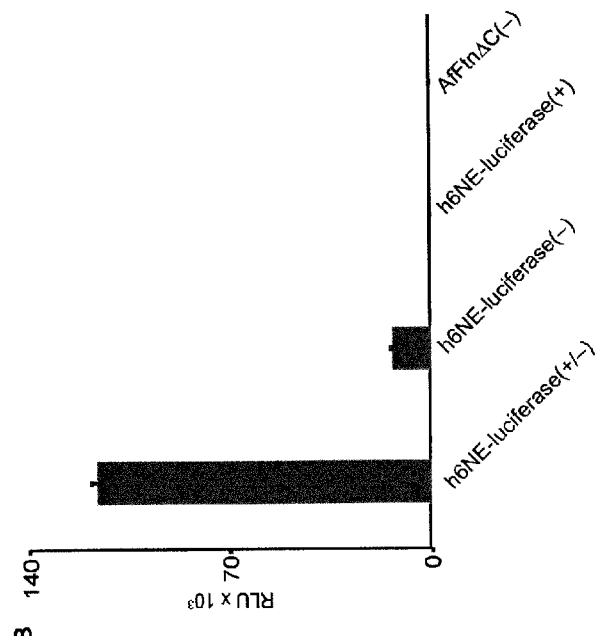
FIGS. 3A-3F show effect of NE shells on the functional expression of POI.
Figure 3A:
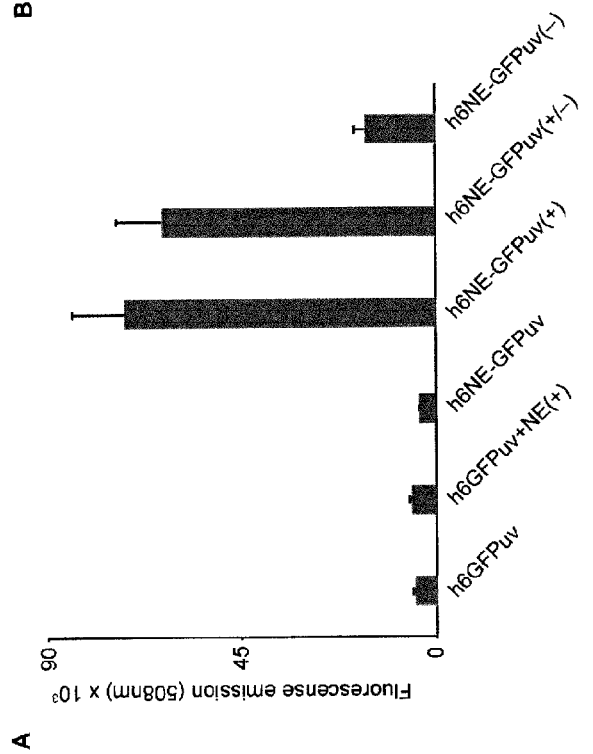

The effect of NEs on the functional expression of the POIs was assessed. GFPuv fluorescence was consistent with the observed expression levels, with no significant fluorescence in the lysate for h6GFPuv, h6NE-GFPuv, and h6GFPuv+NE(+). Using the titratable L-arabinose promoter system, and with GFPuv as an example, the effect of L-arabinose on the functional expression of POI was evaluated (FIGS. 13A-13D). Using 0.01% L-arabinose maximum fluorescence was observed for encapsulated GFPuv, with NE(+) showing maximum activity (FIG. 3A). Equimolar concentrations of purified luciferase in positive, neutral, and negative NEs were evaluated for luciferase activity using D-luciferin as substrate. h6NE-luciferase(+/−) exhibited higher activity than negative and positive cages (>10-fold and 100-fold, respectively) (FIG. 3B). The NE(+) shell resulted in the highest relative concentration of soluble product, with yields of 79.5, 74, and 57 mg/L of GFPuv, HRPC, and rLuc, respectively, as analyzed by densitometry using ImageJ software. We hypothesize that this may be due to charge complementation between the net negative surface charge of the POIs and the net positive charge of the NE(+) internal surface. Assembly of tES(+)/tES-POI was confirmed by pull down of shell components by the histidine-tagged fusion subunit, followed by size-exclusion chromatography (SEC) to confirm tES/tES-POI assembly. The ratios of tES-GFP, tES-HRP and tES-rLuc to encapsulating tES subunits were in approximate agreement with the expected value of 1:23 (1:32, 1:19, and 1:20, respectively) as estimated by gel densitometry of purified protein fractions.

Figure 3C:
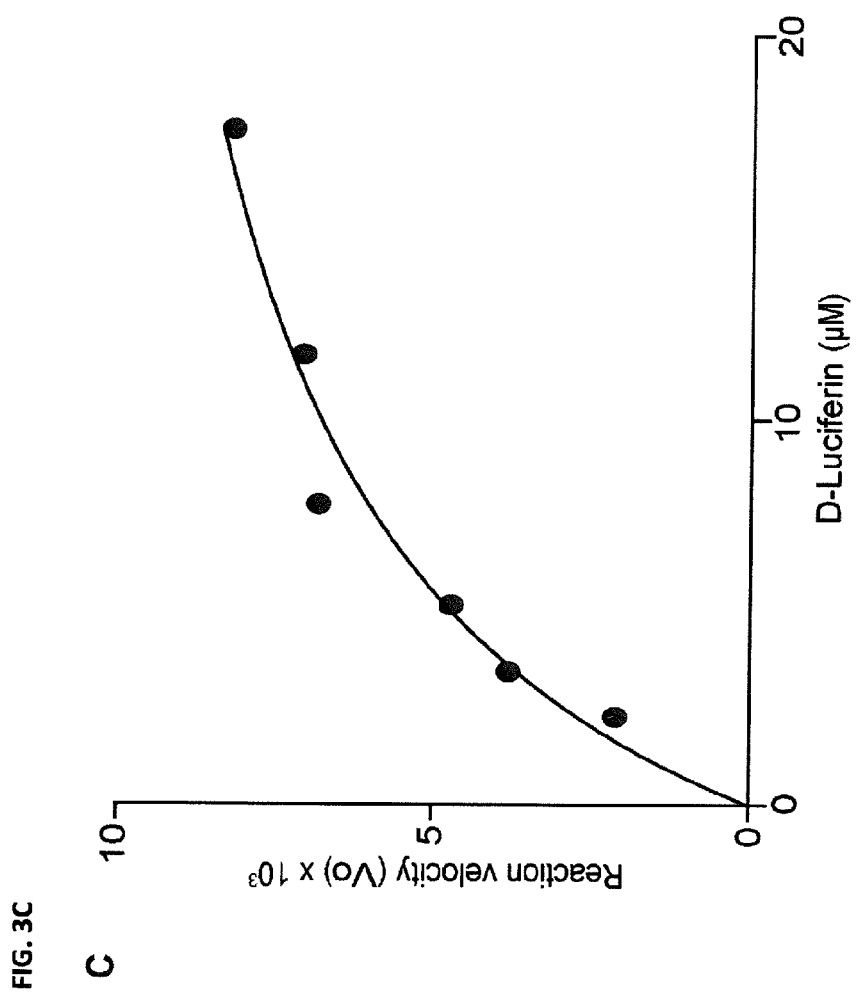
Figure 3E:
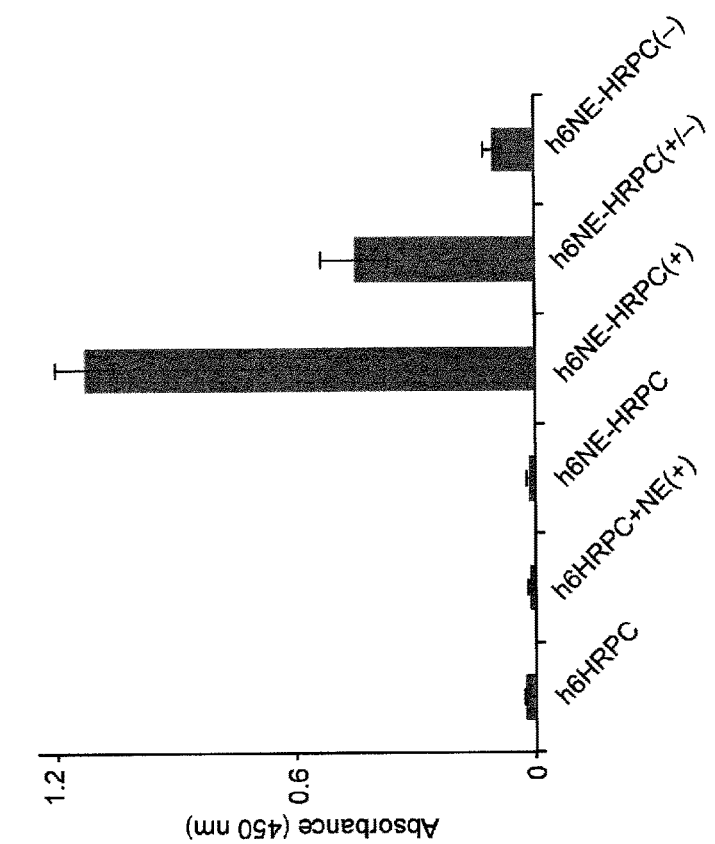
Figure 3D:
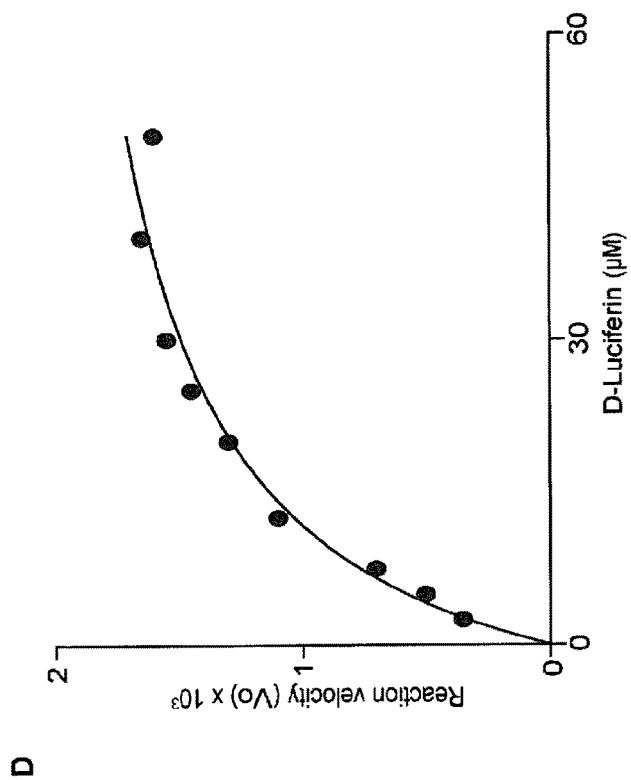

Thus, the kinetics of h6NE-luciferase(+/−) catalyzed light-emission reaction was studied and compared it to that of recombinant luciferase (FIGS. 3C and 3D). The kinetic parameters Km and Vmax were 8.1±0.15 μM and 14943±3889 μM/s, respectively, for free luciferase, and 16.21±0.819 μM and 2412±295 μM/s, respectively, for h6NE-luciferase(+/−). The decrease in Vmax (six-fold) and increase in Km (two-fold) is potentially related to the diffusional limitations of the product and substrate imposed by the surrounding cage. Also, the constraint in the structural flexibility of the enzyme within the limited space of the NE may have contributed to these changes (Sundlov, J. A. et al., $Biochemistry$ 51, 6493-6495 (2012)).

Figure 3F:
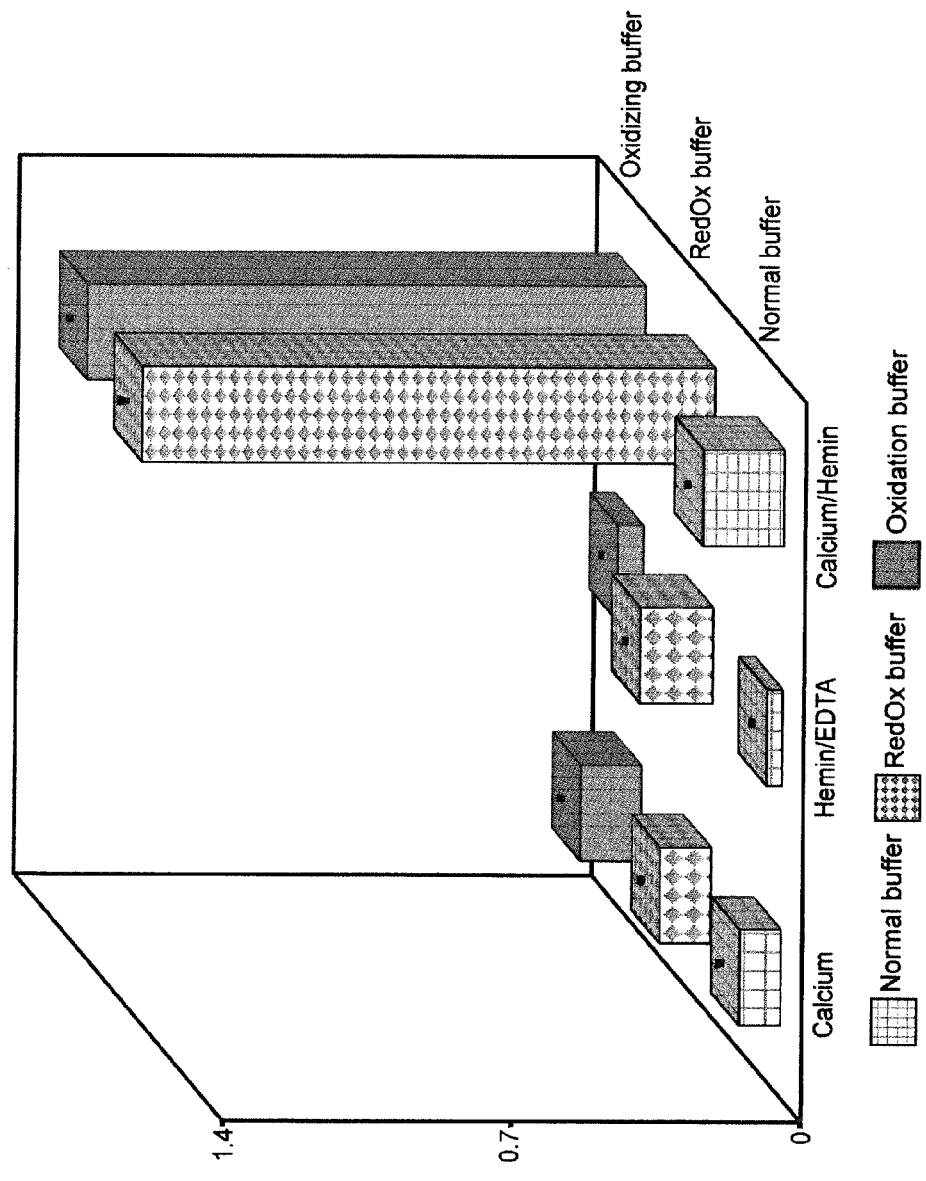
Figure 5B:
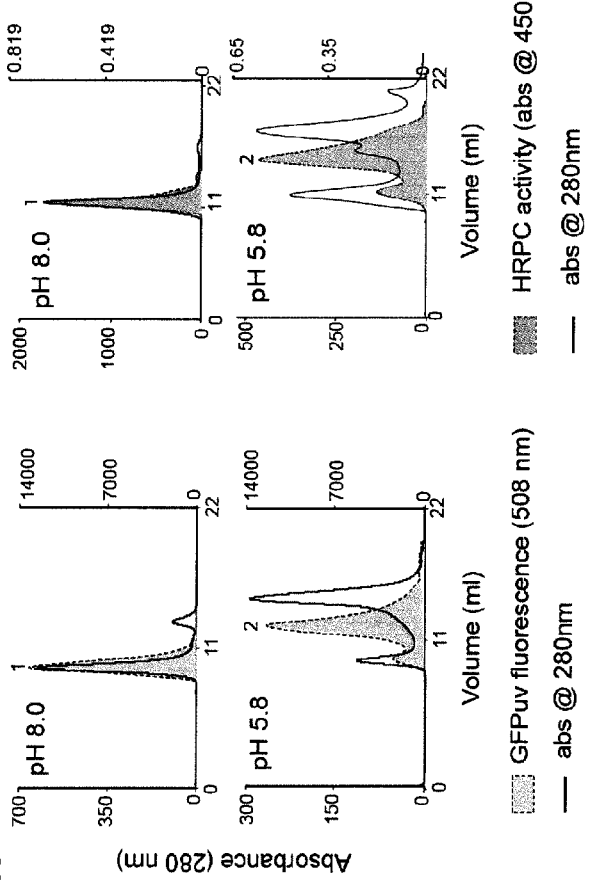
FIGS. 5A-5E show internalization and recovery of active proteins from the NE shell.
Figure 5A:
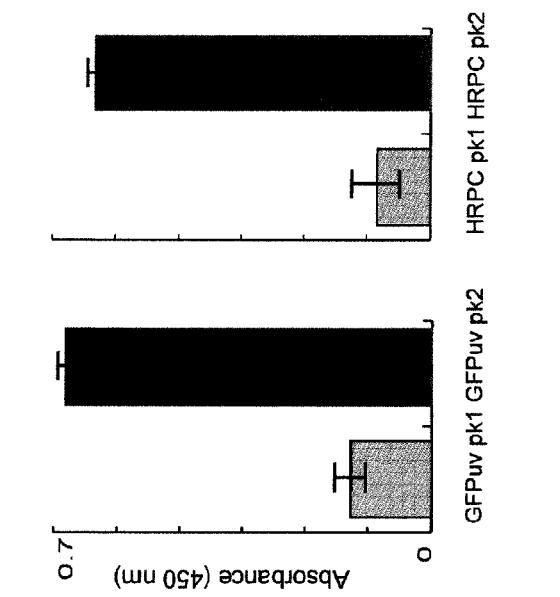
Figure 5D:
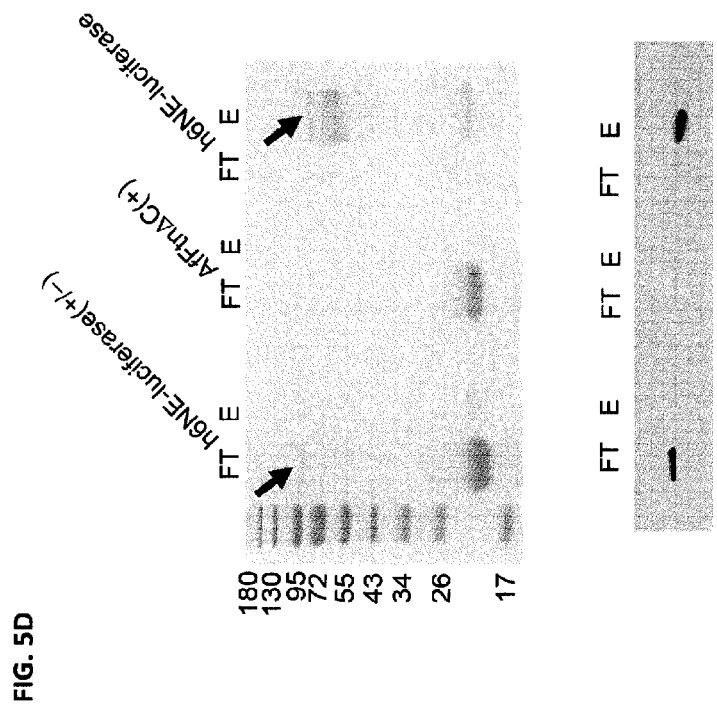
Figure 5C:
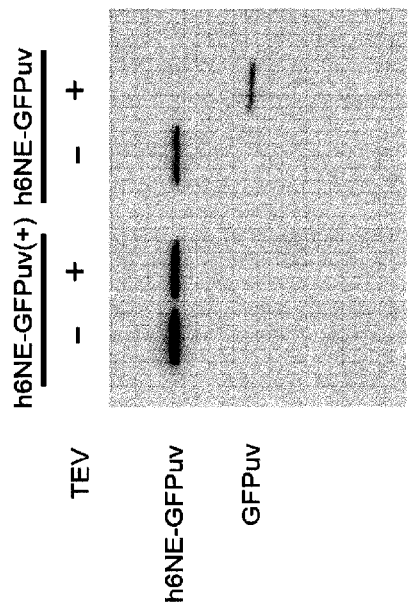
Figure 5E:
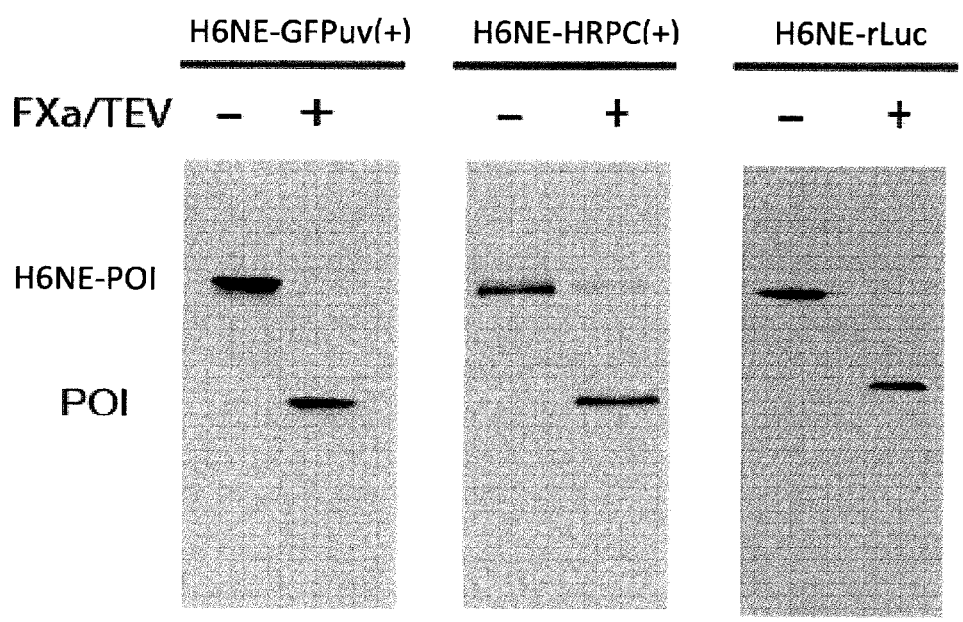
Figure 6:
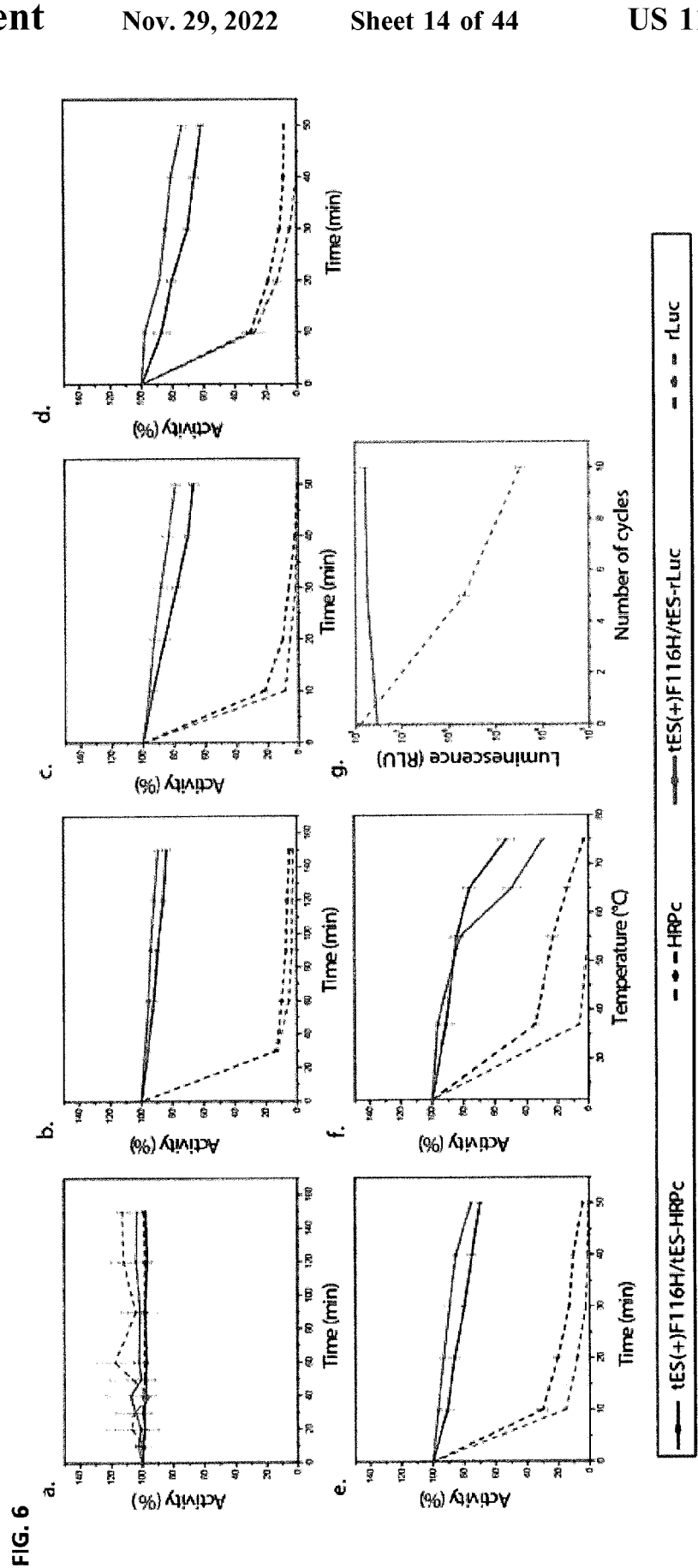
FIG. 6 shows effect of tES on the stability of the encapsulated POI (HRPC or rLuc). (a) POI is stable in the dialysis buffer with and without encapsulation. Presence of tES enhanced the stability of tES-POI in (b) 0.4% trypsin, (c) 20% methanol, (d) 8 M urea, and (e) 30% acetonitrile. (f) tES(+)F116H/tES-POI is resistant to 15 min of thermal denaturation. (g) tES(+)F116H/tES-rLuc is highly resistant to repeated thermocycling (80° C.×5 min×10 cycles) showing a three order-of-magnitude higher activity compared with rLuc.
Figure 7E:
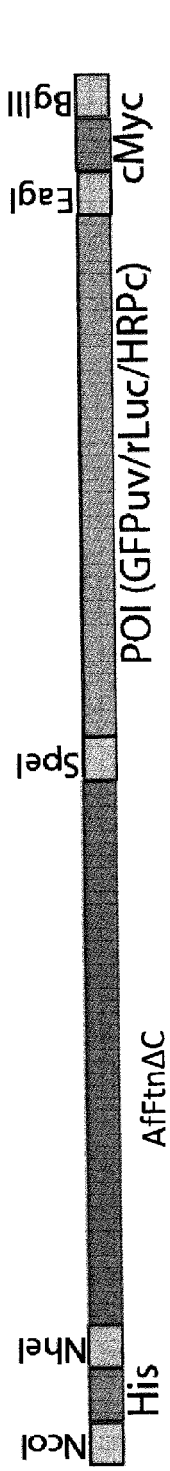
Figure 7F:
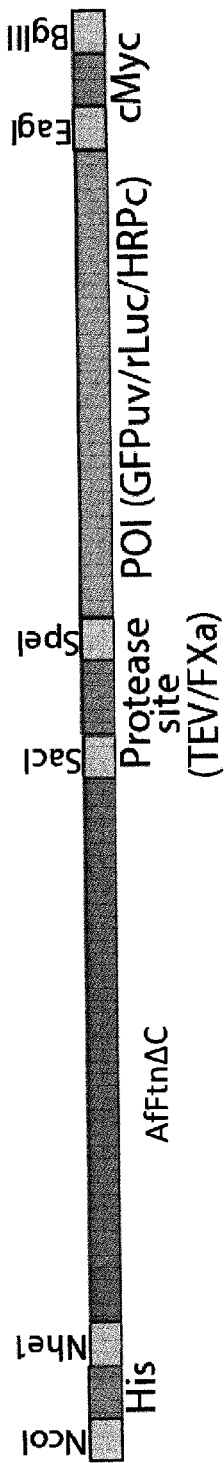
Figure 8A:
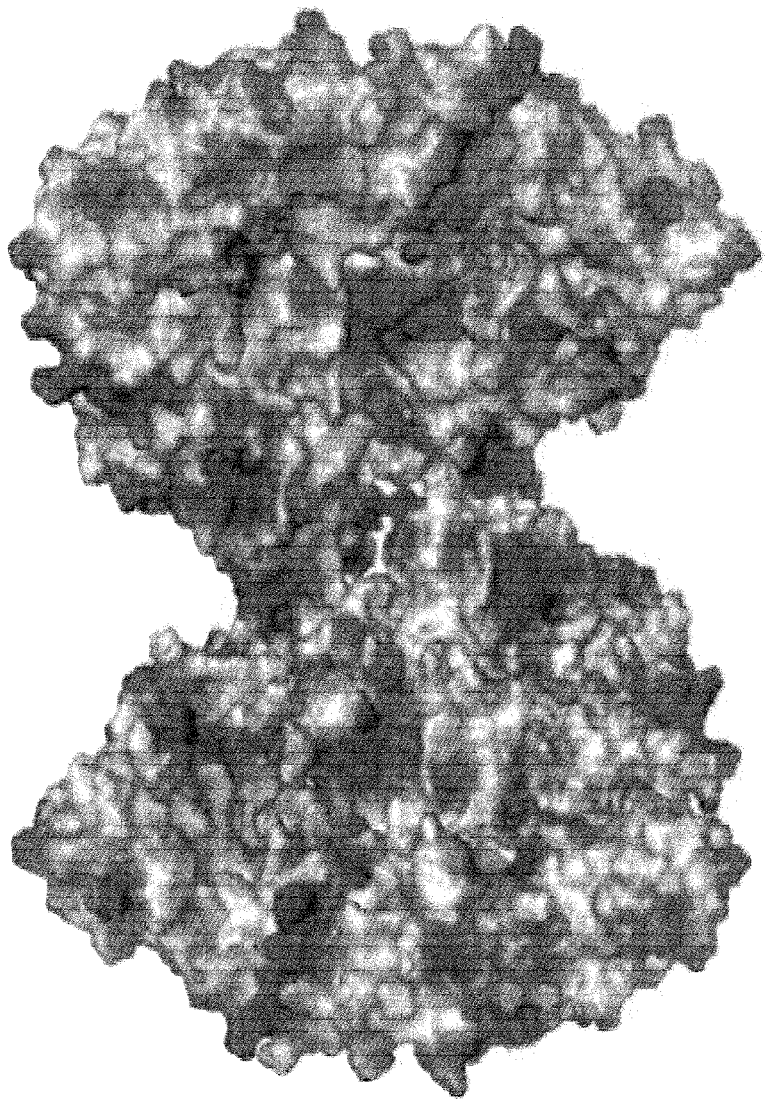
FIGS. 8A-8C show molecular surface rendering of 12 subunits of AfFtn with truncated C-terminus [AfFtnΔC] (PDB accession code 1SQ3).
Figure 8B:
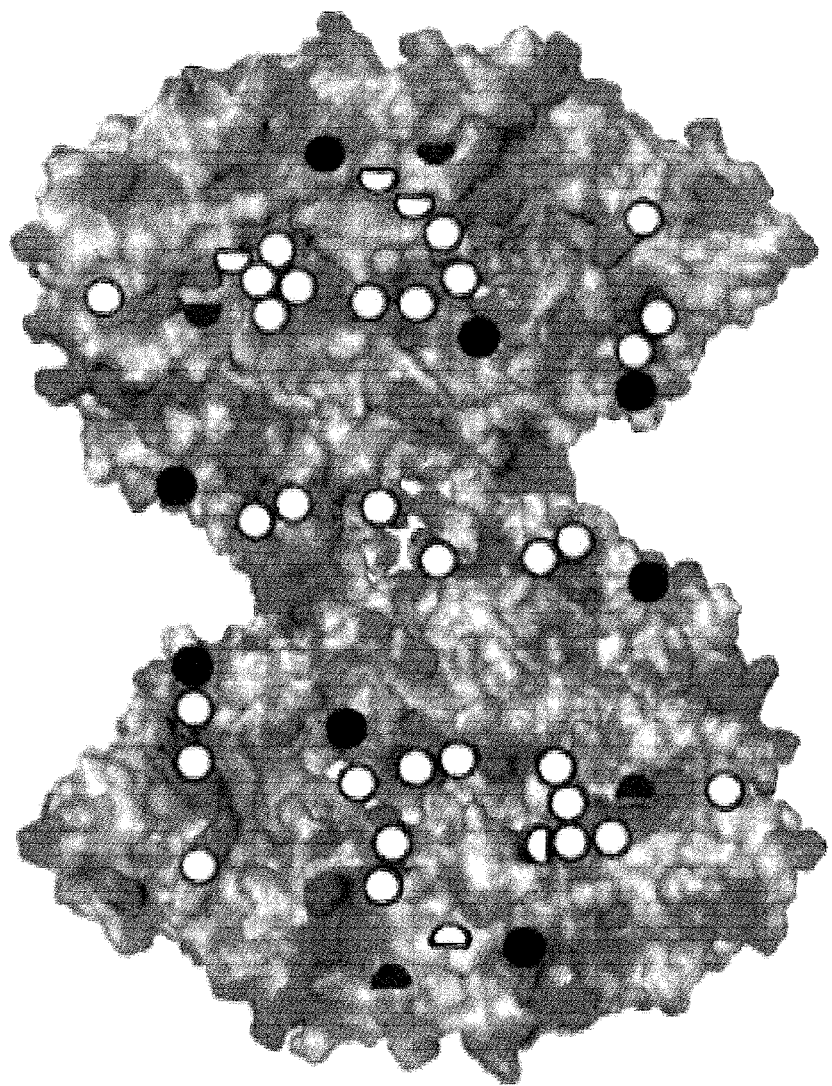
Figure 8C:
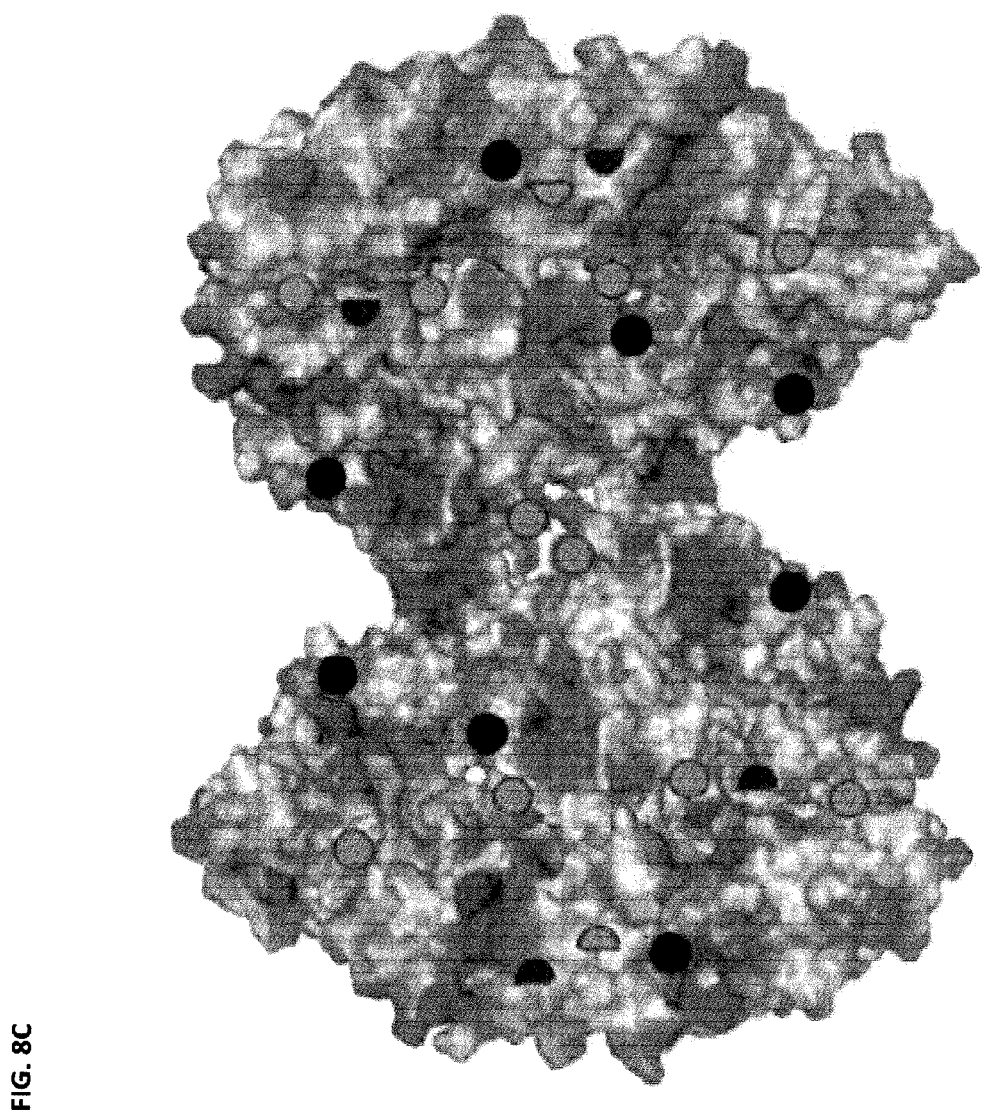
Figure 9A:
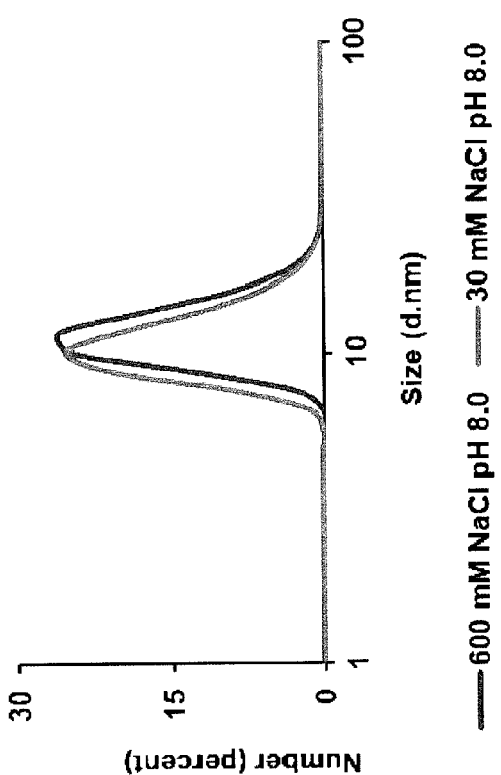
Figure 9B:
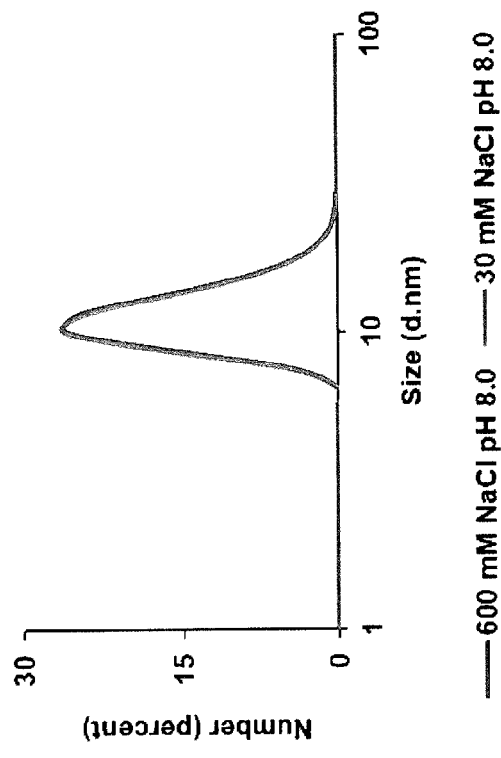

HRPC represents a complex challenge, in that the reducing environment of $E.\ coli$ would typically not allow formation of disulfide bonds, while the native heme expression in $E.\ coli$ may not be sufficient to supply an overexpressed protein. Functional expression of HRPC in $E.\ coli$ has not been previously reported. Using NEs, functional expression of HRPC in $E.\ coli$ was achieved with the addition of supplemental oxidation and known cofactors, calcium and heme (FIG. 3E). Notably, all post-expression HRPC additions were performed in aqueous buffer, in contrast with previously described inclusion body refolding protocols using 8M urea. The effect of cofactors/additives on HRPC activity was also evaluated in NE shells. HRPC activity was assessed from cell lysates processed under identical conditions in presence of cofactors calcium and hemin and additives (oxidizing and reducing agents). The activity was minimal under reducing conditions and maximal when either oxidized glutathione or a 1:1 mixture of oxidized and reduced glutathione was added. Likewise, maximal activity could only be obtained in the presence of both cofactors (FIG. 3F).

Example 7: Effect of Different tES:tES-GFPuv Ratios on In Vitro Folding

The ability of tES to aid in vitro folding of proteins was tested. The tES(+)F116H assembly is highly stable at pH 8.0, as evidenced by similar elution profiles on SEC after treatment with 8 M urea or 6 M guanidinium hydrochloride (GuHCl), compared with PBS controls. Likewise, tES(+)F116H can reversibly associate and dissociate with pH titration with no observable precipitates. We then hypothesized tES could functionally encapsulate substrate proteins under conditions that would denature the POI. tES fusion proteins express as inclusion bodies in the absence of co-expressed tES. Thus, using tES(+)F116H, we tested ratios of tES to tES-POI, using a pH shift from 5.8 to 8.0 to induce assembly of the shell. The addition of tES(+)F116H to tES-GFPuv resulted in a ~100-fold increase in functional yield, which was maximum at a 90:1 ratio of tES(+)F116H subunits to tES-GFPuv (FIG. 4A). We found that heating the inclusion body suspension to 60° C. in the presence of 6 M GuHCl and 10 μM β-mercaptoethanol was critical for maximum final yield.

Example 8: Requirement for tES for Functional In Vitro Protein Folding

Figure 20:
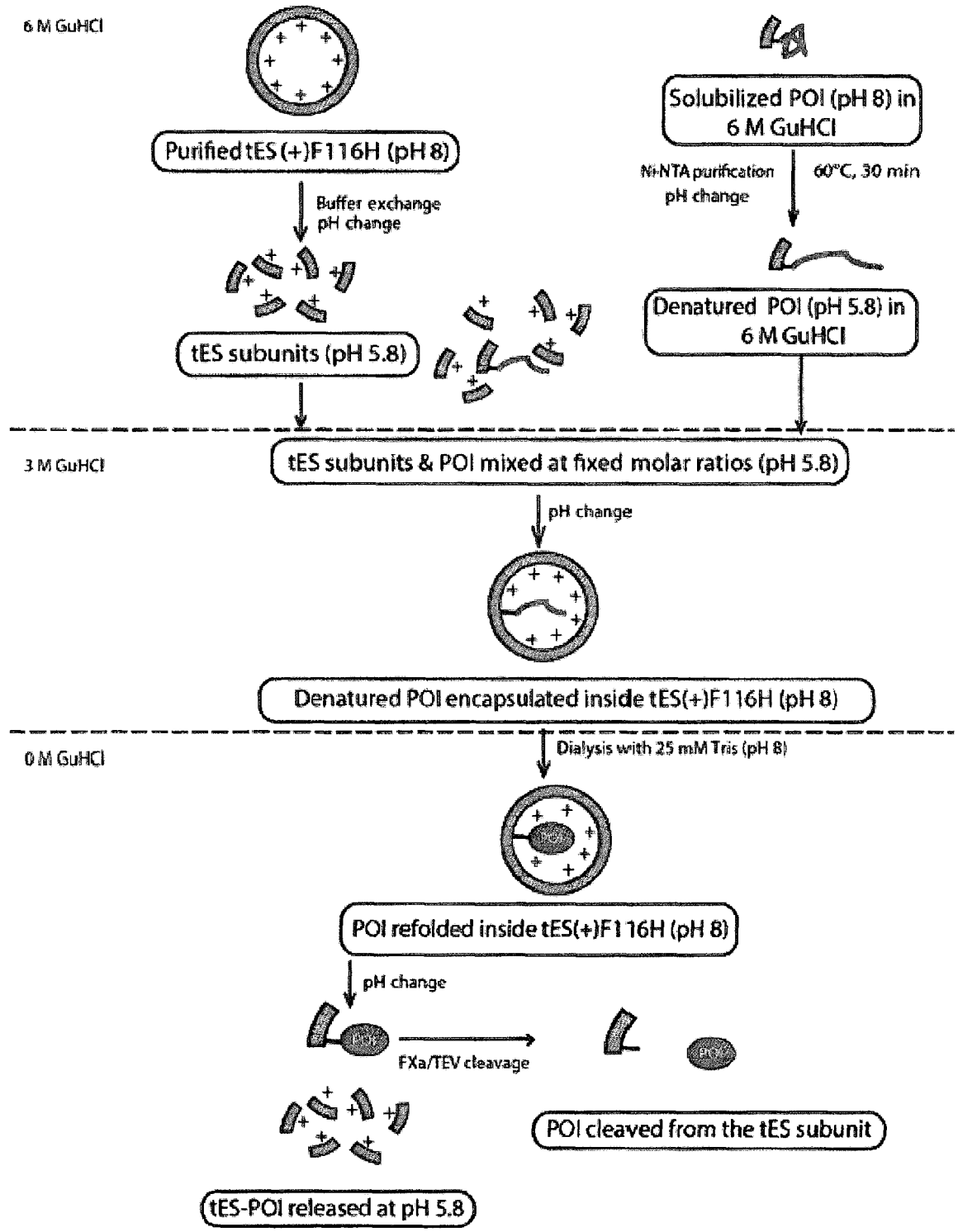
FIG. 20 shows a protocol for in vitro folding of proteins of interest (P01). The tES-POI was solubilized in 6 M GuHCl and heated at 60° C. to ensure its complete denaturation. Following denaturation, tES-POI mixed with tES subunits at fixed molar ratio at pH 5.8. The pH was gradually changed to 8 to ensure encapsulation of the denatured protein inside tES(+)F116H. The POI was subjected to dialysis using 25 mM Tris buffer, pH 8, for its folding inside tES(+)F116H.
Figure 21A:
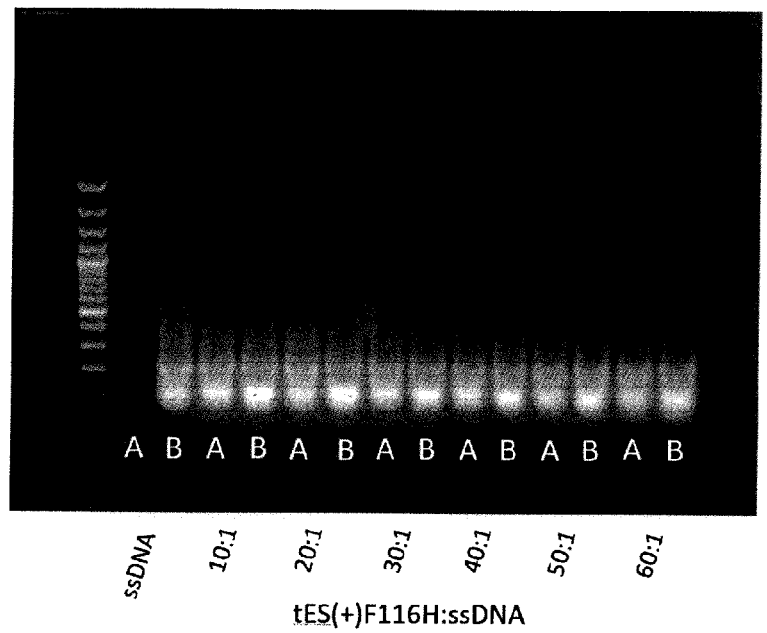
FIGS. 21A-21B show effect of different molar ratios of tES(+)F116H subunits on naked ssDNA encapsulation in vitro.
Figure 21B:
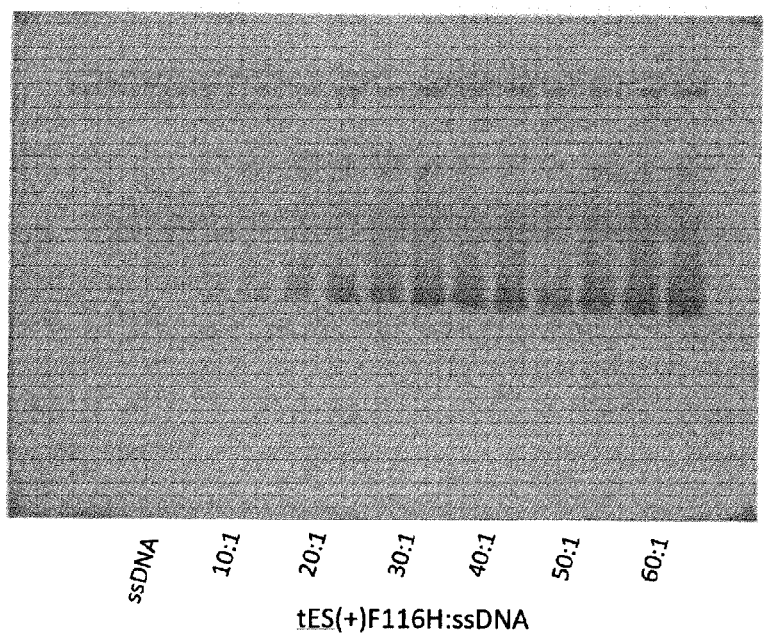
Figure 22A:
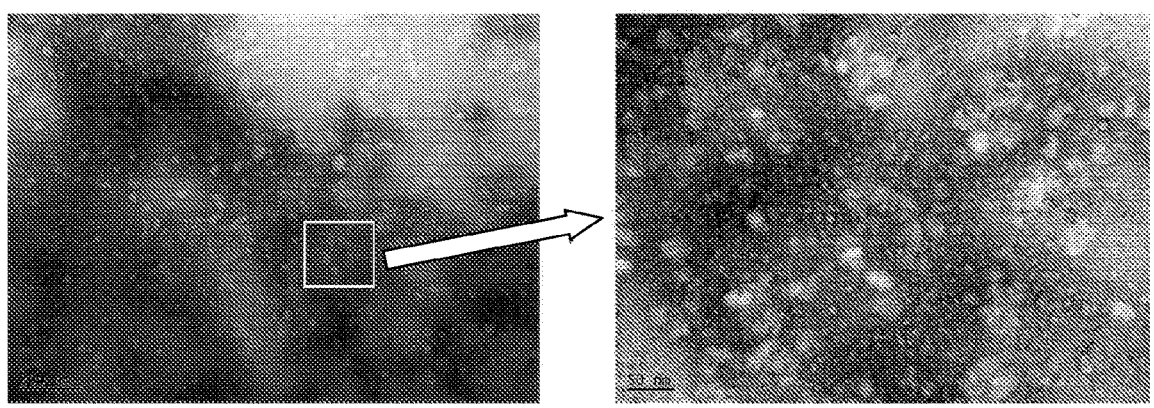
FIGS. 22A-22B are transmission electron micrographs of tES(+)F116H with and without plasmid addition.
Figure 22B:
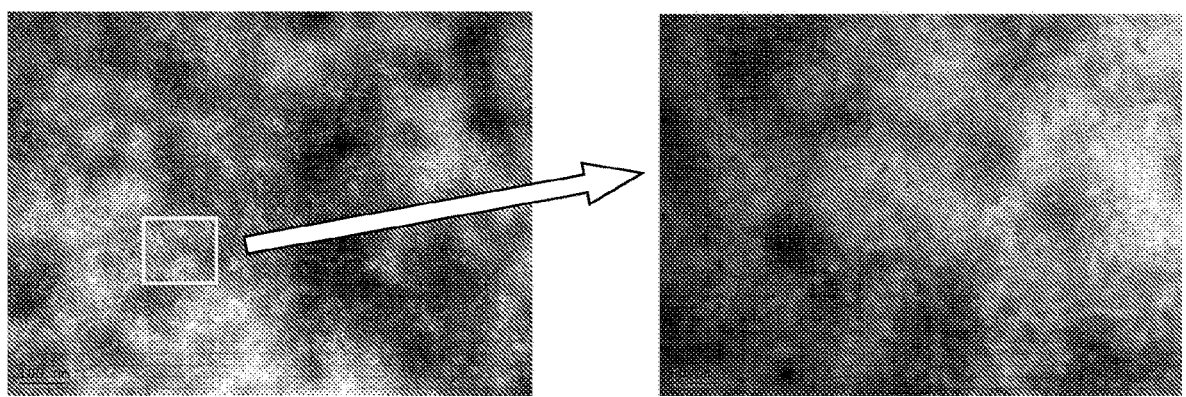

Based on pH titration results (FIG. 4A), we developed a standard protocol with a 60:1 ratio of tES(+)F116H:tES-POI, starting with all components in 6 M GuHCl at pH 5.8. Protein-specific, post-translationally required agents were added and the solution then dialyzed against GuHCl-free buffer at pH 8.0 (FIG. 20). Using this protocol, we demonstrate a near absolute requirement for tES for functional in vitro folding of tES-GFPuv, tES-rLuc, and tES-HRPC. Under the same protocol, very little or no functional yield of GFPuv, HRPC, or rLuc, was observed in the absence of tES (FIG. 4B). A similar pattern of protein activity was seen in $E.\ coli$ lysates with the exception of rLuc, which is known to express as a soluble protein in $E.\ coli$ (FIG. 4C)(Lorenz W W, et al., *Proceedings of the National Academy of Sciences of the United States of America* 88, 4438-4442 (1991)).

Example 9: Internalization of the POI

Using pH-titratable NE shells, internalization of the POI was demonstrated by showing the ability of NEs to hide epitopes of the internalized POI and protect it from proteolysis. The POI is fused to the cavity-facing C-terminus of the E helix, presumably forcing the fusion to reside within the interior. All tested assemblies had the same diffusional diameter (~12 nm) (FIGS. 9A-9E), and at pH 8.0, all assemblies eluted as a peak with an expected hydrodynamic diameter same as that of the POI-encapsulated NE (FIGS. 9A-9E). Both GFPuv and HRPC activities could be observed at this peak. At pH 5.8, protein activity shifted to a peak distinct from that for the assembly and with a predicted molecular mass of fusion protein (FIG. 5A). To test the internalization of the POI, an epitope protection assay was developed using antibodies specific to the POI. With pH-titratable NE, a significantly greater signal was seen after cage disassembly versus the same sample applied in the assembled form (FIG. 5B). An additional assay of GFPuv demonstrated protease protection with encapsulation but not as an isolated fusion protein (FIG. 5C). A pull-down assay was used to study luciferase encapsulation, showing specific pull-down of h6NE-luciferase (absent from the flow through and present in the elute), whereas h6NE-luciferase (+/−) was protected from the pull-down and clearly visible in the flow through (FIG. 5D). The ability to separate the POI from the fusion to produce an independently-folded and solubilized protein was also tested. Western blot analysis demonstrated successful proteolytic separation of POIs (GFPuv and HRPC) to produce bands consistent with the native POI (FIG. 5E).

Example 10: Cell Targeting of Engineered Ferritin Assembly

FIG. 15 illustrates efficient cell targeting and uptake of the engineered ferritin assembly (the nanoshell) by MDA-MB-231 cancer cell line. In this study, a polypeptide was not encapsulated into the nanoshell. Vesicular and cytoplasmic localization of the internalized particles is seen.

Example 11: Stabilization of POI Using tES (HRPC or rLuc)

The inventors tested the ability of tES to impart thermostable qualities to internalized proteins. GFPuv is highly stable in its native form. We therefore tested rLuc and HRPC versus un-encapsulated controls to determine the stabilizing effect of tES encapsulation. For both rLuc and HRPC, tES was protective from 0.4% trypsin, 30% acetonitrile, 20% methanol, 8 M urea, 6 M GuHCl, and thermal denaturation (FIG. 6*a*-*g*).

Example 12: Cell-Free Encapsulation of Un-Fused POI in tESF116H Shells

We tested the possibility of encapsulation and folding of native HRPC (34 kDa) in tES(+)F116H by using the in-vitro folding protocol, wherein the NE subunits were mixed with denatured HRPC in fixed molar ratios—60:1, 60:3, 60:5, 60:8, 60:10, 60:12 and 60:15. It was observed that with increasing HRPC concentration, more HRPC was encapsulated and folded inside tES(+)F116H as seen from activity and thermal shift data (FIGS. 16A-17A and 17C). However, after 60:10 ratio, the amount of HRPC encapsulated within tES(+)F116H remained constant. This is possibly since at this concentration, all NE are filled with HRPC and no empty NE subunits are left to encapsulate the protein. It was observed that HRPC did not encapsulate successfully in tES(−)F116H even when higher molar ratios of 60:8 and 60:10 were used as seen from activity and thermal shift data (FIGS. 17B, 17D). This might be due to the fact that HRPC has a net negative charge and hence tES(−)F116H is unable to encapsulate it due to charge similarity. A similar observation was obtained for encapsulation of GFPuv (27 kDa) (FIGS. 18A-18D) and rLuc (FIG. 19).

Example 13: Cell-Free Encapsulation of Un-Fused Nucleic Acid in tESF116H Shells

We tested the possibility of encapsulation of ssDNA (98 bases) in tES(+)F116H by using the in-vitro encapsulation protocol, wherein the tES(+)F116H subunits were mixed with ssDNA in fixed molar ratios—10:1, 20:1, 30:1, 40:1, 50:1, and 60:1. It was observed that all ratios of subunits to DNA encapsulated the nucleic acid and protected it from DNAse degradation, as seen in lanes marked 'A' (FIG. 21A). We also tested possibility of ferritin attachment to plasmid through charge complimentary effect. pRSF plasmid (4113 base pairs) was used for the particular experiment. tES(+)F116H subunits were mixed with plasmid in fixed ratio of 1000:1. It was observed that tES(+)F116H aggregated in circular pattern when mixed with plasmid (FIG. 22B). However, no circular patterns were observed for the same concentration tES(+)F116H nanocages with no plasmid addition (FIG. 22A). This strongly suggests attachment of tES(+)F116H around the pRSF plasmid caused by charge complimentary effect.

Summary

The pathway from nascent polypeptide to functional protein structure is determined by a balance of factors, some working in favor of, and many against, the successful folding of the end product. Natural chaperones prevent the aggregation of unfolded or partially-folded intermediates, undergo specific interactions that bias folding along productive energetic pathways, and exert kinetic effects that accommodate folding processes of widely varying time scales. In the setting of recombinant expression, the intrinsic chaperone level in an *E. coli* cell may be overwhelmed by the bulk of nascent, unfolded recombinant protein. In support of this hypothesis, the overexpression of native chaperones such as Hsp70 and GroEL/GroES complex has aided recombinant protein expression (Saibil H. Chaperone machines for protein folding, unfolding and disaggregation. *Nature reviews Molecular cell biology* 14, 630-642 (2013)). Chaperone overexpression has also shown limits in its application, as the co expression of DnaJ, DnaK, and GrpE with HRP inhibited the growth of host cells (Kondo A, et al., *Journal of bioscience and bioengineering* 90, 600-606 (2000)), and DnaK-assisted expression of GFP resulted in reduced yield and lower conformational quality of the target protein (Martinez-Alonso M, Vera A, Villaverde A. *FEMS microbiology letters* 273, 187-195 (2007); Garcia-Fruitos E, et al., *Journal of molecular biology* 374, 195-205 (2007)).

Studies using the P22 VLP bacteriophage have shown sequestration of recombinant protein within the interior surface. However, the requirement of ~450 coat proteins, additional scaffold proteins, and the harsh conditions required to disassociate the capsid have limited P22 use in recombinant expression (Marta Comellas-Aragonès H E, et al., *Nature Nanotechnology* 2, 635-639 (2007)).

By using 23 copies of a single thermostable subunit to form a protective shell around internalized proteins, we report that tES can improve expression, in vitro folding, and product stabilization. tES(+)F116H can release encapsulated protein with mild pH titration (pH 5.8-6.0) and the soluble protein fusions can be selectively proteolyzed to create monomeric protein products.

We have also shown that, whilst a fusion/linker between a protein and tES subunit is required for cellular production and encapsulation, a protein of interest can be encapsulated in a tES in a cell-free environment by using tESF116H subunits at a suitable subunit: protein ratio and assembly at pH 8. Without wanting to be bound by theory, it appears that the internal charge of the tES is very important when a linker is not used, whereby the charge within the capsule needs to be opposite or neutral relative to that of the POI.

A caveat of this study is that we used protein function as a surrogate for folding. Thus, to understand the precise effects of nanoenvironmental engineering on the folding of protein substrates, further studies such as differential scanning calorimetry, deuterium exchange, and cryo-electron microscopy may be needed. Because each POI substrate is physically isolated from other unfolded proteins via the tES, we hypothesize that folding studies can be performed at higher concentration without aggregation.

Although ~80% of translated proteins in the eukaryotic genome are 80 kDa or smaller, the uses of tES may be broadened by variants with larger internal volumes. This will be particularly important for POIs that require multimerization for optimum activity. The ability to stabilize thermolabile substrates within tES may be helpful for a variety of applications in bionanotechnology and synthetic biology, including the production of difficult-to-fold proteins, using the shell as a mediator of cellular enzyme uptake, and exploiting the stabilized qualities of tES substrates in industrial settings.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

REFERENCES

Any listing or discussion of an apparently prior-published document in this specification should not necessarily be taken as an acknowledgement that such document is part of the state of the art or is common general knowledge.

Branchini, B. R. et al., Bioluminescence is produced from a trapped firefly luciferase conformation predicted by the domain alternation mechanism. *J. Am. Chem. Soc.* 133, 11088-11091 (2011).

Comellas-Aragones, M. et al., A virus-based single-enzyme nanoreactor. *Nat Nanotechnol.* 2, 635-639 (2007).

Daggett, V. and A. Fersht, A. The present view of the mechanism of protein folding. *Nat. Rev. Mol. Cell. Biol.* 4, 497-502 (2003).

Erickson, H. Size and shape of protein molecules at the nanometer level determined by sedimentation, gel filtration, and electron microscopy. *Biol Proced Online.* 15, 32-51 (2009).

Garcia-Fruitos E, et al., Divergent genetic control of protein solubility and conformational quality in *Escherichia coli*. *Journal of molecular biology* 374, 195-205 (2007).

Hartl, F. U. and Hayer-Hartl, M., *Nat. Struct. Mol. Biol.* 16, 574-581 (2009).

Hartl, F. U. et al., Converging concepts of protein folding in vitro and in vivo. *Nature.* 475, 324-332 (2011).

Johnson, E, et al., Crystal structures of a tetrahedral open pore ferritin from the hyperthermophilic archaeon *Archaeoglobus fulgidus*. *Structure.* 13, 637-648 (2005).

Kim, Y. E. et al., Molecular chaperone functions in protein folding and proteostasis. *Annu. Rev. Biochem.* 82, 323-355 (2013).

Klenk H P, et al. The complete genome sequence of the hyperthermophilic, sulphate-reducing archaeon *Archaeoglobus fulgidus*. *Nature* 390, 364-370 (1997).

Kondo A, et al. Improvement of productivity of active horseradish peroxidase in *Escherichia coli* by coexpression of Dsb proteins. *Journal of bioscience and bioengineering* 90, 600-606 (2000).

Konho, et al., A novel hybrid peptide targeting EGFR-expressing cancers. *Eur J Cancer.* 47:773-783 (2011).

Krainer, F. W. and Glieder, A. An updated view on horseradish peroxidases: recombinant production and biotechnological applications. *Appl. Microbiol. Biotechnol.* 99, 1611-1625 (2015).

Liu, X, et al., Opening protein pores with chaotropes enhances Fe reduction and chelation of Fe from the ferritin biomineral. *Proc. Natl. Acad. Sci. U.S.A* 100, 3653-3658 (2003).

Lorenz W W, et al., Isolation and expression of a cDNA encoding *Renilla reniformis* luciferase. *Proceedings of the National Academy of Sciences of the United States of America* 88, 4438-4442 (1991).

Macara I G, Hoy T G, Harrison P M. The formation of ferritin from apoferritin. Kinetics and mechanism of iron uptake. *The Biochemical journal* 126, 151-162 (1972).

Marta Comellas-Aragones H E, et al., A virus-based single-enzyme nanoreactor. *Nature Nanotechnology* 2, 635-639 (2007).

Martinez-Alonso M, et al., Role of the chaperone DnaK in protein solubility and conformational quality in inclusion body-forming *Escherichia coli* cells. *FEMS microbiology letters* 273, 187-195 (2007).

Patterson, D. P. et al., Rescuing recombinant proteins by sequestration into the P22 VLP. *Chem. Commun.* (Camb). 49, 10412-10414 (2013).

Penna TCV, Ishii, M., de Souza, L. C. & Cholewa, O. Expression of green fluorescent protein (GFPuv) in *Escherichia coli* DH5-a, under different growth conditions. *African J. Biotechnol.* 3, 105-111 (2004).

Ren, G. and Bardwell, J. C. Engineered pathways for correct disulfide bond oxidation. *Antioxid. Redox. Signal.* 14, 2399-2412 (2011).

Saibil H. Chaperone machines for protein folding, unfolding and disaggregation. *Nature reviews Molecular cell biology* 14, 630-642 (2013).

Sana, B, et al., The role of nonconserved residues of *Archaeoglobus fulgidus* ferritin on its unique structure and biophysical properties. *J. Biol. Chem.* 288, 32663-32672 (2013).

Seebeck, F. P, et al., A simple tagging system for protein encapsulation. *J. Am. Chem. Soc.* 128, 4516-4517 (2006).

Sundlov, J. A. et al., Crystal structure of firefly luciferase in a second catalytic conformation supports a domain alternation mechanism. *Biochemistry* 51, 6493-6495 (2012).

Zarschler, et al., Diagnostic nanoparticle targeting of the EGF-receptor in complex biological conditions using single-domain antibodies. *Nanoscale* 6:6046-6056 (2014).

What is claimed is:

1. An engineered thermostable ferritin assembly comprising a modified ferritin subunit derived from a wildtype *Archaeoglobus fulgidus* ferritin assembly subunit, wherein the modified ferritin subunit comprises the amino acid sequence set forth in SEQ ID NO: 1, except that the modified ferritin subunit lacks residues 165-173 of SEQ ID NO: 1 and comprises zero or more amino acid substitutions at one or more positions selected from the group consisting of E65, F116, E128, E131 and D138 of SEQ ID NO: 1, and wherein the engineered thermostable ferritin assembly comprises pores communicating the interior with the exterior of the assembly, exhibits enhanced thermostability relative to said wildtype ferritin assembly and is stable at lower salt concentrations than said wildtype ferritin assembly.

2. The engineered ferritin assembly of claim 1, wherein the assembly possesses a net positive interior charge, or a net neutral interior charge.

3. The engineered ferritin assembly of claim 2, wherein the modified ferritin subunit comprises an amino acid substitution at any one or more positions selected from E65, E128, E131, and D138.

4. The engineered ferritin assembly of claim 1, wherein the modified ferritin subunit comprises:
   (a) a substitution at position F116 of SEQ ID NO: 1 which renders the engineered assembly capable of assembly and/or disassembly dependent on pH; and/or
   (b) an amino acid sequence selected from the group consisting of SEQ ID NO: 2, SEQ ID NO: 3, SEQ ID NO: 4, SEQ ID NO: 5, and SEQ ID NO: 8.

5. The engineered ferritin assembly of claim 1, wherein a polypeptide, nucleic acid or small molecule is encapsulated within the ferritin assembly.

6. The engineered ferritin assembly of claim 1, wherein the modified ferritin subunit is fused to a polypeptide or nucleic acid and said polypeptide or nucleic acid is encapsulated within the ferritin assembly.

7. The engineered ferritin assembly of claim 6, wherein the polypeptide is fused to the modified ferritin subunit through a joining sequence.

8. The engineered ferritin assembly of claim 1, wherein the said stability in low salt concentrations is provided by chemical crosslinking of subunits.

9. An in vitro method of forming an engineered thermostable ferritin assembly comprising at least one modified ferritin subunit, the method comprising adjusting the pH from an acidic pH to basic pH of a sample comprising at least one modified ferritin subunit of claim 4.

10. The method of claim 9, further comprising a polypeptide or a nucleic acid in the sample whereby said polypeptide or nucleic acid is encapsulated by the engineered ferritin assembly at basic pH of the sample.

11. The method of claim 9, wherein the acidic pH in the sample is at least about 4.0 and/or the basic pH in the sample is about 8.0.

12. The method of claim 10, wherein the polypeptide or nucleic acid is fused to at least one modified ferritin subunit.

13. A method of encapsulating a polypeptide in an engineered thermostable ferritin assembly, comprising: 1) introducing into a cell a nucleic acid comprising: a) a first sequence that encodes a first modified ferritin subunit lacking an unstructured carboxy-terminal sequence that a wildtype ferritin subunit possesses; and b) a second sequence that encodes a second modified ferritin subunit lacking an unstructured carboxy-terminal sequence that a wildtype ferritin subunit possesses fused to a polypeptide; 2) expressing the first and second sequences; and 3) forming a ferritin assembly that encapsulates the polypeptide, wherein at least one of the first and the second modified ferritin subunit is as defined in claim 1.

14. The method of claim 13, wherein the first and second sequences are introduced into the cell on separate plasmids.

15. A method of delivering an engineered thermostable ferritin assembly into a cell, comprising contacting the cell with a ferritin assembly of claim 1.

16. The method of claim 15, wherein the ferritin assembly comprises a cell targeting moiety.

17. An isolated plasmid or vector nucleic acid comprising: a) a sequence that encodes a modified ferritin subunit ; and/or b) a sequence that encodes a modified ferritin subunit fused to a polypeptide, wherein the modified ferritin subunit is as defined in claim 1.

18. A composition or combination comprising at least one engineered thermostable ferritin assembly of claim 1 for use in the prophylaxis or treatment of disease in a subject.

19. The composition or combination of claim 18, wherein the at least one engineered thermostable ferritin assembly comprises:
i) an enzyme; and/or
ii) one or more additional therapeutic agents.

20. The composition or combination of claim 18, which is a vaccine.

21. A method of treatment or prophylaxis comprising administering to a subject in need of such treatment or prophylaxis an efficacious amount of a composition or combination of claim 18.

22. A kit, to encapsulate a polypeptide or nucleic acid within an engineered thermostable ferritin assembly, the kit comprising:
at least one modified ferritin subunit according to claim 1.

23. A kit, to encapsulate a polypeptide or nucleic acid within an engineered thermostable ferritin assembly, the kit comprising:
the plasmid or vector nucleic acid of claim 17.

24. The engineered ferritin assembly of claim 3, wherein the amino acid substitution comprises: i) substitutions E65K, E128K, E131K and D138A which cause the assembly to have a net positive interior charge; or ii) substitutions E65Q and D138A which cause the assembly to have a net neutral interior charge.

25. The engineered ferritin assembly of claim 4, wherein the substitution is F116H.

* * * * *

UNITED STATES PATENT AND TRADEMARK OFFICE
CERTIFICATE OF CORRECTION

PATENT NO. : 11,510,881 B2
APPLICATION NO. : 16/340089
DATED : November 29, 2022
INVENTOR(S) : Chester Lee Drum It is certified that error appears in the above-identified patent and that said Letters Patent is hereby corrected as shown below:

In the Specification

Column 6, Line 23, delete "(P01)." and insert -- (POI). --.

Column 14, Line 41, delete "(P01)" and insert -- (POI) --.

Column 14, Line 64, delete "(P01)" and insert -- (POI) --.

Column 16, Line 53-54, delete "therapies),In" and insert -- therapies). In --.

Column 18, Line 54, delete "mg/mi" and insert -- mg/ml --.

Column 19, Line 6, delete "mg/mi" and insert -- mg/ml --.

Column 19, Line 7, delete "mg/mi" and insert -- mg/ml --.

Column 20, Line 56, delete "$CaCl_2$)" and insert -- $CaCl_2$ --.

Column 23, Line 16, delete "P01" and insert -- POI --.

Column 23, Line 19, delete "P01" and insert -- POI --.

Column 23, Line 21, delete "P01" and insert -- POI --.

Column 23, Line 22, delete "P01" and insert -- POI --.

Column 23, Line 24, delete "P01" and insert -- POI --.

Figure 1C:
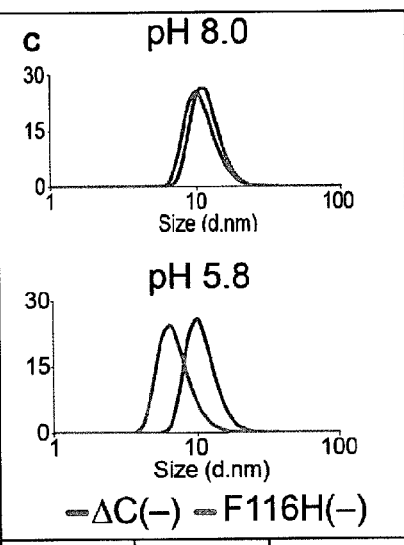
Figure 10A:
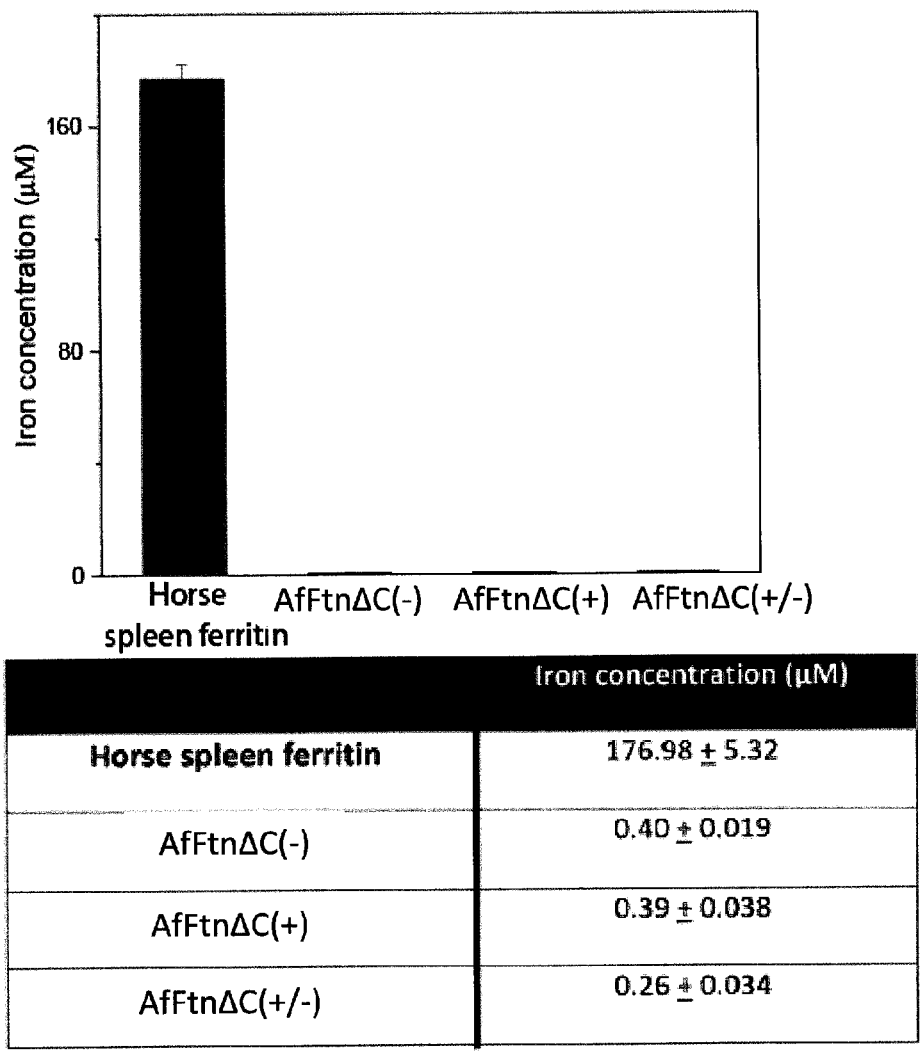
FIGS. 10A-10B show the results of an iron assay.
Figure 10B:
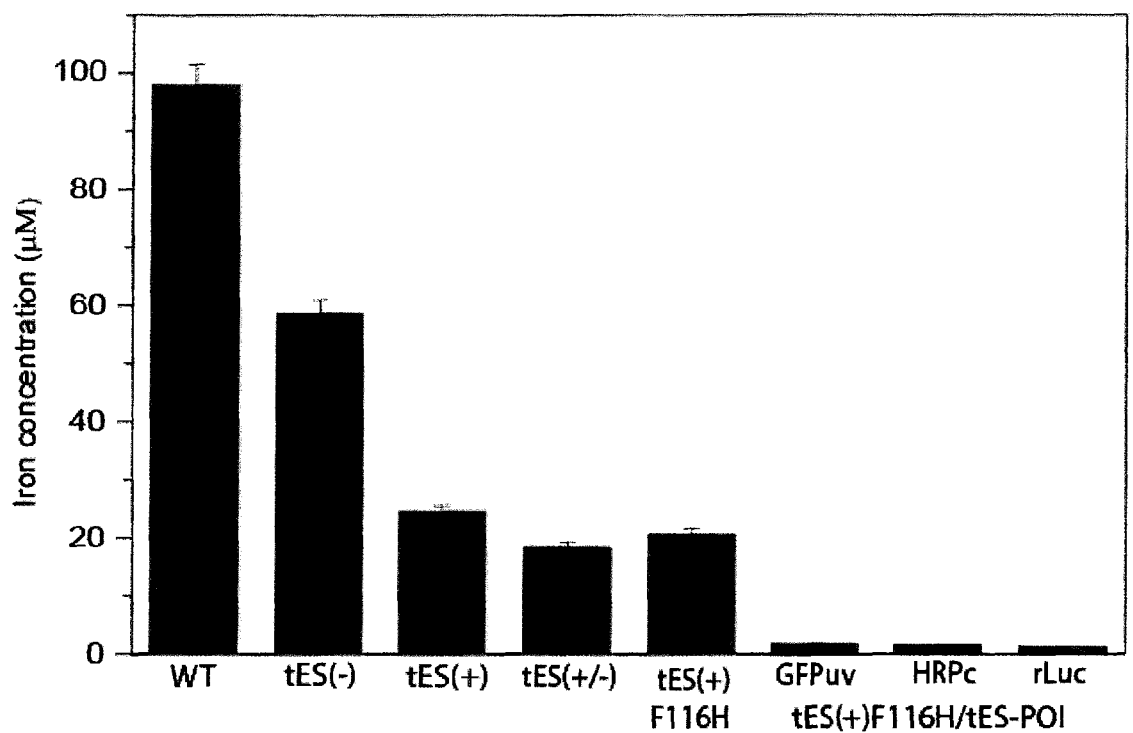
Figure 11B:
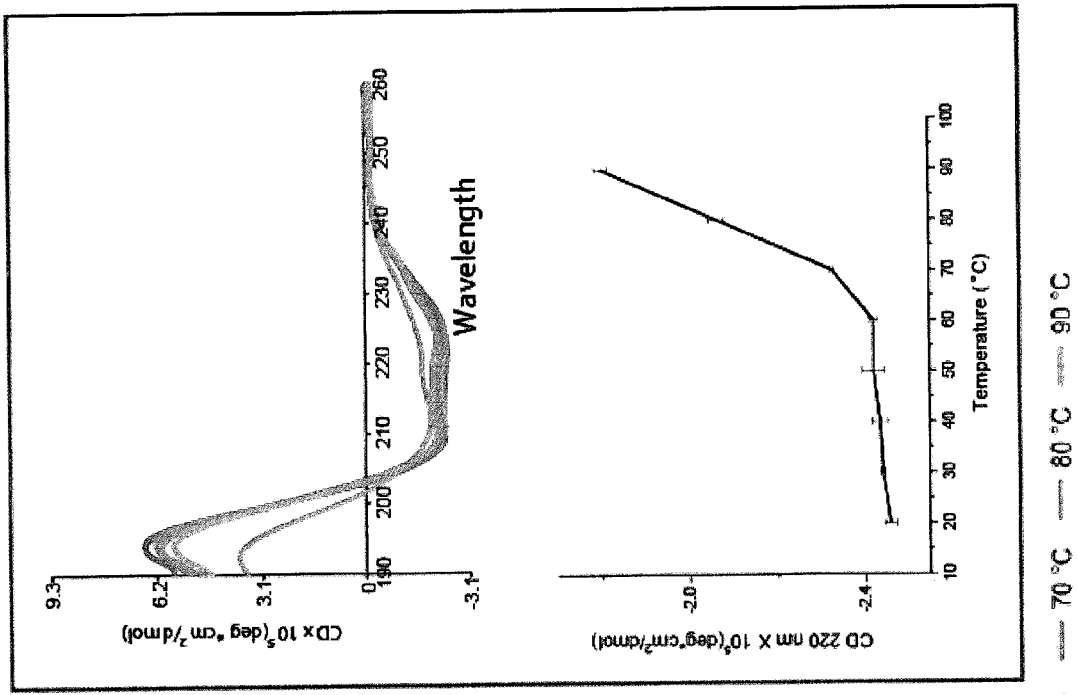
FIGS. 11A-11C show thermal unfolding studies with engineered AfFtn cages from 20° C. to 90° C. Far-UV CD spectrum of the cages (FIG. 11A AfFtnΔC(+)
Figure 11A:
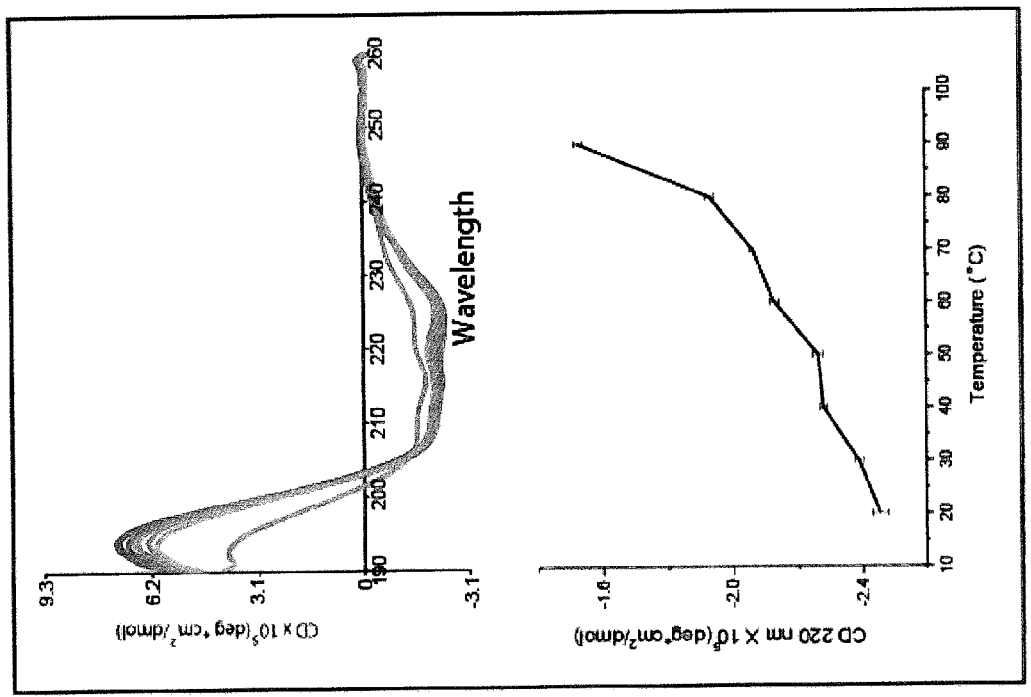
Figure 11C:
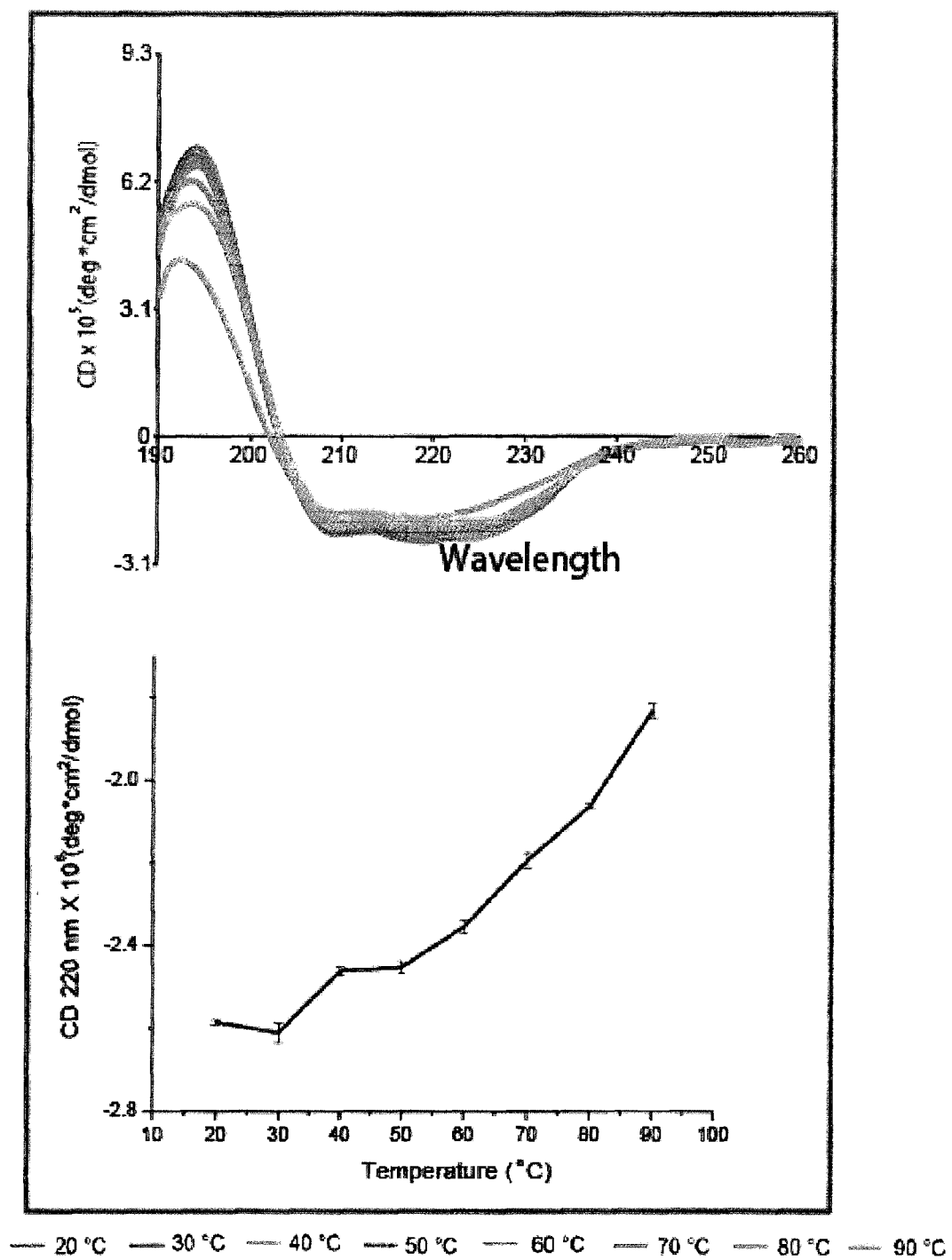
Figure 12A:
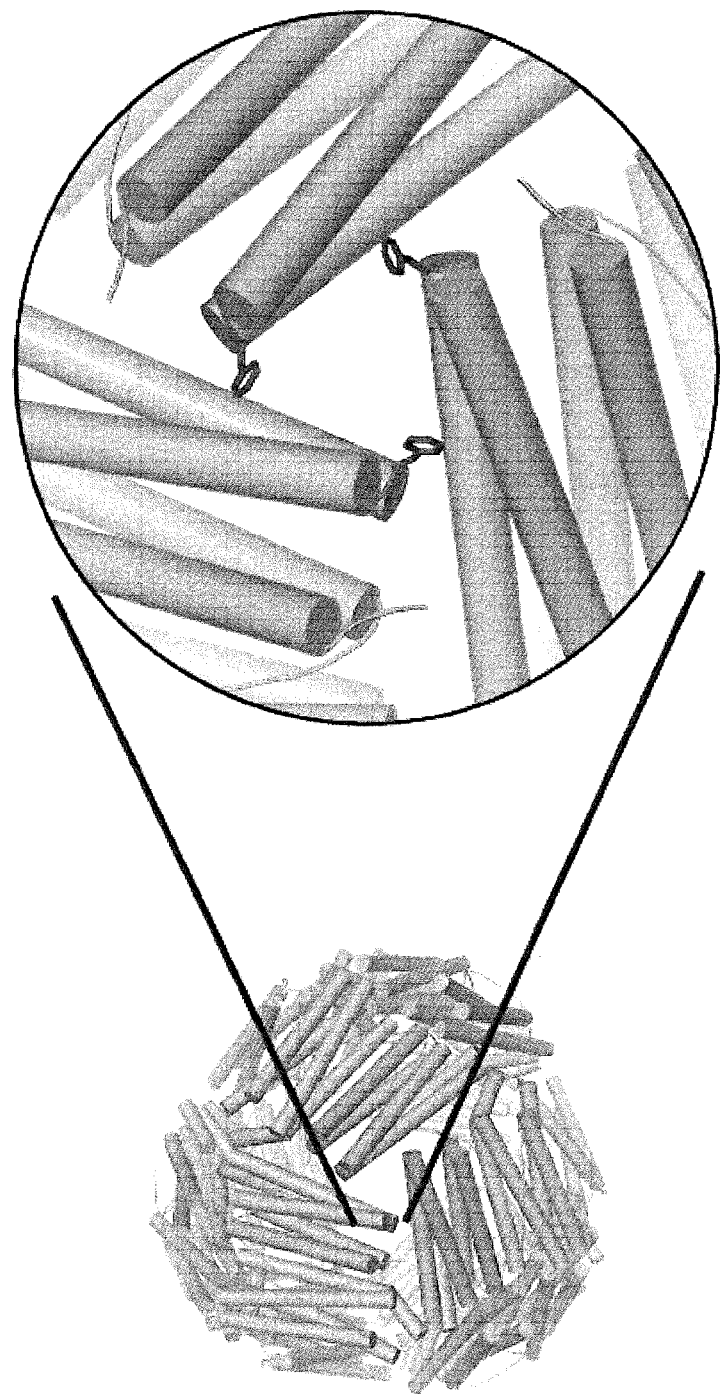
FIGS. 12A-12I show effect of F116H mutation on cage disassembly. All the size exclusion chromatography experiments were performed with 25 mM Tris-citrate, pH 8.0 and 5.8 buffers. For h6NE-GFPuv(+) and F116HNE-GFPuv(+), the fractions were analyzed for fluorescence reading (excitation wavelength 395 nm, emission wavelength 509 nm) and plotted on to the chromatogram.
Figure 12C:
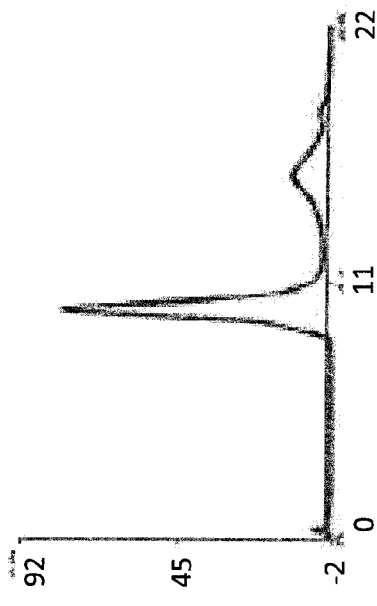
Figure 12E:
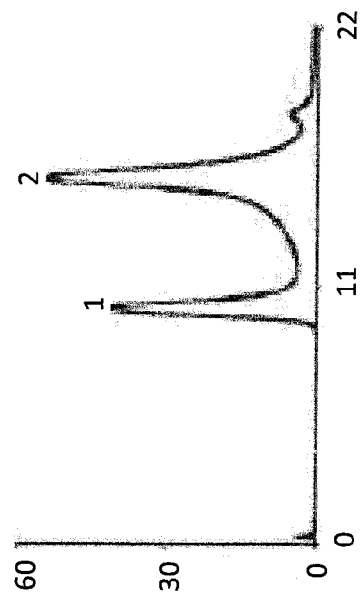
Figure 12B:
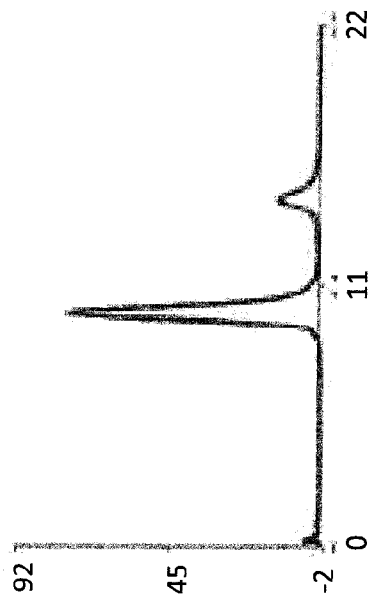
Figure 12D:
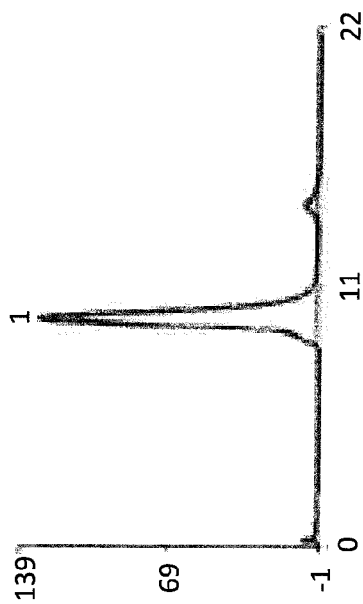
Figure 12F:
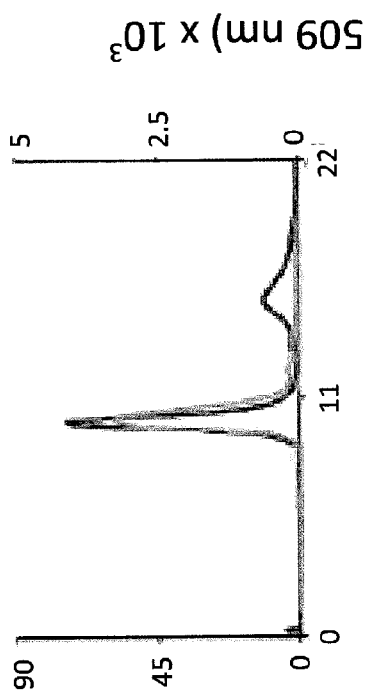
Figure 12G:
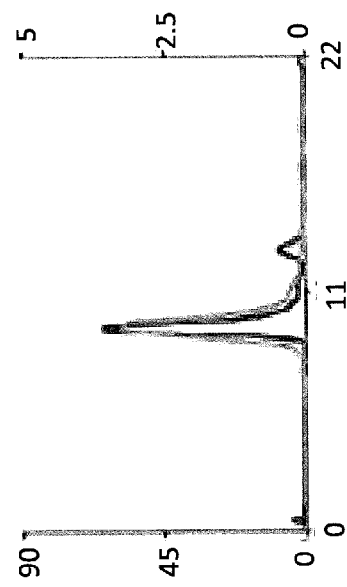
Figure 12H:
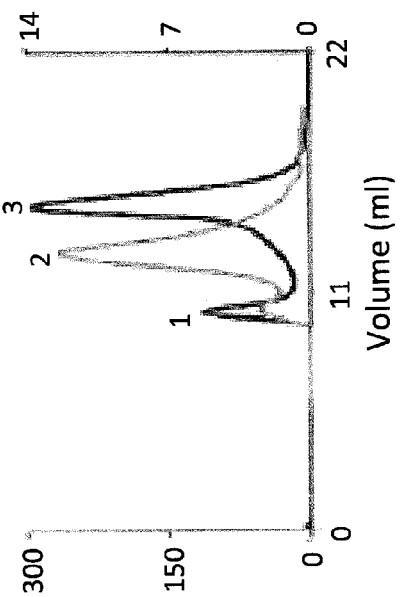
Figure 12I:
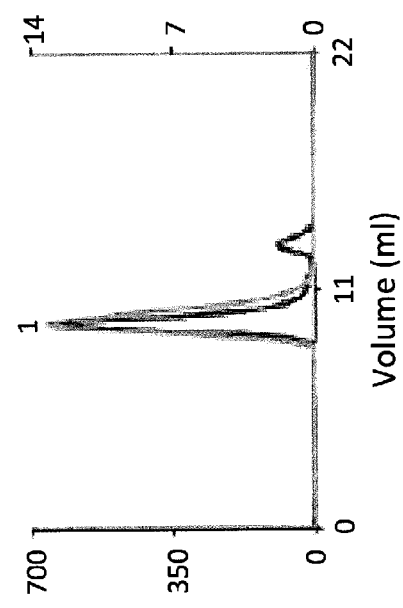
Figure 13B:
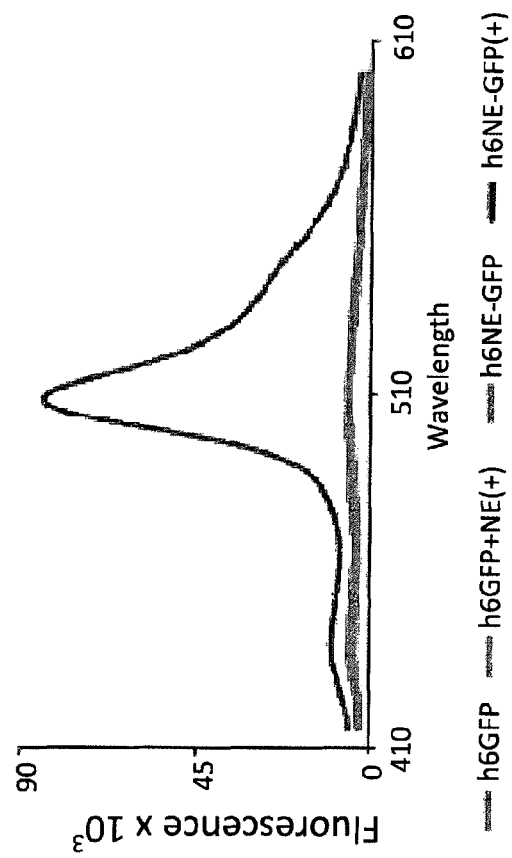
FIGS. 13A-13D show effect of L-arabinose on the functional expression of GFP.
Figure 13A:
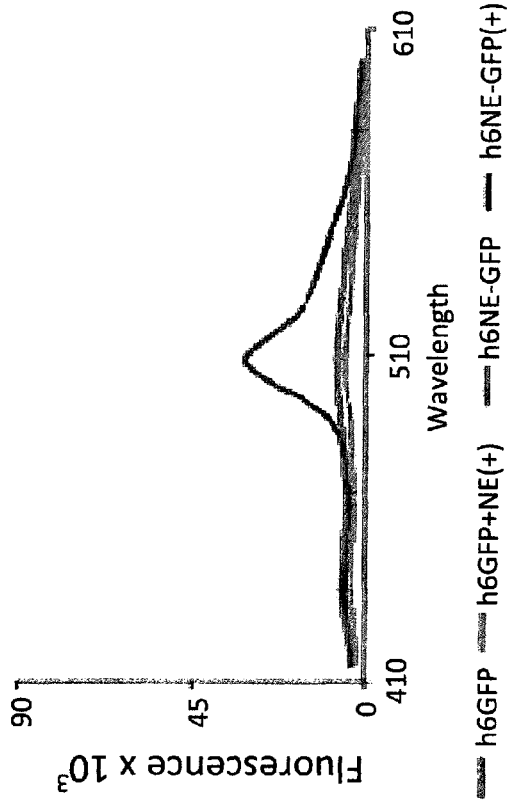
Figure 13D:
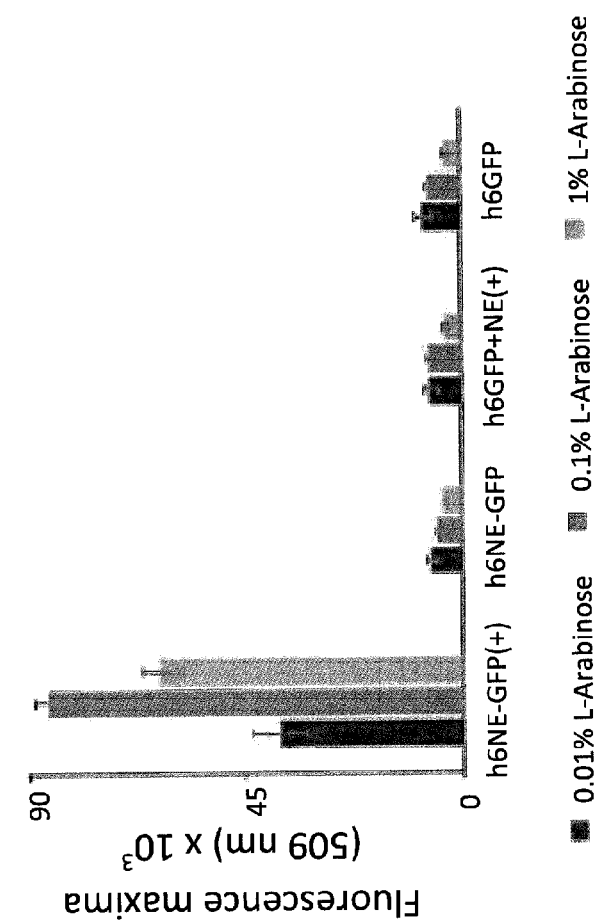
Figure 13C:
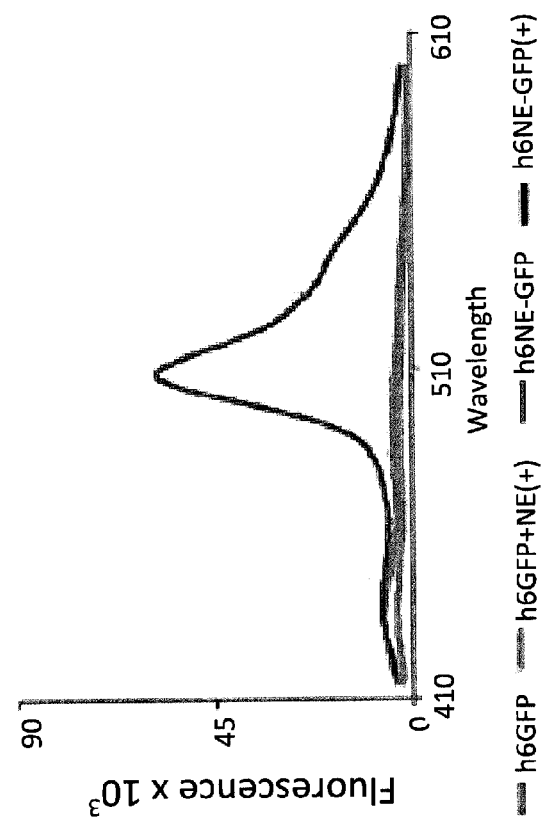
Figure 14:
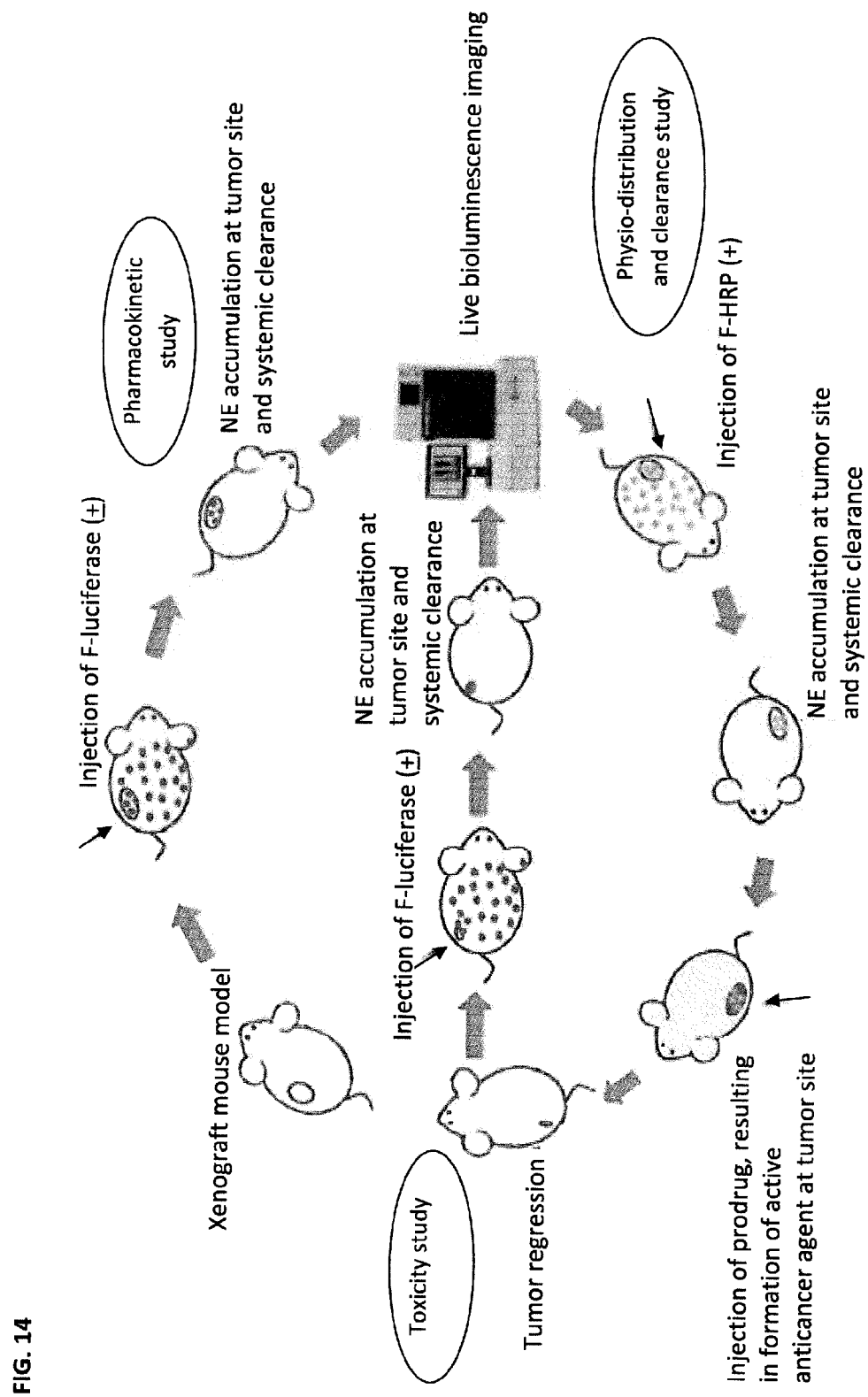
FIG. 14 shows an overview of a theranostic experimental flow. This approach is a multistep process that first binds a converting agent (the encapsulated enzyme) to a target, which in turn, converts a benign prodrug into a toxic product. This then results in tumor treatment with a very high therapeutic index as the treating chemotherapeutic is preferentially synthesized near the site of the therapeutic target organ or tumor.
Figure 15A:
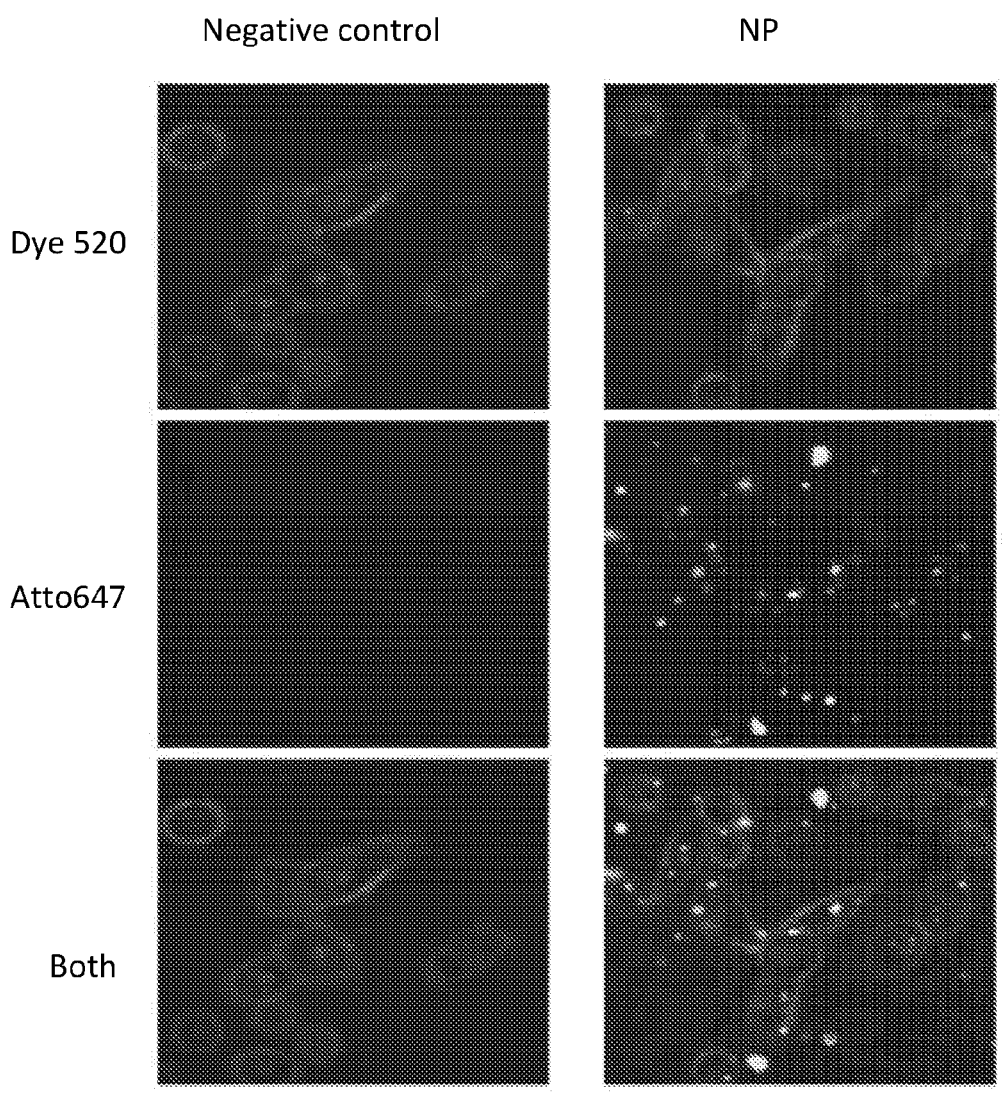
FIGS. 15A-15B show confocal images of nanocage uptake by MDA-MB-231 cancer cell line. GE11 and D4 are peptides that bind EGFR, which is overexpressed on cancer cells. NP=nanoparticle.
Figure 15B:
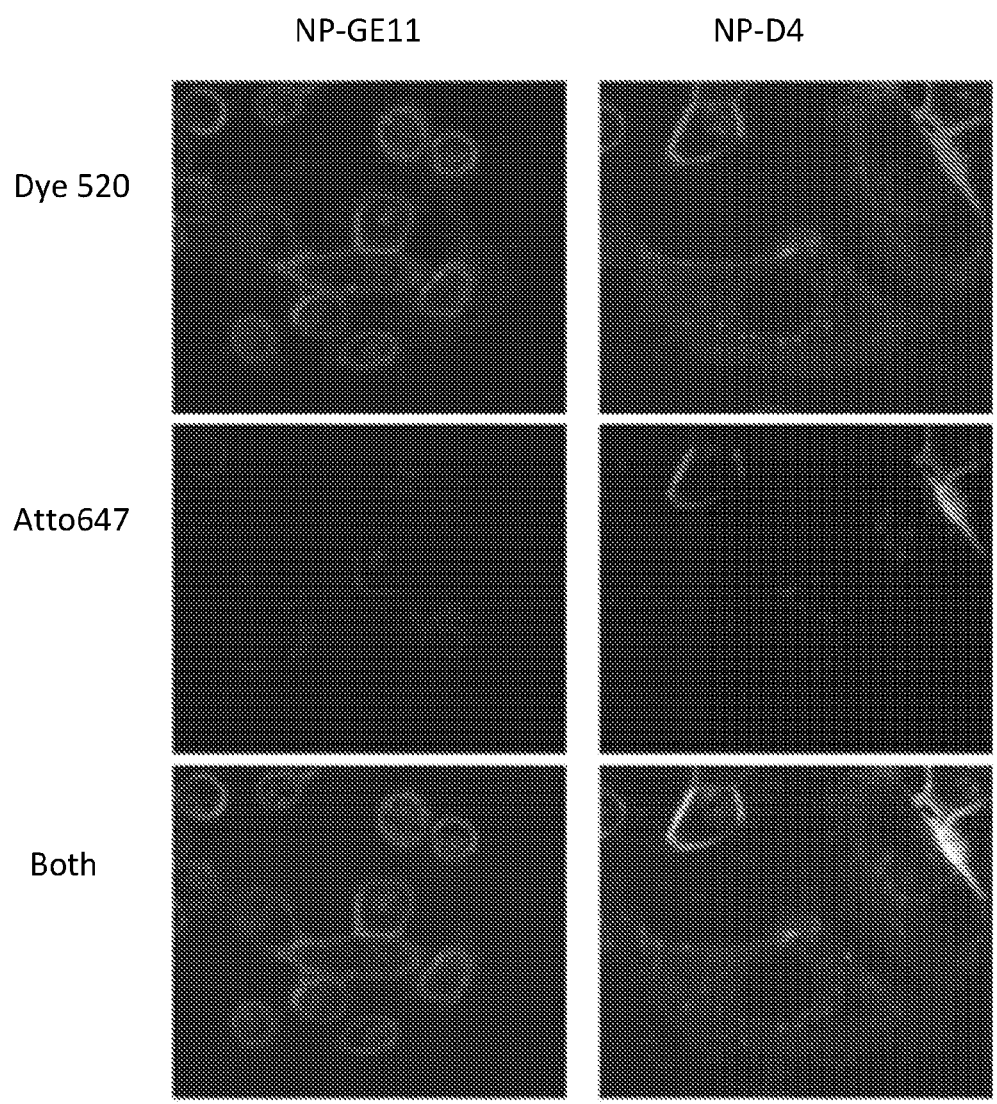
Figure 16A:
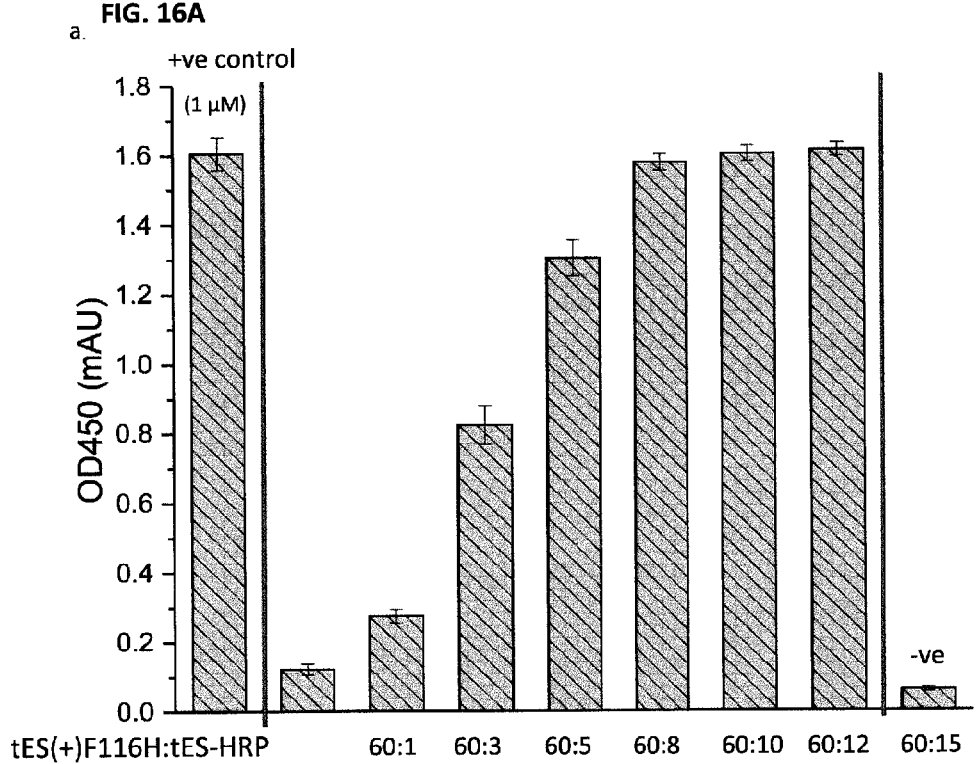
FIGS. 16A-16B show effect of different molar ratios and charge of tES subunits on native HRPC encapsulation in vitro.
Figure 16B:
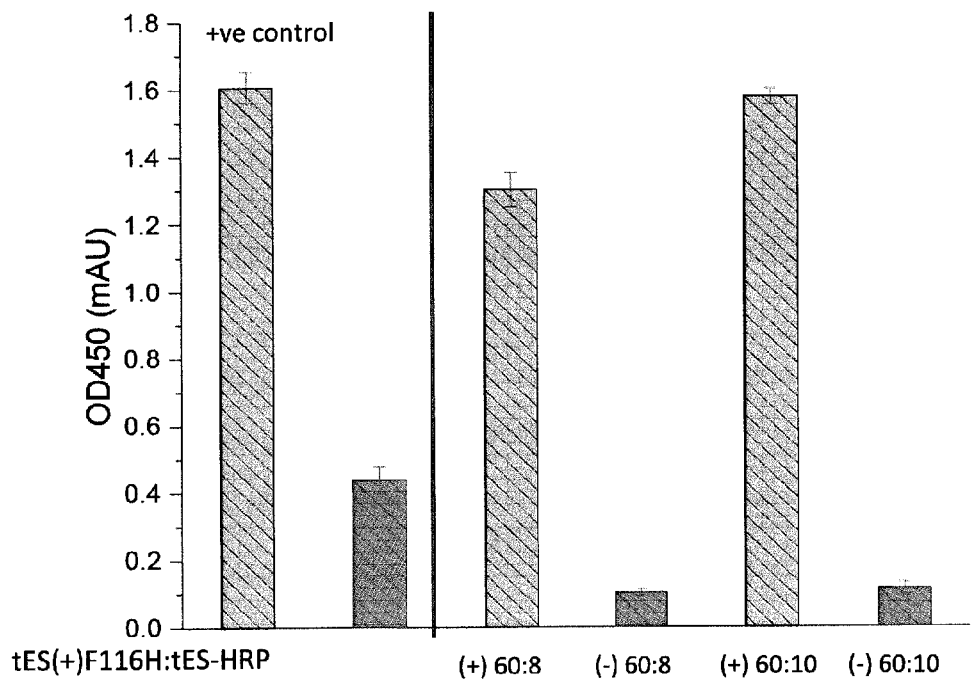
Figure 17A:
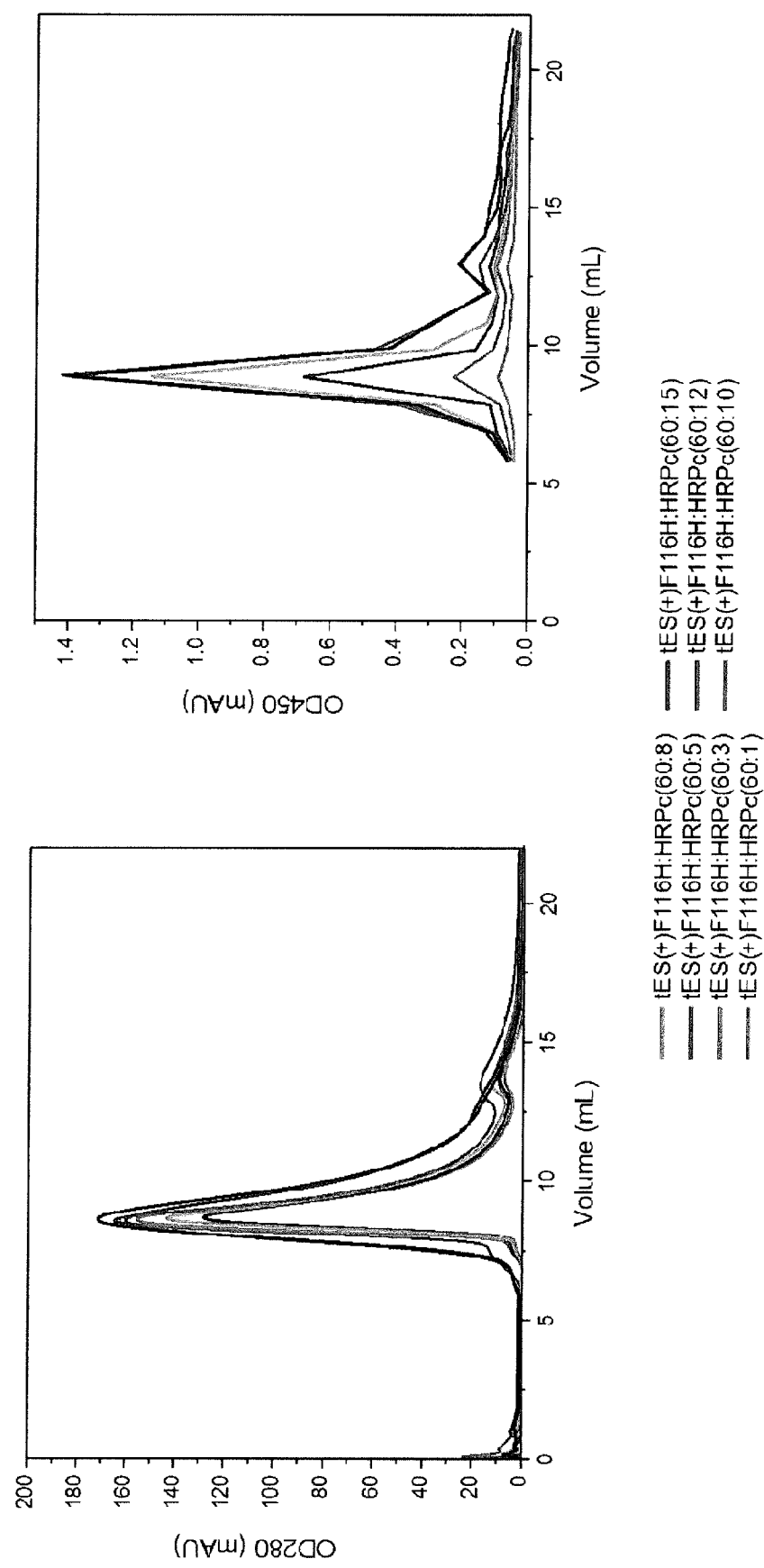
FIGS. 17A-17D show effect of different concentrations of tES subunits on HRPC folding in vitro.
Figure 17B:
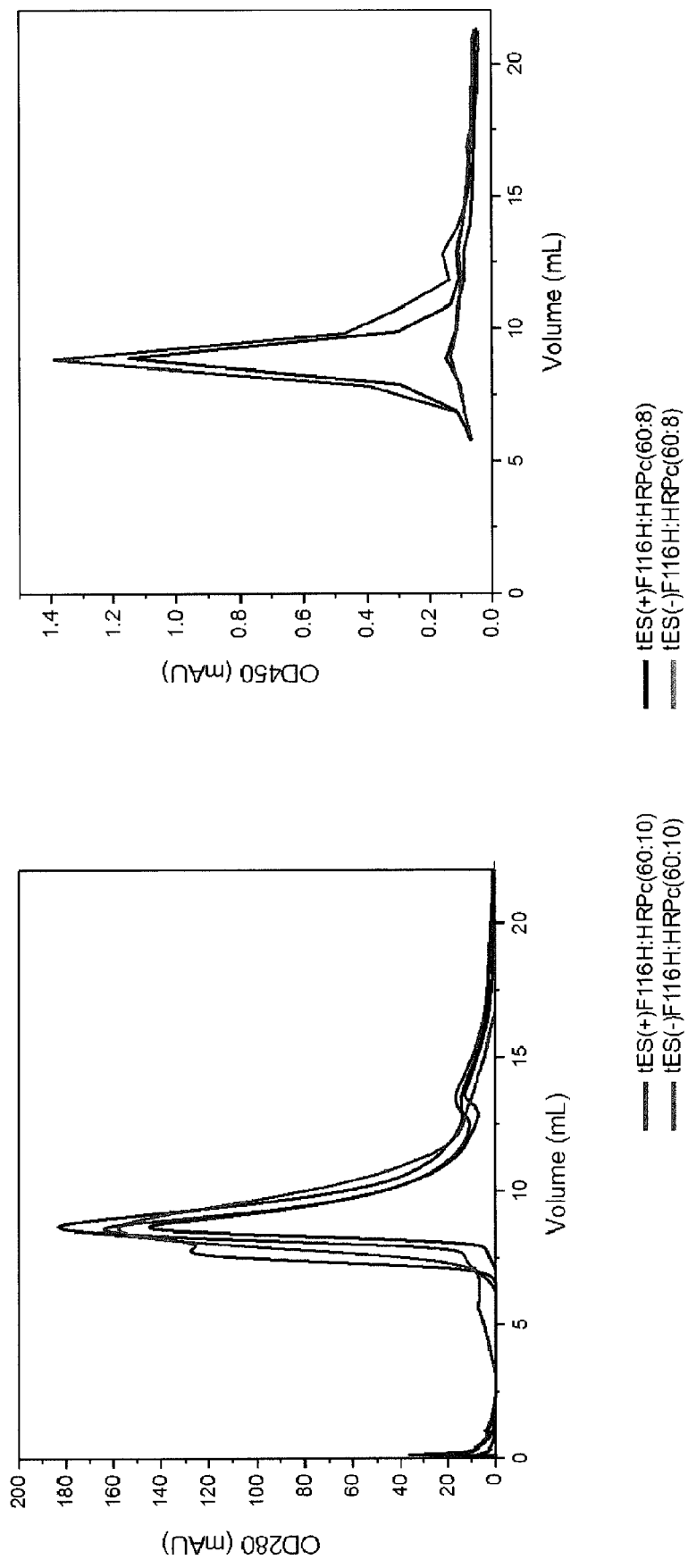
Figure 17D:
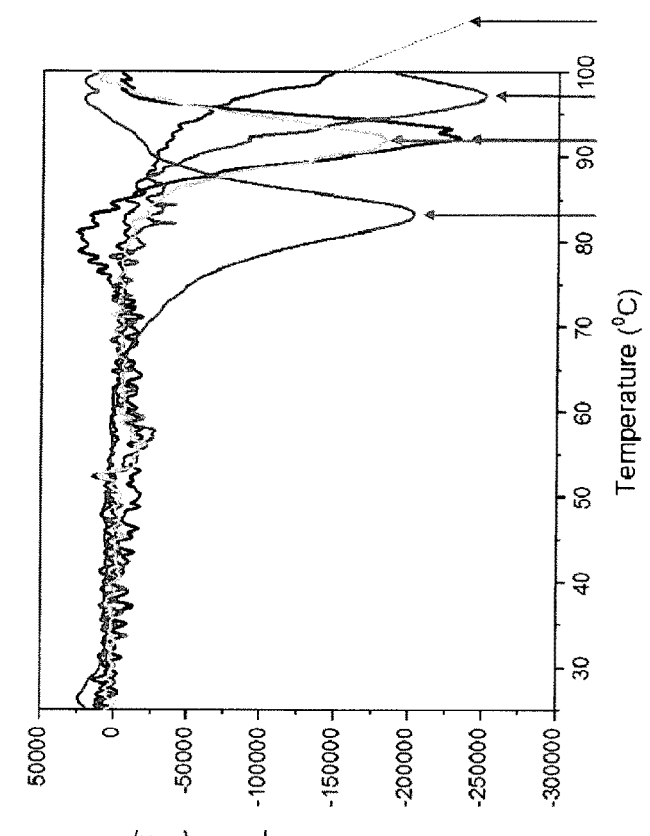
Figure 17C:
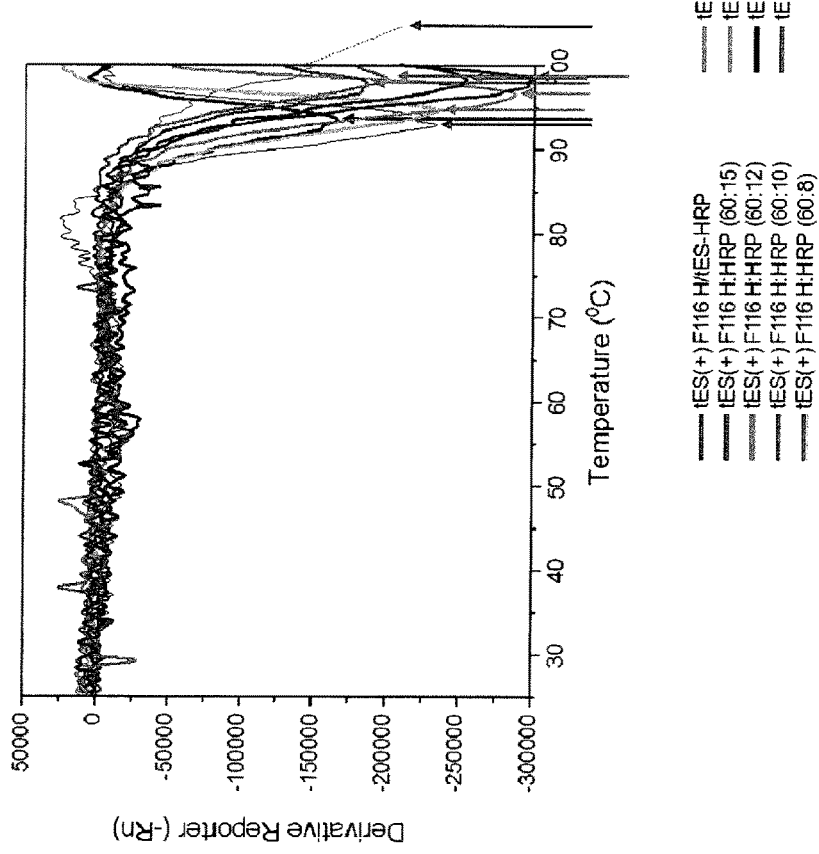
Figure 18A:
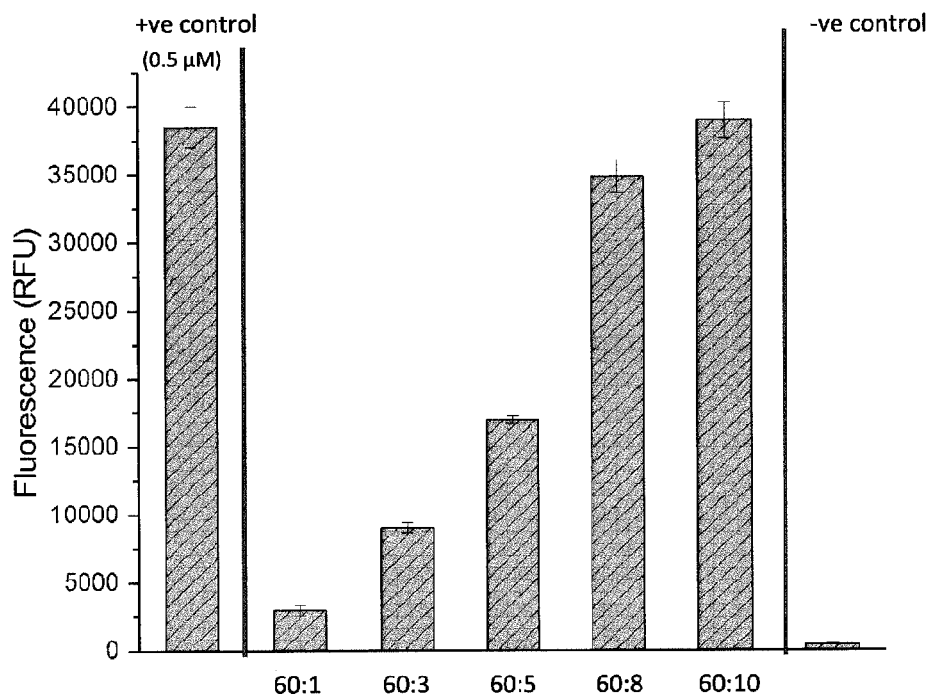
FIGS. 18A-18D show effect of different molar ratios and charge of tES subunits on native GFPuv encapsulation in vitro.
Figure 18B:
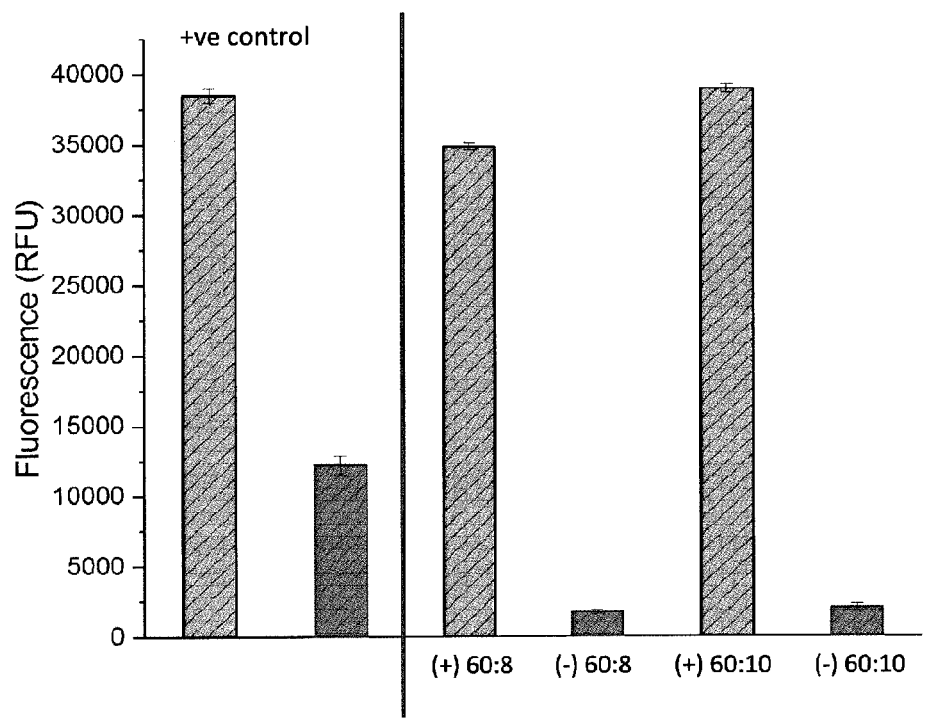
Figure 18C:
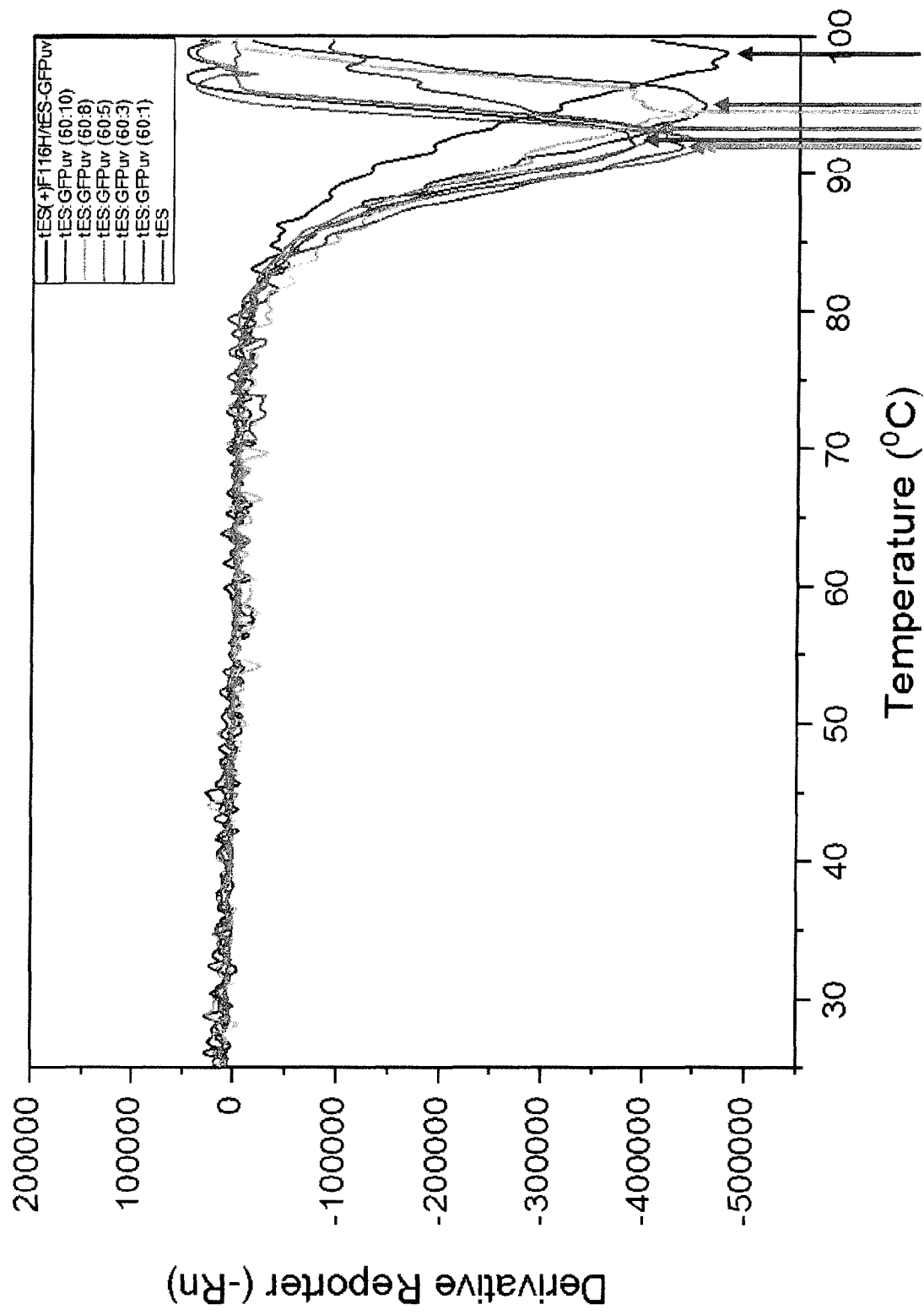
Figure 18D:
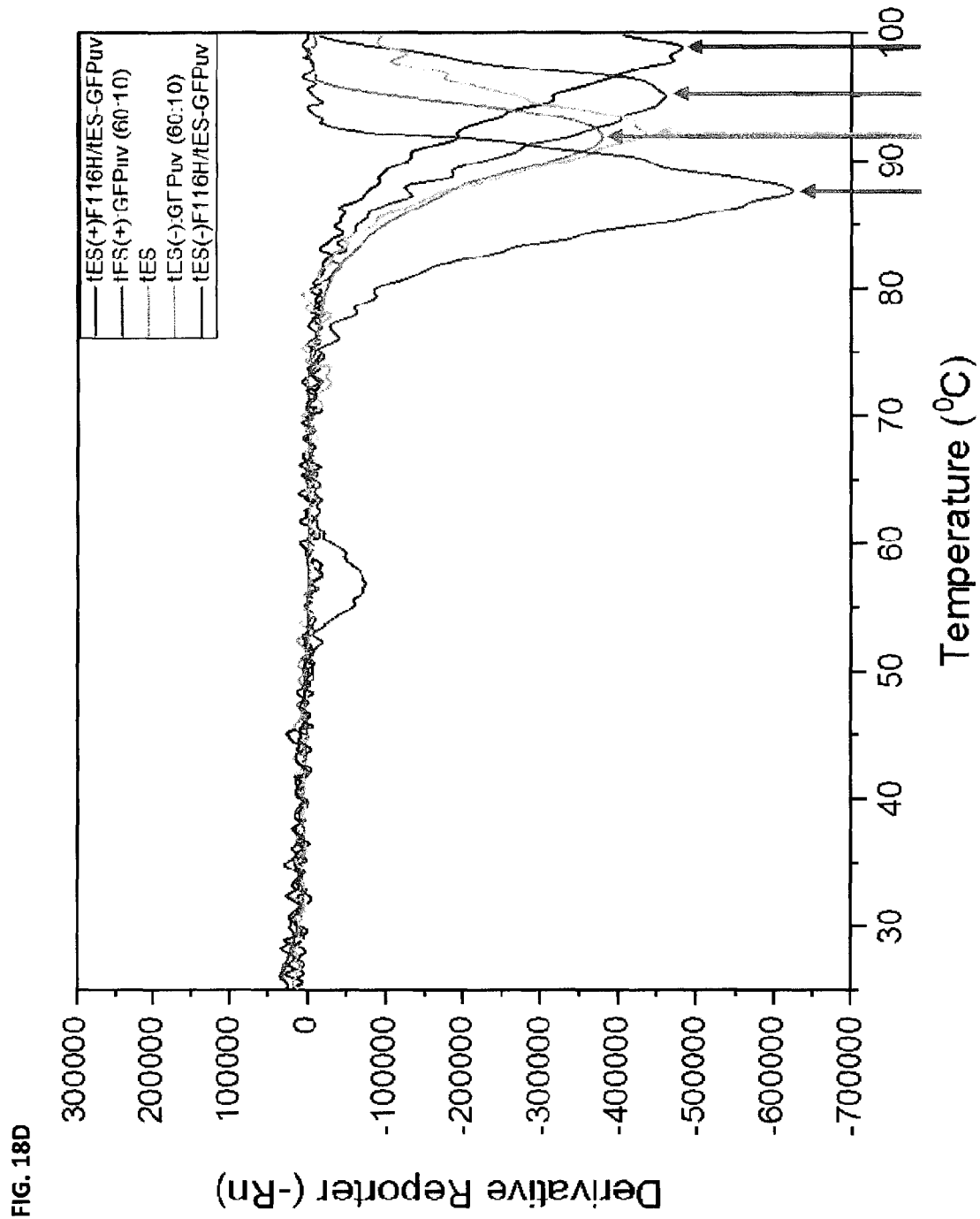
Figure 19:
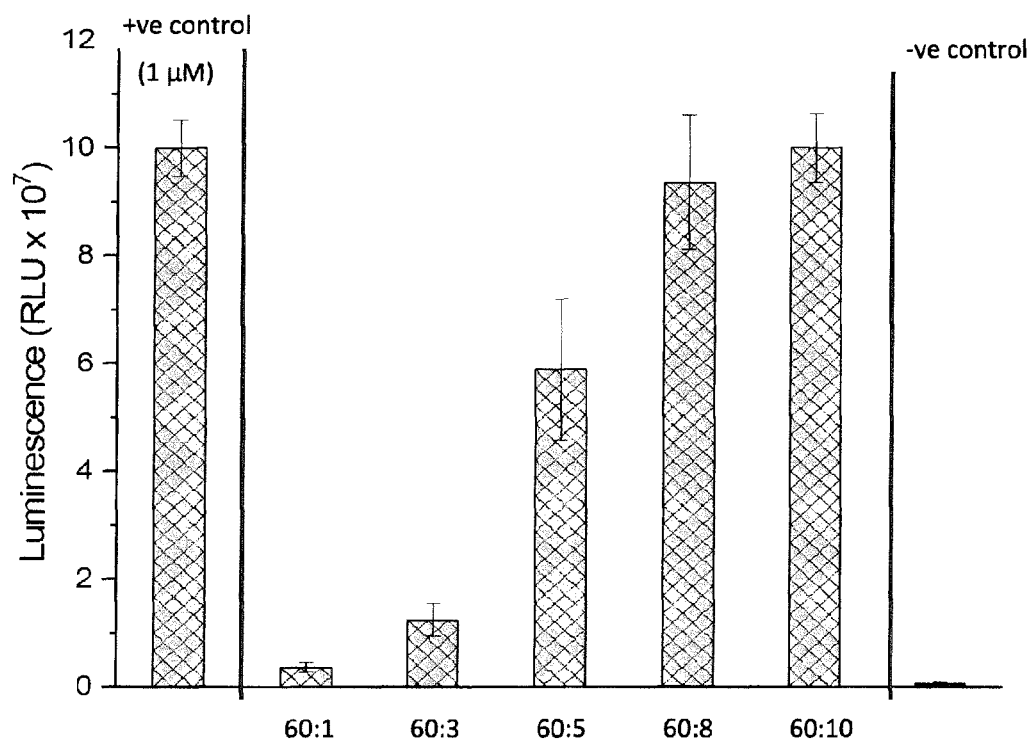
FIG. 19 shows effect of different molar ratios of tES(+)F116H subunits on native rLuc encapsulation and folding in vitro measured using rLuc luminescence.+ve control is tES:tES-rLuc (1µM); −ve control is rLuc.

Column 26, Line 24, delete "(FIG. 10" and insert -- (FIG. 1C --.

Signed and Sealed this
Fifteenth Day of August, 2023

Katherine Kelly Vidal
*Director of the United States Patent and Trademark Office*

CERTIFICATE OF CORRECTION (continued)
U.S. Pat. No. 11,510,881 B2

Column 27, Line 18, delete "[h6P0I" and insert -- [h6POI --.

Column 27, Line 51, delete "POls" and insert -- POIs --.

Column 30, Line 2, delete "16A-" and insert -- 16A, --.